US008007781B2

(12) United States Patent
Wu et al.

(10) Patent No.: US 8,007,781 B2
(45) Date of Patent: Aug. 30, 2011

(54) MOLECULAR VACCINE LINKING AN ENDOPLASMIC RETICULUM CHAPERONE POLYPEPTIDE TO AN ANTIGEN

(75) Inventors: Tzyy-Choou Wu, Stevenson, MD (US); Chien-Fu Hung, Timonium, MD (US)

(73) Assignee: The Johns Hopkins University, Baltimore, MD (US)

( * ) Notice: Subject to any disclaimer, the term of this patent is extended or adjusted under 35 U.S.C. 154(b) by 512 days.

(21) Appl. No.: 12/014,541

(22) Filed: Jan. 15, 2008

(65) Prior Publication Data
US 2009/0148471 A1 Jun. 11, 2009

Related U.S. Application Data

(63) Continuation of application No. 10/343,448, filed as application No. PCT/US01/24134 on Aug. 2, 2001, now Pat. No. 7,342,002.

(60) Provisional application No. 60/222,902, filed on Aug. 3, 2000.

(51) Int. Cl.
*A61K 48/00* (2006.01)
*C12P 21/06* (2006.01)

(52) U.S. Cl. .................. 424/93.21; 424/93.2; 435/69.1; 435/69.7

(58) Field of Classification Search .................. None
See application file for complete search history.

(56) References Cited

U.S. PATENT DOCUMENTS

| | | |
|---|---|---|
| 4,898,730 A | 2/1990 | Levy et al. |
| 5,217,879 A | 6/1993 | Huang et al. |
| 5,348,945 A | 9/1994 | Berberian et al. |
| 5,426,097 A | 6/1995 | Stern et al. |
| 5,547,846 A | 8/1996 | Bartsch et al. |
| 5,582,831 A | 12/1996 | Shinitzky |
| 5,591,716 A | 1/1997 | Siebert et al. |
| 5,618,536 A | 4/1997 | Lowy et al. |
| 5,629,161 A | 5/1997 | Muller et al. |
| 5,674,486 A | 10/1997 | Sobol et al. |
| 5,744,133 A | 4/1998 | Lathe et al. |
| 5,750,119 A | 5/1998 | Srivastava |
| 5,821,088 A | 10/1998 | Darzins et al. |
| 5,830,464 A | 11/1998 | Srivastava |
| 5,834,309 A | 11/1998 | Thompson et al. |
| 5,837,251 A | 11/1998 | Srivastava |
| 5,844,089 A | 12/1998 | Hoffman et al. |
| 5,854,202 A | 12/1998 | Dedhar |
| 5,855,891 A | 1/1999 | Lowy et al. |
| 5,935,576 A | 8/1999 | Srivastava |
| 5,948,646 A | 9/1999 | Srivastava |
| 5,951,975 A | 9/1999 | Falo, Jr. et al. |
| 5,962,318 A | 10/1999 | Rooney et al. |
| 5,997,869 A | 12/1999 | Goletz et al. |
| 6,007,821 A | 12/1999 | Srivastava et al. |
| 6,013,262 A | 1/2000 | Frazer et al. |
| 6,017,544 A | 1/2000 | Srivastava |
| 6,017,735 A | 1/2000 | O'Hare et al. |
| 6,020,309 A | 2/2000 | Campo et al. |
| 6,030,618 A | 2/2000 | Srivastava |
| 6,046,158 A | 4/2000 | Ariizumi et al. |
| 6,066,716 A | 5/2000 | Wallen et al. |
| 6,235,523 B1 | 5/2001 | Gajewczyk et al. |
| 6,331,388 B1 | 12/2001 | Malkovsky et al. |
| 6,399,070 B1 | 6/2002 | Srivastava et al. |
| 6,403,080 B1 | 6/2002 | Segal |
| 6,410,027 B1 | 6/2002 | Srivastava |
| 6,410,028 B1 | 6/2002 | Srivastava |
| 6,541,010 B1 | 4/2003 | Johnston et al. |
| 6,734,173 B1 | 5/2004 | Wu et al. |
| 7,001,995 B1 | 2/2006 | Neeper et al. |
| 7,318,928 B2 | 1/2008 | Wu et al. |
| 7,342,002 B2 | 3/2008 | Wu et al. |
| 2001/0034042 A1 | 10/2001 | Srivastava |
| 2002/0064771 A1 | 5/2002 | Zhong et al. |
| 2002/0091246 A1 | 7/2002 | Pardoll et al. |
| 2002/0182586 A1 | 12/2002 | Morris et al. |
| 2004/0028693 A1 | 2/2004 | Wu et al. |
| 2004/0086845 A1 | 5/2004 | Wu et al. |
| 2004/0259247 A1 | 12/2004 | Tuschl et al. |
| 2005/0048467 A1 | 3/2005 | Sastry et al. |
| 2005/0054820 A1 | 3/2005 | Wu et al. |
| 2005/0277605 A1 | 12/2005 | Wu et al. |
| 2007/0026076 A1 | 2/2007 | Wu et al. |

FOREIGN PATENT DOCUMENTS

| | | |
|---|---|---|
| CA | 2413543 | 1/2002 |
| EP | 0 763 740 | 3/1997 |
| WO | WO-89/12455 | 12/1989 |
| WO | WO-92/05248 | 4/1992 |
| WO | WO-93/20844 | 10/1993 |
| WO | WO-94/04696 | 3/1994 |
| WO | WO-94/29459 | 12/1994 |

(Continued)

OTHER PUBLICATIONS

Aguiar et al., "Enhancement of the immune response in rabbits to a malaria DNA vaccine by immunization with a needle-free jet device," Vaccine, 20:275-280 (2001).
Alexander et al., "Development of High Potency Universal DR-Restricted Helper Epitopes by Modification of High Affinity DR-Blocking Peptides," Immunity, 1:751-761 (1994).
Anonymous: "E7 vaccine (NSC 723254)," Timeless Success Story, Online, XP002394109 (2002).
Anthony et al., "Priming of CD8 CTL Effector Cells in Mice by Immunization with a Stress-Protein-Influenza Virus Nucleoprotein Fusion Molecule," Vaccine, 17(4):373-383 (1999).

(Continued)

*Primary Examiner* — Q. Janice Li
(74) *Attorney, Agent, or Firm* — Foley Hoag LLP

(57) ABSTRACT

This invention provides compositions and methods for inducing and enhancing immune responses, such as antigen-specific cytotoxic T lymphocyte (CTL) responses, using chimeric molecules comprising endoplasmic reticulum chaperone polypeptides and antigenic peptides. In particular, the invention provides compositions and methods for enhancing immune responses induced by polypeptides made in vivo by administered nucleic acid, such as naked DNA or expression vectors, encoding the chimeric molecules. The invention provides a method of inhibiting the growth of a tumor in an individual. The invention also provides novel self-replicating RNA virus constructs for enhancing immune responses induced by chimeric polypeptides made in vivo.

7 Claims, 9 Drawing Sheets

FOREIGN PATENT DOCUMENTS

| WO | WO-95/17212 | 6/1995 |
|---|---|---|
| WO | WO-96/36643 | 11/1996 |
| WO | WO-97/03703 | 2/1997 |
| WO | WO-97/06685 | 2/1997 |
| WO | WO-97/41440 | 11/1997 |
| WO | WO-98/23735 | 6/1998 |
| WO | WO-98/32866 | 7/1998 |
| WO | WO-98/48003 | 10/1998 |
| WO | WO-99/07860 | 2/1999 |
| WO | WO-99/42472 | 8/1999 |
| WO | WO-99/58658 | 11/1999 |
| WO | WO 99/07869 | 12/1999 |
| WO | WO-99/65940 | 12/1999 |
| WO | WO-01/29233 | 4/2001 |
| WO | WO-02/09645 | 2/2002 |
| WO | WO-02/12281 | 2/2002 |
| WO | WO-02/061113 | 8/2002 |
| WO | WO-02/074920 | 9/2002 |
| WO | WO-03/008543 | 1/2003 |
| WO | WO-03/083052 | 10/2003 |
| WO | WO-03/085085 | 10/2003 |
| WO | WO-2004/030636 | 4/2004 |
| WO | WO-2004/060304 | 7/2004 |
| WO | WO-2004/098526 | 11/2004 |
| WO | WO-2005/047501 | 5/2005 |
| WO | WO-2005/081716 | 9/2005 |
| WO | WO-2006/073970 | 7/2006 |
| WO | WO-2006/081323 | 8/2006 |

OTHER PUBLICATIONS

Asea et al., "Novel Signal Transduction Pathway Utilized by Extracellular HSP70," Journal of Biological Chemistry, 277(7)15028-15034 (2002).
Ausbel, et al., Current Protocols in Molecular Biology, John Wiley & Sons, 1989.
Babiuk et al., "Immunization of animals: from DNA to the dinner plate," Veterinary Immunology and Immunopathology, 72:189-202 (1999).
Bae et al., "Therapeutic Synergy of Human Papillomavirus E7 Subunit Vaccines plus Cisplatin in an Animal Tumor Model: Casual Involvement of Increased Sensitivity of Cisplatin-Treated Tumors to CTL-Mediated Killing in Therapeutic Synergy," Clin. Cancer Res., 13(1):341-349 (2007).
Banchereau, J., "Dendritic Cells: Therapeutic Potentials," Transfus Sci 18(2):313-326 (1997).
Banu et al., "Modulation of Haematopoietic Progenitor Development by FLT-3 Ligand,"Cylokine, 11(9):679-688 (1999).
Barrios et al., "Mycobacterial heat-shock proteins as carrier molecules. II: The use of the 70-kDa mycobacterial heat-shock protein as carrier for conjugated vaccines can circumvent the need for adjuvants and Bacillus Calmette Guerin priming," Eur. J. Immunol., 22:1365-1372 (1992).
Becker et al., "CD40, an extracellular receptor for binding and uptake of Hsp70-peptide complexes," Journal of Cell Biology, 158(7):1277-1285 (2002).
Beissbarth et al., "Increased efficiency of folding and peptide loading of mutant MHC class I molecules," Eur. J. Immunol., 30:1203-1213 (2000).
Benton et al., "DNA Vaccine Strategies for the Treatment of Cancer," Curr Top Microbiol Immunol., 226:1-20 (1998).
Bhoola et al., "Diagnosis and management of epithelial ovarian cancer," Obstet. Gynecol., 107(6):1399-1410 (2006).
Biragyn et al., "Genetic fusion of chemokines to a self tumor antigen induces protective, T-Cell dependent antitumor immunity," Nature Biotechnology, 17:253-258 (1993) Abstract.
Blachere et al., "Heat shock Protein-peptide complexes, Reconstituted in vitro, Elicit Peptide-specific cytotoxic T Lymphocyte Response and Tumor Immunity," J. Exp. Med., 186(8)1315-1322 (1997).
Blachere et al. "Heat shock proteins against cancer," J. of Immunotherapy Emphasis Tumor Immunol., 14:352-356 (1993).
Bohm et al., "Routes of plasmid DNA vaccination that prime murine humoral and cellular immune responses," Vaccine, 16:949-954 (1998).
Boyle et al, "Enhanced responses to a DNA vaccine encoding a fusion antigen that directed to sites of immune induction," Nature, 392:408-411 (1998).
Bredenbeek et al., "Sindbis Virus Expression Vectors: Packaging of RNA Replicons by Using Defective Helper RNAs," Journal of Virology, 67(11):6439-6446 (1993).
Breitburd et al., "Human papillomavirus vaccines," Cancer Biology, 9:431-445 (1999).
Brossart et al., "Identification of HLA-A2-Restricted T-Cell Epitopes Derived From the MUC1 Tumor Antigen for Broadly Applicable Vaccine Therapies," Blood, 93(12):4309-4317 (1999).
Buck et al., "Efficient Intracellular Assembly of Papillomaviral Vectors," Journal of Virology, 78(2):751-757 (2004).
Bueler et al., "Induction of Antigen-Specific Tumor Immunity by Genetic and Cellular Vaccines against MACE: Enhanced Tumor Protection by Coexpression of Granulocyte-Macrophage Colony Stimulating Factor and B7-1," Molecular Medicine, 2(5):545-555 (1996).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111:2129-2138 (1990).
Carbonetti et al., "Intracellular Delivery of a Cytolytic T-Lymphocyte Epitope Peptide by Pertussis Toxin to Major Histocompatibioity Complex Class l without Involvement of the Cytosolic Class I Antigen Processing Pathway," Infection and Immunity 67(2):602-607 (1999).
Celluzzi et al., "Peptide-pulsed Dendritic Cells Induce Antigen-specific, CTL-mediated Protective Tumor Immunity," J. Exp. Med. 183:283-287 (1996).
Chang et al., "Cancer Immunotherapy Using Irradiated Tumor Cells Secreting Heat Shock Protein 70," Cancer Res., 67(20):10047-10057 (2007).
Chen et al., Design of a genetic immunotoxin to eliminate toxin immunogenicity, Gene Therapy, 1992, vol. 2, p. 116-123.
Chen et al., "Human pappillomavirus type 16 nucleoprotein E7 is a tumor rejection antigen," PNAS, 88:110-114 (1991).
Chen et al, "Induction of Cylotoxic T Lymphocytes Specific for a Syngeneic Tumor Expressing the E6 Oncoprotein of Human Papillomavirus Type 16," Journal of Immunology, 148:2617-2621 (1992).
Chen, W. et al., "Modulatory Effects of the Human Heat Shock Protein 70 on DNA Vaccination," J. Biomed. Sci., 7(5):412-419 (2000).
Chen et al., "Mycobacterial heat shock protein 65 enhances antigen cross-presentation in dendritic cells independent of Toll-like receptor 4 signaling," Journal of Leukocyte Biology, 75:260-266 (2004).
Cheng et al., "Bax-independent inhibition of apoptosis by Bcl-$x_L$," Nature, 379(8):554-556 (1996).
Cheng et al, (Report on Results of Monographic Study # NSC91-2314-B-002-377, National Taiwan University, National Scientific Committee, available to public Oct. 31, 2003).
Cho et al., "Enhanced cellular immunity to hepatitis C virus nonstructural proteins by codelivery of granulocyte macrophage-colony stimulating factor gene in intramuscular DNA immunization," Vaccine, 17:1136-1144 (1999).
Chow et al., "Development of Thi1 and Th2 Populations and the Nature of Immune Responses to Hepatitis B Virus DNA Vaccines Can Be Modulated by Codelivery of Various Cytokine Genes," The Journal of Immunology, 160(3):1320-1329 (1998).
Chu et al., "Cancer Immunotherapy Using Adjuvant-Free, Fusion Protein Encoding M. Golvis BCG HSP65 and HPV16 E7," FASEB Journal 12(5), Mar. 20, 1998 Abstract XP000960840.
Chu et al., Immunotherapy of a human papillomavirus (HPV) type 16 E7-expressing tumor by administration of fusion protein comprising *Mycobacterium bovis* bacille Calmette-Guerin (BGG) hsp65 and HPV 16 E7, Clin. Exp. Immunol., 121(2):216-225 (2000).
Ciupitu et al., "Immunization with a Lymphocytec Choriomeningitis Virus Peptide Mixed Heat Sbcok Protein 70 Results in Protective Antiviral Immunity and Specific Cytotoxic T Lymphocytes," J. Exp. Med., 187(5)685-691 (1998).
Corr et al., "Costimulation Provided by DNA Immunization Enhances Antitumor Immunity," The Journal of Immunology, 159(10):4999-5004 (1997).

Coukos et al., "Immunotherapy for gynaecological malignancies," Expert Opin. Biol. Ther., 5(9):1193-1210 (2005).

Crum et al., "Vaccines for Cervical Cancer," Cancer Journal from Scientific American, 9(5):368-376 (2003).

Davidoff et al., "Immune Response to P53 is Dependent upon P53/HSP70 Complexes in Breast Cancers," Proceedings of the National Academy of Sciences of USA, 89(8):3442 (1992).

Debinsky et al., "A Wide Range of Human Cancers Express Interleukin 4 (IL-4) Receptors That Can Be Targeted with Chimeric Toxin Composed of IL-4 and *Pseudomonas* Exotoxin," The Journal of Biological Chemistry, 268(19):14065-14070 (1993).

de Jong et al., "Enhancement of human papillomavirus (HPV) type 16 E6 and E7-specific T-cell immunity in healthy volunteers through vaccination with TA-CIN, an HPV16 L2E7E6 fusion protein vaccine," Vaccine, 20:3456-3464 (2002).

Dialynas et al., "Characterization of the Murine T Cell Surface Molecule Designated L3T4, Identified by Monocolonal Antibody GK1,5: Similarity of L3T4 to the Human Leu-3/T4 Molecule," J. Immunol., 131(5):2445-2451 (1983).

Donnelly et al., "DNA Vaccines," Annual Review of Immunology, 15:617-48 (1997).

Donnelly et al., "DNA Vaccines: Progress and Challenges," J. Immunol., 175:633-639 (2005).

Donnelly et al., "Targeted delivery of peptide epitopes to class I major histocompatibility molecules by a modified *Pseudomonas* exotoxin," Proc. Natl. Acad. Sci. USA 90:3530-3534 (1993).

Drake et al., "Assessing tumor growth and distribution in a model of prostate cancer metastasis using bioluminescence imaging." Clin. Exp. Metastasis, 22:674-684 (2005).

Eiben et al., "Establishment of an HLA-a*0201 Human Papillovarus Type 16 Tumor Model to Determine the Efficacy of Vaccination Strategies in HLA-A*0201 Transgenic Mice," Cancer Research, 62:5792-5799 (2002).

Eisenbraun et al., "Examination of parameters affecting the elicitation of humoral immune responses by particle bombardment-mediated genetic immunization," DNA Cell Biol., 12(9):791-797 (1993).

Elliott et al., "Intercellular trafficking and protein delivery by a herpesvirus structural protein," Cell, 88(2):223-233 (1997).

Elsaghier et al., "Localisation of Linear Epitopes at the Carboxy-Terminal End of the Mycobacterial 71 KDA Heat Shock Protein," Molecular Immunology 29(9):1153-1156 (1992).

Feltkamp et al., "Vaccination with cytotoxic T lymphocyte epitope-containing peptide protects against a tumor induced by human papillomavirus type 16-transformed cells," Eur. J. Immunol., 23(9):2242-2249 (1993).

Fernando et al., "Expression, purification and immunological characterization of the transforming protein E7, from cervical cancer-associated human papilloma virus type 16," Clin. Exp. Immunol., 115:397-403 (1999).

Flohe et al., "Human Heat Shock Protein 60 Induces Maturation of Dendritic Cells Versus a Th1-Promoting Phenotype," The Journal of Immunology, 170:2340-2348 (2003).

Fominaya et al., "Target Cell-specific DNA Transfer Mediated by a Chimeric Multidomain Protein,"The Journal of Biological Chemistry, 271(18):10560-10568 (1996).

Fomsgaard et al., "Improved Humoral and Cellular Immune Responses Against the gp120 V3 Loop of HIV-1 Following Genetic Immunization with a Chimeric DNA Vaccine Encoding the V3 Inserted into the Hepatitis B Surface Antigen," Scand J. Immunol., 47(4):289-95 (1998).

Forni et al., "Cytokine gene-engineered vaccines," Curr. Opin. Mol. Ther. Feb;1(1):34-36 Abstract (1999).

Frydman et al., "Folding of nascent polypeptide chains in a high molecular mass assembly with molecular chaperones," Nature, 370:111-117 (1994).

Galloway, D.A., "Papillomavirus vaccines in clinical trials," Lancet Infect. Dis., 3(8):469-475 (2003).

Gao et al., "Immune response to human papillomavirus type 16 E6 gene in a live vaccinia vector," Journal of General Virology, 75:157-164 (1994).

Gavarasana et al., "Prevention of Carcinoma of Cervix with Human Papillomavirus Vaccine," Indian Journal of Cancer, 37:57-66 (2000).

Geissler et al., "Enhancement of Cellular and Humoral Immune Responses to Hepatitis C Virus Protein Using DNA Based Vaccines Augmented with Cytokine-Expressing Plasmids," The Journal of Immunology, 158(3):1231-1237 (1997).

Georgopoulos et al., "Role of the Major Heat Shock Proteins as Molecular Chaperones," Annu. Rev. Cell. Bio., 9:601-634 (1993).

Goletz et al., "Delivery of Antigens to the MHC Class I Pathway Using Bacterial Toxins," Human Immunology, 54:129-136 (1997).

Grandis et al., "Head and Neck Cancer: Meeting Summary and Research Opportunities," Cancer Research, 64:8126-8129 (2004).

Graner et al., "Immunoprotective Activities of Multiple Chaperone Proteins Isolated from Murine B-Cell Leukemia/Lymphoma," Clinical Cancer Research, 6:909-915 (2000).

Haas et al., "cDNA cloning of the immunoglobulin heavy chain binding protein," Proc. Natl. Acad. Sci. USA, 85:2250-2254 (1988).

Hannum et al., "Ligand for FLT3/FLK2 Receptor Tyrosine Kinase Regulates Growth of Haematopoietic Stem Cells and is Encoded by Variant RNAs," Nature 368:643-8 (1994).

Hansen et al., "Structural features of MHC class I molecules that might facilitate alternative pathways of presentation," Immunology Today, 21(2):83-88 (2000).

Hartl, F., "Molecular chaperones in cellular protein folding," Nature, 381:571-579 (1996).

Hasan et al., "Nucleic acid immunization: concepts and techniques associated with third generation vaccines," Journal of Immunological Methods, 229:1-22 (1999).

Hauser et al., "Secretory heat-shock protein as a dendritic cell-targeting molecule: a new strategy to enhance the potency of genetic vaccines," Gene Therapy, 11:924-932 (2004.

He et al., "Viral Recombinant Vaccines to the E6 and E7 Antigens of HPV-16," Virology, 270:146-161 (2000).

Heikema et al., "Generation of heat shock protein-based vaccines by intracellular loading of gp96 with antigen peptides," Immunology Letters, 57(1-3):69-74 (1997).

Hendrick et al., "Molecular chaperone functions of heat-shock proteins," Annu. Rev. Biochem., 62:349-384 (1993).

Higgins et al., "Fast and Sensitive Multiple Sequence Alignments on a Microcomputer," Comput. Appl. Biosci. 5(2):151-153 (1989).

Hokey et al., "DNA vaccines for HIV: challenges and opportunities," Springer Semin. Immunopathol., 28(3):267-279 (2006).

Hope et al., "Flt-3 Ligand in Combination with Bovine Granulocyte-Macrophage Colony-Stimulating Factor and Interleukin-4, Promotes the Growth of Bovine Bone Marrow Derived Dendritic Cells," Scand. J. Immunol., 51:60-66 (2000).

Huang, Q. et al., "In Vivo Cytotoxic T Lymphocyte Elicitation by Mycobacterial Heat Shock Protein 70 Fusion Proteins Maps to a Discrete Domain and Is CD4+ T Cell Independent," J. Exp. Med., 191(2):403-408 (2000).

Hung et al., "Control of mesothelin-expressing ovarian cancer using adoptive transfer of mesothelin peptide-specific CD8+ T cells," Gene Therapy, 14(12):921-929 (2007).

Hung et al., "Improving vaccine potency through intercellular spreading and enhanced MHC class I presentation of antigen," J. Immunology, 166(9):5733-5740 (2001).

Hunt et al., "Characterization and sequence of a mouse hsp70 gene and its expression in mouse cell lines," Gene, 87(2):199-204 (1990).

Hunt et al., "Conserved features of eukaryotic hsp70 genes revealed by comparison with the nucleotide sequence of human hsp70," Proc. Natl. Acad. Sci. USA, 82:6455-6459 (1985).

Indraccolo et al., "Generation of expression plasmids for angiostatin, endostatin and TIMP-2 for cancer gene therapy," Int. J. Biological Markers, 14(4):251-256 (1999) (Abstract).

Iwasaki et al., "Enhanced CTL Responses Mediated by Plasmid DNA Immunogens Encoding Costimulatory Molecules and Cytokines," The Journal of Immunology, 158(10):4591-4601 (1997).

Jaffee et al., "Novel allogeneic granulocyte-macrophage colony-stimulating factor-secreting tumor vaccine for pancreatic cancer: a phase I trial of safety and immune activation," J. Clin. Oncol., 19(1):145-156 (2001).

Jager et al., "Simultaneous Humoral and Cellular Immune Response against Cancer-Testis Antigen NY-ESO-1: Definition of Human Histocompatibility Leukocyte Antigen (HLA)-A2-binding Peptide Epitopes," J. Exp. Med., 187:265-270 (1998).

Janetzki et al., "Generation of Tumor-Specific Cytotoxic T Lymphocytes and Memory T Cells by Immunization with Tumor-Derived Heat Shock Protein gp96," Journal of Immunotherapy, 21(4):269-276 (1998).
Jenkins et al., "Bioluminescent Imaging (BLI) to Improve and Refine Traditional Murine Models of Tumor Growth and Metastasis," Clin. Exp. Metastatis, 20(8):733-744 (2003).
Jinno et al., "Domain II Mutants of *Pseudomonas* Exotoxin Deficient in Translocation," J. Biol. Chem., 264(7):15953-15959 (1989).
Kim et al., "Co-transfection with cDNA encoding the Bcl family of anti-apoptotic proteins improves the efficiency of transfection in primary fetal neural stem cells," J. Neuroscience Methods, 117(2):153-158 (2002).
Kim et al., "Cytokine Molecular Adjuvants Modulate Immune Responses Induced by DNA Vaccine Constructs for HIV-1 and SIV," Journal of Interferon and Cytokine Research, 19(1):77-84 (1999).
King et al., "DNA vaccines with single-chain Fv fused to fragment C of tetanus toxin induce protective immunity against lymphoma and myeloma," Nature Medicine, 4(11):1281-1286 (1998).
Kita et al., "Frequent Gene Expression of Granulocyte Colony-Stimulating Factor (G-CSF) Receptor in CD7+ Surface CD3—Acute Lymphoblastic Leukaemia," Leukemia, 7(8):1184-1190 (1993).
Klinman et al., "Contribution of CpG Motifs to the Immunogenicity of DNA vaccines," The Journal of Immunology, 158(8):3635-3639 (1997).
Konen-Waisman et al., "Self and Foreign 60-Kilodalton Heat Shock Protein T Cell Epitope Peptides Serve As Immunogenic Carriers for a T Cell-Independent Sugar Antigen," J. Immunology, 154:5977-5985 (1995).
Konishi et al., "Japanese encephalitis DNA vaccine candidates expressing premembrane and envelope genes induce virus-specific memory B cells and long-lasting antibodies in swine," Virology, 268(1):49-55 (2000).
Koo et al., "The NK-1.1(−) Mouse: A Model to Study Differentiation of Murine NK Cells," J. Immunol. 125:2665-2672 (1986).
Larregina et al., "Pattern of cytokine receptors expressed by human dendritic cells migrated from dermal explants," Immunology, 91:303-313 (1997).
Lazar et al., "Transforming Growth Factor α: Mutation of Aspartic Acid 47 and Leucine 48 Results in Different Biological Activities," Mol. Cell Biol., 8(3)1247-1252 (1988).
Lee et al., "DNA inoculations with HIV-1 recombinant genomes that express cytokine genes enhance HIV-1 specific immune responses," Vaccine, 17:473-479 (1999).
Lee et al., "Optimal Induction of Hepatitis C Virus Envelope-Specific Immunity by BiCistronic Plasmid DNA Inoculation with the Granulocyte-Macrophage Colony-Stimulating Factor Gene," Journal of Virology, 72(10):8430-8436 (1998).
Lemon et al., "Subcutaneous administration of inactivated hepatitis B vaccine by automatic jet injection," J. Med. Virol., 12(2):129-136 (1983).
Li et al., "Roles of heat-shock proteins in antigen presentation and cross-presentation," Curr. Opin. Immunol., 14(1):45-51 (2002).
Lim et al., "Vaccination with an ovalbumin/interleukin-4 fusion DNA efficiently induces Th2 cell-mediated immune responses in an ovalbumin-specific manner," Arch. Pharm. Res., 1998, 21(5):537-542 (Abstract).
Liu et al., "The emerging role of IL-15 in NK-cell development," Immunology Today, 21(3):113-116 (2000).
Luke et al., "An OspA-based DNA vaccine protects mice against infection with *Borrelia burgdorferi*," J. Infect. Dis., 175(1):91-97 (1997).
Lyras and Rood, "Genetic Organization and Distribution of Tetracycline Resistance Determinants in *Clostridium perfringens*," Antimicrobial Agents and Chemotherapy 40:2500-2504 (1996).
Maecker et al., "DNA vaccination with cytokine fusion constructs biases the immune response to ovalbumin," Vaccine, 15(15):1687-1696 (Abstract) (1997).
Maki et al., "Human homologue of murine tumor rejection antigen pg96: 5'-Regulatory and coding regions and relationship to stress-induced proteins," Proc. Natl. Acad. Sci. USA, 87:5658-5662 (1990).
Maraskovsky et al., "Dramatic Increase in the Numbers of Funtionally Mature Dendritic Cells in Flt-3 Ligand-treated Mice: Multiple Dendritie Cell Subpopulations Identified," J. Exp. Med., 184:1953-1962 (1996).
Massa et al., "Enhanced Efficacy of Tumor Cell Vaccines Transfected with Secretable hsp70," Cancer Research, 64:1502-1508 (2004).
McKenzie et al., "Sequence and Immunogenicity of the 70-kDa Heat Shock Protein of Mycobacterium leprae," J. Immunol., 147(1):312-319 (1991).
Meinkoth et al., "Hybridization of nucleic acids immobilized on solid supports," Anal. Biochem., 138(2):267-284 (1984).
Meneguzzi et al., "Immunization against Human Papillomavirus Type 16 Tumor Cells with Recombinant Vaccinia Viruses Expressing E6 and E7," Virology, 181:62-69 (1991).
Michel, N., et al., "Enhanced Immunogenicity of HPV 16 E7 Fusion Proteins in DNA Vaccination," Virology, 294:47-59 (2002) XP002201708.
Michel, N. et al., "Improved Immunogenicity of Human Papillomavirus Type 16 E7 DNA After Fusion to the Herpes Simplex Virus 1 VP22 Gene"; Barcelona, Spain, Jul. 23-28, 2000, Abstract, 458, XP002201712.
Mikayama et al., "Molecular cloning and functional expression of a cDNA encoding glycosylation-inhibiting factor," PNAS, 90:10056-10060 (1993).
Molinari and Helenius, "Chaperone Selection During Glycoprotein Translocation into the Endoplasmic Reticulum," Science, 288(5464):331 (2000).
More et al., "Activation of cytotoxic T cells in vitro by recombinant gp96 fusion proteins irrespective of the 'fused' antigenic peptide sequence," Immunol. Lett., 69(2):275-282 (1999).
Mrsny et al., "Mucosal administration of a chimera composed of Pseudomonas exotoxin and the gp120 loop sequence of HIV-1 induces both salivary and serum antibody responses," Vaccine, 17;1425-1433 (1999).
Nguyen et al., "A Mutant of Human Papillomavirus Type 16 E6 Deficient in Bindong α-Helix Partners Displays Reduced Oncogenic Potential in Vivo," Journal of Virology, 76(24):13039-13048 (2002).
Noessner et al., "Tumor-Derived Heat Shock Protein 70 Peptide Complexes Are Cross-Presented by Human Dendritic Cells," The Journal of Immunology, 169:5424-5432 (2002).
Ohtsuka, K., "Cloning of a cDNA for heat-shock protein hsp40, a human homologue of bacterial DnaJ," Biochem. Biophys. Res. Commun., 197(1):235-240 (1993).
Okada et al., "Intranasal Immunization of a DNA Vaccine with IL-12- and Granulocyte-Macrophage Colony-Stimulating Factor (GM-CSF)-Expressing Plasmids in Lipsomes Induces Strong Mucosal and Cell Mediated Immune Responses Against HIV-1 Antigens," The Journal of Immunology, 159(7):3638-3647 (1997).
Operschall et al., "Enhanced protection against viral infection by co-administration of plasmid DNA coding for viral antigen and cytokines in mice," Journal of Clinical Virology, 13:17-27 (1999).
Ozols, RF., "Systemic therapy for ovarian cancer: current status and new treatments," Semin. Oncol., 33:53-11 (2006).
Pan et al., "A recombinant Listeria Monocylogenes Vaccine Expressing a Model Tumour Antigen Protects Mice Against Lethal Tumour Cell Challenge and Causes Regression of Established Tumours," Nature Medicine, 1(5):471-7 (1995).
Pan et al., "Regression of Established Tumors in Mice Mediated by the Oral Administration of a Recombinant Listeria monocytogenes Vaccine," Cancer Research, 55(21):4776-4779 (1995).
Pardoll et al., "Exposing the Immunology of Naked DNA Vaccines," Immunity, 3:165-169 (1995).
Pejawar-Gaddy et al., "Cancer vaccines: accomplishments and challenges," Crit. Rev. Oncol. Hematol., 67(2):93-102 (2008).
Peng et al., "Efficient delivery of DNA vaccines using human papillomavirus pseudovirions," Gene Therapy, 17(12):1453-1464 (2010).
Peoples et al., "Vaccine Implications of Folate Binding Protein, a Novel Cytotoxic T Lymphocyte-recognized Antigen System in Epithelial Cancers," Clinical Cancer Research, 5:4214-4223 (1999).
Pfisterer et al., "Management of platinum-sensitive recurrent ovarian cancer," Semin. Oncol., 33:512-516 (2006).

Przepiorka et al., "Heat shock protein peptide complexes as Immunotherapy for human cancer," Molecular Medicine Today (Reviews), 4(11):478-484 (1998).
Ray et al., "Apoptosis Induction in Prostate Cancer Cells and Xenografts by Combined Treatment with APO2 Ligand/Tumor Necrosis Factor-related apoptosis-inducing Ligand and CPT-11," Cancer Research, 63:4713-4723 (2003).
Robinson et al., "DNA Vaccines," Seminars in Immunology, 9(5):271-283 (1997).
Roby et al., "Development of a syngeneic mouse model for events related to ovarian cancer," Carcinogenesis, 21(4):585-591 (2000).
Rodriguez et al., "DNA Immunization with Minigenes: Low Frequency of Memory Cytotoxic T Lymphocytes and Inefficient Antiviral Protection Are Rectified by Ubiquitination," Journal of Virology, 72(6):5174-5181 (1998).
Rogers et al., "Multistage Multiantigen Heterologous Prime Boost Vaccine for *Plasmodium knowlesi* Malaria Provides Partial Protection in Rhesus Macaques," Infection and Immunity, 69(9):5565-5572 (2001).
Rouse et al., "Induction in Vitro of Primary Cytotoxic T-Lymphocyte Responses with DNA Encoding Herpes Simplex Virus Proteins," Journal of Virology, 68(9):5685-5689 (1994).
Sanchez-Perez et al., "Killing of Normal Melanocytes, Combined with Heat Shock Protein 70 and CD40L Expression, Cures Large Established Melanomas," The Journal of Immunology, 177:4168-4177 (2006).
Sarmiento et al., "IgCx or IgM Monoclonal Antibodies Reactive with Different Determinants of the Molecular Complex Bearing LYT 2 Antigen Block T Cell Mediated Cytolysis in the Absence of Complement," J. Immunol., 125(6):2665-2672 (1980).
Sasaki et al., "Adjuvant formulations and delivery systems for DNA vaccines," Methods, 31(3):243-254 (2003).
Schultes et al., "Monitoring of immune responses to CA125 with IFN-gamma ELISOT assay," J. Immunol. Methods, 279:1-15 (2003).
Schutze-Redeimeier et al., "Introduction of Exogenous Antigens into the MHC Class I Processing and Presentation Pathway by *Drosophila* Antennapedia Homeodomain Primes Cytotoxic T Cells in Vivo," Journal of Immunology 157:650-655 (1996).
Serody et al., "T Cell Activity After Dendritic Cell Vaccination Is Dependent on Both the Type of Antigen and the Mode of Delivery," J. Immunology, 164(9):4961-4967 (2000).
Sheikh et al., "Guns, genes, and spleen: a coming of age for rational vaccine design," Methods, 31(3):183-192 (2003).
Sin et al., "Enhancement of protective humoral (Th2) and cell mediated (Th1) immune responses against herpes simplex virus-2 codelivery of granulocyte-macrophage colony-stimulating factor expression cassettes," Eur. J. Immunol., 28:3530-3540 (1998).
Sin, J.I., "Human papillomavirus vaccines for the treatment of cervical cancer," Expert Review Vaccines, 5(6):783-792 (2006).
Smahel et al., "DNA vaccine against oncogenic hamster cells transformed by HPV16 E6/E7 oncogenes and the activated *ras* oncogene," Oncology Reports, 6:211-215 (1999).
Smahel et al., "Immunisation with modified HPV16 E7 genes against mouse oncogenic TC-1 cell sublines with downregulated expression of MHC class I molecules," Vaccine, 21:1125-1136 (2003).
Srivastava et al., "Evidence for Peptide-Chaperoning by the Endoplasmic Reticular Heat Shock Protein GP96: Implications for Vaccination Against Cancer and Infectious Diseases," J. Cell. Biochem. Suppl. 17D:94 (Abstract NZ 014) (1993).
Srivastava et al., "Heat Shock Proteins Come of Age: Primitive Functions Acquire New Roles in an Adaptive World," Immunity, 8:657-665 (1998).
Srivastava, P., "Interaction of heat shock proteins with peptides and antigen presenting cells: chaperoning of the innate and adaptive immune responses," Annu. Rev. Immunol., 20:395-425 (2002).
Srivastava et al., "5'-Structural analysis of genes encoding polymorphic antigens of chemically induced tumors," Proc. Natl. Acad. Sci. USA, 84:3807-3811 (1987).
Srivastava et al., "The Serologically Unique Cell Surface Antigen of Zajdela Ascitic Heptoma is also its Tumor-Associated Transplantation Antigen," Int. J. Cancer, 33:417-422 (1984).
Srivastava et al., "Tumor rejection antigens of chemically induced sarcomas of inbred mice," Proc. Natl. Acad. Sci. USA, 83:3407-3411 (1986).
Steinman et al., "The Sensitization Phase of T-Cell-mediated Immunity," Annals of The New York Academy of Sciences, 546:80-90 (1988).
Stevenson et al., "Idiotypic DNA Vaccines Against B-cell Lymphoma," Immunological Reviews, 145:211-228 (1995).
Suto et al., "A Mechanism for the Specific Immunagenicity of Heat Shock Protein-Chaperoned Peptides," Science, 269:1585-1588 (1995).
Suzue et al., "Adjuvant-Free HSP70 Fusion Protein System Elicits Humoral and Cellular Immune Responses to HIV-1," Journal of Immunology 156:873-879 (1996).
Suzue et al., "Heat shock fusion proteins as vehicles for antigen delivery into the major histocompatibility complex class I presentation pathway," Proc. Natl. Acad. Sci. USA 94:13146-13151 (1997).
Syrengelas et al., "DNA immunization induces protective immunity against B-cell lymphoma," Nature Medicine, 2(9):1038-1041 (1996).
Szymczak et al., "Correction of multi-gene deficiency in vivo using a single 'self-cleaving' 2A peptide-based retroviral vector," Nat. Biotechnol., 22(5):589-594 (2004).
Tamura et al., "Immunotherapy of Tumors with Autologous Tumor-Derived Heat Shock Protein Preparations," Science, 278:117-120 (1997).
Theriault et al., "Extracellular HSP70 binding to surface receptors present on antigen presenting cells and endothelial/epithelial cells," FEBS Lett., 579(9):1951-1960 (2005).
Thomas et al., "Mesothelin-specific CD8+ T Cell Responses Provide Evidence of In Vivo Cross-Priming by Antigen-Presenting Cells in Vaccinated Pancreatic Cancer Patients," J. Exp. Med., 200(3):297-306 (2004).
Ting et al., "Human gene encoding the 78,000-dalton glucose-regulated protein and its pseudogene: structure, conservation, and regulation," DNA, 7(4):275-286 (1988).
Tobery et al., "Targeting of HIV-1 antigen for rapid intracellular degradation enhances cytotoxic T lymphocyte (CTL) recognition and the induction of De Novo CTL responses in Vivo after immunization," J. Exp. Med., 185(5):909-920 (1997).
Tseng et al., "Systemic tumor targeting and killing by Sindbis viral vectors," Nature Biotechnology, 22(1):70-77 (2004).
Tseng et al., "Using Sindbis Viral Vectors for Specific Detection and Suppressin of Advanced Ovarian Cancer in Animal Models," Cancer Research, 64:6684-6692 (2004).
Tuting et al., "Autologous Human Monocyte-Derived Dendritic Cells Genetically Modified to Express Melanoma Antigens Elicit Primary Cytotoxic T Cell Responses In Vitro: Enhancement by Cotransfection of Genes Encoding the Th1-Biasing Cytokines IL-12 and IFN-$\alpha^1$," Journal of Immunology 160:1139-1147 (1996).
Udono et al., "Cellular requirements for tumor-specific immunity elicited by hear shock proteins: Tumor rejection antigen gp96 primes CD8+ T cells in vivo," Proc. Natl. Acad. Sci. USA, 91:3077-3081 (1994).
Udono et al., "Comparison of Tumor specific immunogenicities of stress-induced proteins gp96, hsp90, and hsp70'," The Journal of Immunology, 152(11):5398-5403 (1994).
Udono et al., "Heat Shock Protein 70-associated Peptides Elicit Specific Cancer Immunity," J. Exp. Med., 178:1391-1396 (1993).
Ulmer et al., "Presentation of an exogenous antigen by major histocompatibility complex class I molecules," Eur. J. Immunol., 24:1590-1596 (1994).
van Bergen et al., "Superior Tumor Protection Induced by a Cellular Vaccine Carrying a Tumor-specific T Helper Epitope by Genetic Exchange of the Class II-associated Invariant Chain Peptide," Cancer Research, 60(22):6427-6433 (2000).
van Tienhoven et al., "Induction of antigen specific CD4 + T cell responses by invariant chain based DNA vaccines," Vaccine, 19:1515-1519 (2001).
Wang et al., "CD40 is a Cellular Receptor Mediating Mycobacterial Heat Shock Protein 70 Stimulation of CC-Chemokines," Immunity, 15:971-983 (2001).

Wang et al., "A Single Amino Acid Determines Lysophospholipid Specificity of the SiP₁ (EDG1) and LPA₁ (EDG2) Phospholipid Growth Factor Receptors," The Journal of Biological Chemistry, 276(52):49213-49220 (2001).

Weiss et al., "A plasmid encoding murine granulocyte-macrophage colony-stimulating factor increases protection conferred by a malaria DNA vaccine," The Journal of Immunology, 161(5):2325-2332 (1998).

Whisstock et al., "Prediction of protein function from protein sequence and structure," Quarterly Reviews of Biophysics, 3:307-340 (2003).

Whittall et al., "Interaction between the CCR5 chemokine receptors and microbial HSP70," Eur. J. Immunol., 36(9):2304-2314 (2006).

Yokokawa et al., "Identification of Novel Human CTL Epitopes and Their Agonist Epitopes of Mesotheliin," Clin. Cancer Res., 11(17):6342-6351 (2005).

International Search Report dated Mar. 25, 2005 from PCT/US04/05292.

International Search Report dated Oct. 15, 2001 from PCT/US2000/41422.

International Search Report dated Nov. 13, 2007 from PCT/US2003/10235.

International Search Report dated Dec. 3, 2002 from PCT/US2001/24134.

International Search Report dated Sep. 20, 2002 from PCT/US2002/02596.

International Search Report dated Jun. 28, 2002 from PCT/US2001/23966.

International Search Report dated Apr. 1, 2005 from PCT/US2004/13756.

International Search Report dated Jul. 7, 2008 from PCT/US2005/47200.

International Search Report dated Mar. 22, 2007 from PCT/US2006/02707.

International Search Report dated Aug. 13, 2008 from PCT/US2007/76525.

Supplementary EP Search Report dated Mar. 6, 2006 from EP 02707618.

Supplementary EP Search Report dated Sep. 28, 2006 from EP 04751244.

Supplementary EP Search Report dated May 30, 2008 from EP 06 73 3904.

Koch et al., "Hijacking a chaperone: manipulation of the MHC class II presentation pathway," Immunology Today, 21(11):546-550 (2000).

van der Burg et al., "Pre-clinical safety and efficacy of TA-CIN, a recombinant HPV16 L2E6E7 fusion protein vaccine, in homologous and heterologus prime-boost regimens," Vaccine, 19:3652-3660 (2001).

Basu et al., "Calreticulin, A Peptide-Binding Chaperone of the Endoplasmic Reticulum, Elicits Tumor- and Peptide-Specific Immunity," Journal of Experimental Medicine, 189(5):797-802 (1999).

Bennett et al., "Calnexin Association Is Not Sufficient to Protect T Cell Receptor α Proteins from Rapid Degradation in CD4+CD8+ Thymocytes," The Journal of Biological Chemistry 273(37):23674-23680 (1998).

Cavill et al., "Generation of a Monoclonal Antibody Against Human Calreticulin by Immunization with a Recombinant Calreticulin Fusion Protein: Application in Paraffin-Embedded Sections," Appl. Immunohistochemistry & Molecular Morphology 7(2):150-155 (1999).

Chang, C-L. et al., "Control of human mesothelin-expressing tumors by DNA vaccines." Gene Therapy 1-10 (2007).

Chavin, K. et al.; "Obesity Induces Expression of Uncoupling Protein-2 in Hepatocytes and Promoates Liver ATP Depletion." J. Biol. Chem. 274(9):5692-5700 (1999).

Chen, C-H. et al. "Enhancement of DNA Vaccine Potency by Linkage of Antigen Gene to an HSP70 Gene." Cancer Research 60:1035-1042 (2000).

Chen, C-H. et al. "Recombinant DNA vaccines protect against tumors that are resistant to recombinant vaccinia vaccines containing the same gene." Gene Therapy 8:128-138 (2001).

Chen, C-H, et al., "Gene gun-mediated DNA vaccination induces antitumor immunity against human papillomavirus type 16 E7-expressing murine tumor metastases in the liver and lungs," Gene Therapy 6:1972-1981 (1999).

Chen, C-H. et al., "Boosting with recombinant vaccinia increases HPV-16 E7-specific T cell precursor frequencies of HPV-16 E7-expressing DNA vaccines," Vaccine 18:2015-2022 (2000).

Chen, C-H. et al., "Antigen-specific immunotherapy for human papillomavirus 16 E7-expressing tumors grown in the liver." Journal of Hepatology 33:91-98 (2000).

Chen et al., "Enhancement of DNA Vaccine Potency by Linkage of Antigen Gene to ANHSP70 Gene," Cancer Research, American Association for Cancer Research, 60:1035-1042 (2000).

Cheng, W-F. et al., "Cancer Immunotherapy Using Sindbis Virus Replicon Particles Encoding a VP22-Antigen Fusion." Human Gene Therapy. 13:553-568 (2002).

Cheng, W.F., et al.; Characterization of DNA Vaccines Encoding the Domains of Calreticulin for Their Ability to Elicit Tumor-Specific Immunity and Antiangiogenesis Vaccine (2005) 23:3864-3874.

Cheng, W-F. et al. "Enhancement of Sindbis Virus Self-Replicating RNA Vaccine Potency by Linkage of Herpes Simplex Virus Type 1 VP22 Protein to Antigen." Journal of Virology, 75(5): 2368-2376 (2001).

Cheng, W-F. et al. "Enhancement of Sindbis Virus Self-Replicating RNA Vaccine Potency by Linkage of Mycobacterium tuberculosis Heat Shock Protein 70 Gene to an Antigen Gene," Journal of Immunology, 166:6218-6226 (2001).

Cheng, W-F. et al., "Tumor-specific immunity and antiangiogenesis generated by a DNA vaccine encoding calreticulin linked to a tumor antigen," J. Clin. Invest. 108:669-678 (2001).

Cheng, W-F. et al., "Enhancement of Sindbis Virus Self-Replicating RNA Vaccine Potency by Targeting Antigen to Endosomal/Lysosomal Compartments." Human Gene Therapy 12:235-252 (2001).

Cheng, W-F. et al., "Enhancement of Sindbis Virus Self-Replicating RNA Vaccine Potency by Linkage of Herpes Simplex Virus Type 1 VP22 Protein to Antigen," Journal of Virology, 75(5):2368-2376 (2001).

Cheng, W-F. et al., "Repeated DNA Vaccinations Elicited Qualitatively Different Cytotoxic T Lymphocytes and Improved Protective Antitumor Effects," J Biomed Sci 9:675-687 (2002).

Cheng, W. et al., "CD8+ T cells, NK cells and IFN~γ are important for control of tumor with downregulated MHC class I expression by DNA vaccination." Gene Therapy 10:1311-1320, (2003).

Devaraj, K. et al., "Development of HPV Vaccines for HPV-Associated Head and Neck Squamous Cell Carcinoma," Crit. Rev. Oral Biol. Med. 14(5):345-362, (2003).

Eggleton, P. and Llewellyn, D.H., "Pathophysiological Roles of Calreticulin in Autoimmune Disease," Scand. J. Immunol. 49:466-473 (1999).

Harris et al., "Calreticulin and Calnexin Interact with Different Protein and Glycan Determinants During the Assembly of MHC Class I," The Journal of Immunology 160:5404-5409 (1998).

Heller, J. et al., "Tetra-O-methyl Nordihydroguaiaretic Acid Induces G2 Arrest in Mammalian Cells and Exhibits Tumoricidal Activity in Vivo," Cancer Research 61:5499-5504, (2001).

Hsieh, C-J. et al., "Ehnancement of vaccinia vaccine potency by linkage of tumor antigen gene to gene encoding calreticulin." Vaccine 22:3993-4001. (2004).

Huang, C-C. et al., "HPV in Situ Hybridization With Catalyzed Signal Amplification and Polymerase Chain Reaction in Establishing Cerebellar Metastasis of a Cervical Carcinoma," Human Pathology, 30(5):587-591. (1999).

Huang, C-H, et al. "Cancer Immunotherapy using a DNA vaccine encoding a single-chain trimer of MHC class I linked to an HPV-16 E6 immunodominant CTL epitope." Gene Therapy, 12:1180-1186 (2005).

Huang, C-C. et al., "Generation of Type-Specific Probes for the Detection of Single-Copy Human Papillomavirus by a Novel In Situ Hybridization Method," Mod. Pathol. 11(10):971:977 (1998).

Hung, C-F. et al., "Cancer Immunotherapy Using a DNA Vaccine Encoding the Translocation Domain of a Bacterial Toxin Linked to a Tumor Antigen." Cancer Research 61: 3698-3703 (2001).

Hung, C-F. et al., "Enhancement of DNA Vaccine Potency by Linkage of Antigen Gene to a Gene Encoding the Extracellular Domain of Fms-like Tyrosine Kinase 3-Ligand." Cancer Research 61:1080-1088, (2001).

Hung, C-F., et al., "Improving DNA Vaccine Potency by Linking Marek's Disease Virus Type 1 VP22 to an Antigen," Journal of Virology, 76(6):2676-2682 (2002).

Hung, C-F. et al., "Improving DNA vaccine potency via modification of preofessional antigen presenting cells." Current Opinion in Molecular Therapeutics, 5(1):20-24 (2003).

Hung, C-F. et al., "Enhancing Major Histocompatibility Complex Class I Antigen Presentation by Targeting Antigen to Centrosomes," Cancer Research. 63: 2393-2398, (2003).

Hung, C-F, et al., "Control of mesothelin-expressing ovarian cancer using adoptive transfer of mesothelin peptide-specific CD8+ T cells," Gene Therapy, pp. 1-9 (2007).

Hung, C-F, et al., "DNA Vaccines Encoding Ii-PADRE Generates Potent PADRE-specific CD4+ T-Cell Immune Responses and Enhances Vaccine Potency." Mol. Ther. Jun;15(6):1211-9. (2007).

Hung, C-F. et al., Methods in Molecular Medicine, vol. 127: DNA Vaccines: Methods and Protocols: Second Edition. Edited by Saltzman et al. Humana Press Inc., Totowa, NJ, 2006.

Hung, C-F. et al. "A DNA vaccine encoding a single-chain trimer HLA-A2 linked to human mesothelin peptide generates anti-tumor effects against human mesothelin-expressing tumors." Vaccine 25:127-135 (2007).

Hung, C-F. et al., "Vaccinia virus preferentially infects and controls human and murine ovarian tumors in mice." Gene Therapy. 14:20-29 (2007).

Hsu, K-F. et al., "Enhancement of suicidal DNA vaccine potency by linking *Mycobacterium tuberculosis* heat shock protein 70 to an antigen." Gene Therapy 8, 376-383 (2001).

Ji, H et al., "Targeting Human Papillomavirus Type 16 E7 to the Endosomal/Lysosomal Compartment Enhances the Antitumor immunity of DNA Vaccines against Murine Human Papillomavirus Type 16 E7-Expressing Tumors," Human Gene Therapy 10:2727-2740 (1999).

Ji, H et al., "Antigen-Specific Immunotherapy for Murine Lung Metastatic Tumors Expressing Human Papillomavirus Type 16 E7 Oncoprotein." Int. J. Cancer. 78, 41-45 (1998).

Ji, H. et al., "Antigen-Specific Immunotherapy for Murine Lung Metastatic Tumors Expressing Human Papillomavirus Type 16 E7 Oncoprotein." Int. J. Cancer: 78:41-45 (1998).

Kadkol, S. et al., Chapter 5: In Situ Hybridization in Cancer and Normal Tissue. Methods in Molecular Biology, vol. 223: Tumor Suppressor Genes, vol. II, Edited by W. El-Deiry, Humana Press Inc., Totowa, NJ. (2003).

Kang, T. et al., "Enhancing dendritic cell vaccine potency by combining a BAK/BAX siRNA-mediated antiapoptotic strategy to prolong dendritic cell life with an intracellular strategy to target antigen to lysosomal compartments." Int. J. Cance, 120:1696-1703 (2007).

Kerbel, Robert S., "Tumor angiogenesis: past, present and the near future," Carcinogenesis 21(3):505-515 (2000).

Kim, D, et al., "Monitoring the Trafficking of Adoptively Transferred Antigen-Specific CD8-Positive T Cells In Vivo, Using Noninvasive Luminescence Imaging." Human Gene Therapy. 18: 1-14 (2007).

Kim, T. et al., Enhancing DNA vaccine potency by coadministration of DNA encoding antiapoptotic proteins. J. Clin. Invest. 112:109-117 (2003).

Kim, T. et al., "Enhancing DNA Vaccine Potency by Combining a Strategy to Prolong Dendritic Cell Life with Intracellular Targeting Strategies," The Journal of Immunology, 171:2970-2976, (2003).

Kim, T. et al., "DNA Vaccines Employing Intracellular Targeting Strategies and a Strategy to Prolong Dendritic Cell Liofe Generate a Higher Number of CD8+ Memory T Cells and Better Long-Term Antitumor Effects Compared with a DNA Prime-Vaccinia Boost Regimin." Human Gene Therapy 16:26-34 (2005).

Kim, T. et al. "Modification of Professional Antigen-Presenting Cells with Small Interfering RNA In vivo to Enhance Cancer Vaccine Potency," Cancer Res. 65(1):309-316. 2005.

Kim, T. et al., "A DNA Vaccine Co-Expressing Antigen and an Anti-Apoptotic Molecule Further Enhances the Antigen-Specific CD8+ T-Cell Immune Response." J. Biomed. Sci. 11:493-499 (2004).

Kim, T. et al., "Generation and Characterization of DNA Vaccines Targeting the Nucleocapsid Protein of Severe Acute Respiratory Syndrome Caronavirus." Journal of Virology, 78(9):4638-4645. (2004).

Kim, T. et al., "Vaccination with a DNA Vaccine Encoding Herpes Simplex Type 1 VP22 Linked to Antigen Generates Long-Term Antigen-Specific CD8-Positive memory T Cells and Protective Immunity." Human Gene Therapy. 15:167-177. (2004).

Kim, J. et al., "Comparison of HPV DNA vaccines employing intracellular targeting strategies." Gene Therapy, 11:1011-1018 (2004).

Kim, T. et al., "Enhancement of suicidal DNA vaccine potency by delaying suicidal DNA-induced cell death." Gene Therapy. 11:336-342. (2004).

Kim, T. et al., "Enhancement of DNA Vaccine Potency by Coadministration of a Tumor Antigen Gene and DNA Encoding Serine Protease Inhibitor-6." Cancer Research. 64:400-405, (2004).

Lafond-Walker, A. et al., "Inducible Nitric Oxide Synthase Expression in Coronary Arteries of Transplanted Human Hearts with Accelerated Graft Arteriosclerosis." American Journal of Pathology, 151(4): 919-925 (1997).

Leitner et al., "DNA and RNA~Based Vaccines: Principles, Progress and Prospects," Vaccine 18(9-10):765-777 (1999).

Liaw, K. et al., "Human papillomavirus and cervical neoplasia: a case-control study in Taiwan." Int. J. Cancer. 62(5):565-71 (1995).

Lin, K-Y. et al., "Ectopic Expression of Vascular Cell Adhesion Molecule-1 as a New Mechanism for Tumor Immune Evasion." Cancer. Res. 67(4) 1832-1841 (2007).

Lin, C-T. et al., "Boosting with Recombinant Vaccinia Increases HPV-16 E7-Specific T Cell Precursor Frequencies and Antitumor Effects of HPV-16 E7-Expressing Sincibis Virus Replicon Particles." Molecular Therapy. 8(4):559-566 (2003).

Lin, K-Y. et al., "Treatment of Established Tumors with a Novel Vaccine That Enhances Major Histocompatibility Class II Presentation of Tumor Antigen." Cancer Research 56:21-26 (1996).

Lin, Y-Y. et al., "Vaccines against human papillomavirus." Frontiers in Bioscience. 12:246-264 (2007).

Lin, Ken-Yu et al., "Coinfection of HPV-11 and HPV-16 in a case of Laryngeal Squamous Papillomas With severe Dysplasia," Laryngoscope. 107(7):942-947 (1997).

Ling, M. et al., "Preventive and Therapeutic Vaccines for Human Papillomavirus-Associated Cervical Cancers." J Biomed Sci 7:341-356 (2000).

Liu et al., "Recombinant Adeno-Associated Virus Expressing Human Papillomavirus Type 16 E7 Peptide DNA Fused with Heat Shock Protein DNA as a Potential Vaccine for Cervical Cancer," Journal of Virology, 2888-2894 (2000).

McCluskie et al., "Route and Method of Delivery of DNA Vaccine Influence Immune Responses in Mice and Non-Human Primates," Mol. Med. 5:287-300 (1999).

Mao, C-P. et al., "Immunological research using RNA interference technology." Immunology, 121:295-307 (2007).

Mao, C-P. et al. "Immunotherapeutic strategies employing RNA interference technology for the control of cancers." Journal of Biomedical Science 14:15-29 (2007).

MHC Class-I Binding Peptide Prediction Results for the Maltose Binding Protein of Vector pMAL used in D8, using ProPred-I, Singh et al. Bioinformatics 2001; 17 (12):1236-37.

Mold, D. et al., "Four Classes of HERV~K Long Terminal Repeats and Their Relative Promoter Strengths for Transcription." J Biomed Sci 4:78-82 (1997).

Moniz, M. et al., "HPV DNA Vaccines," Frontiers in Bioscience 8, d55-68, (2003).

Nair et al., "Calreticulin Displays in Vivo Peptide-Binding Activity and Can Elicit CTL Responses Against Bound Peptides," Journal of Immunology 162(11):6426-5432 (1999).

Nakano et al., "Immunization with Plasmid DNA Encoding Hepatitis C Virus Envelope E2 Antigenic Domains Induces Antibodies Whose Immune Reactivity Is Linked to the Injection Mode," Journal of Virology 71:7101-7109 (1997).

Nawrocki, S. and Mackiewicz, A., "Genetically modified tumour vaccines~where we are today," Cancer Treatment Reviews 25:29-46 (1999).

Nicchitta, C.V. and Reed, R.C., "The immunological properties of endoplasmic reticulum chaperones: a conflict of interest?," Essays in Biochemistry 36:15-25 (2000).

Ockert et al., "Advances in Cancer Immunotherapy Symposium, Dresden, Germany," Immunology Today 20(2):63-65 (1999).

Pai, S I et al., "prospects of RNA interference therapy for cancer," Gene Therapy, 13:464-477 (2006).

Peng, S., et al.; "Characterization of HPV16-E6 DNA vaccines employing intracellular targeting and intercellular spreading strategies," Journal of Biomedical Science. (2005) 12:689-700.

Peng, S. et al., "HLA-DQB1*02-restricted HPV-16 E7 Peptide-Specific CD4+ T-Cell Immune Responses Correlate with Regression of HPV-16-Associated High-Grade Squamous Intraepithelial Lesions." Clin. Cancer Res. 13(8) 2479-2487 (2007).

Peng, S, et al., "A combination of DNA vaccines targeting human papillomavirus type 16 E6 and E7 generates potent antitumor effects." Gene Therapy. 13:257-265 (2006).

Peng, S. et al., "Vaccination with Dendritic Cells Transgected with BAK and BAX siRNA Enhances Antigen-Specific Immune Responses by Prolonging Dendritic Cell Life " Human Gene Therapy 16:584-593 (2005).

Peng, S. et al., "Characterization of HLA-A2-restricted HPV-16 E7-specific CD8+ T-cell immune responses induced by DNA vaccines in HLA-A2 transgenic mice." Gene Therapy. 13:67-77 (2006).

Peng, S. et al., "Development of a DNA Vaccinje targeting Human Papillomavirus Type 16 Oncoprotein E6." Journal of Virology 78(16):8468-8476. (2004).

Roden, R. et al. "The impact of preventative HPV Vaccination." Discovery Medicine. vol. 6, No. 35, pp. 175-181 (2006).

Roden, R. et al., "Vaccination to Prevent and Treat Cervical Cancer." Human Pathology. 35(8): 971-982. (2004).

Roden and Wu. "How will HPV vaccines affect cervical cancer?" Nature Reviews, vol. 6, pp. 753-763. (2006).

Shalinsky et al., "Marked Antiangiogenic and Antitumor Efficacy of AG3340 in Chemoresistant Human Non-Small Cell Lung Cancer Tumors: Single Agent and Combination Chemotherapy Studies," Clincal Cancer Research 5:1905-1917 (1999).

Tomson, T. et al. "Human papillomavirus vaccines for the prevention and treatment of cervical cancer." Current Opinion in Investigational Drugs, 5(12):1247-1261. (2004).

Torres et al., "Differential Dependence on Target Site Tissue for Gene Gun and Intramuscular DNA Immunizations," The Journal of Immunology 158:4529-4532 (1997).

Trimble C, et al., "Spontaneous Regression of High-Grade Cervical Dysplasia: Effects of Human Papillomavirus Type and HLA Phenotype." Clin. Cancer Res. 11(13):4717-4723 (2005).

Trimble, C. et al., "Comparison of the CD8+ T cell responses and antitumor effects generated by DNA vaccine administered through gen gun, biojector and syringe." Vaccine. 21:4036-4042, (2003).

Trompeter, Hans-Ingo et al., "Variable Nuclear Cytoplasmic Distribution of the 11.5-kDa Zinc-binding Protein (Parathymosin-α) and Identification of a Bipartite Nuclear Localization Signal," The Journal of Biological Chemistry 271(2):1187-1193 (1996).

Ramos-Soriano, A. et al., "Enteric pathogens associated with gastrointestinal dysfunction in children with HIV infection." Molecular and Cellular Probes 10, 67-73 (1996).

Rashid, A. et al., "Mitochondrial Proteins That Regulate Apoptosis and Necrosis Are Induced in Mouse Fatty Liver." Hepatology 29:1131-1138 (1999).

Trujillo, J. et al., "Characterization of human papillomavirus type 57b: transforming activity and comparative sequence analysis as probes for biological determinants associated with high-risk oncogenic viruses." Virus genes. 12(2):165-78 (1996).

Tsen, S-W. et al., "Enhancing DNA Vaccine Potency by Modifying the Properties of Antigen-Presenting Cells.", Expert Rev Vaccine 2007;6:227-239.

Vu, K. et al., "Cellular Proliferation, Estrogen Receptor, Progesterone Receptor, and bcl-2 Expression in GnRH Agonist-Treated Uterine Leiomyomas." Human Pathology 29:359-363 (1998).

Wang, T-L. et al., "Intramuscular administration of E7-transfected dendritic cells generates the most potent E7-specific anti-tumor immunity." Gene Therapy 7, 726-733 (2000).

Wu, T-C, et al., "Engineering an intracellular pathway for major histocompatibility complex class II presentation of antigens." Proc. Natl. Acad. Sci. 92:11671-11675 (1995).

Wu, T-C. "Therapeutic human papillomavirus DNA vaccination strategies to control cervical cancer." European Journal of immunology. 37:310-314 (2007).

Wu, T-C. et al., "A Reassessment of the Role of B7-1 Expression in Tumor Rejection." J. Exp. Med. 182:1415-1421 (1995).

Wu, T-C. et al., "Demonstration of human papillomavirus (HPV) genomic amplification and viral-like particles from CaSki cell line in SCID mice." Journal of Virological Methods 65:287-298 (1997).

Wu, T-C. et al., "Detection of the Human Cytomegalovirus 2.0-kb immediate Early Gene I Transcripts in Permissive and Nonpermissive Infections by RNA in situ Hybridization." J Biomed Sci 4:19-27 (1997).

Yen, M. et al., "Diffuse Mesothelin Expression Correlates with Prolonged Patient Survival in Ovarian Serous Carcinoma." Clin. Cancer. Res. 12(3) 827-831 (2006).

N.R. Chu, H.B. Wu, T.-C. Wu, L.J. Boux, M.I. Siegel and L.A. Mizzen Immunotherapy of a human papillomavirus (HPV) type 16 E7-expressing tumor by administration of a fusion protein comprising *Mycobacterium bovis* Bacille Calmette-Guerin (BCG) hsp65 and HPV-16 E7. Clin. Exp. Immunol. 121: 216-225 (2000).

Oltersdorf et al., "Identification of Human Papillomavirus Type 16 E7 Protein by Monoclonal Antibodies," J. Gen. Virol., 68:2933-2938 (1987).

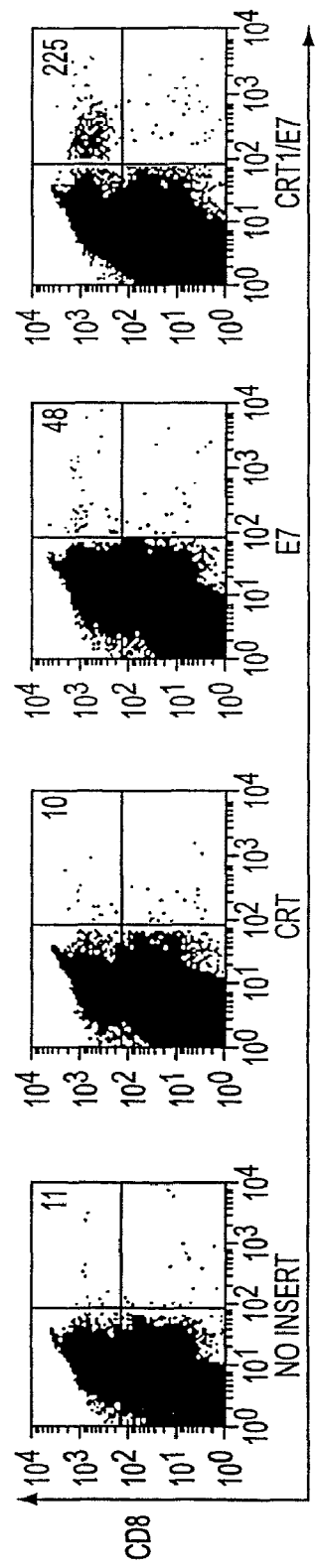
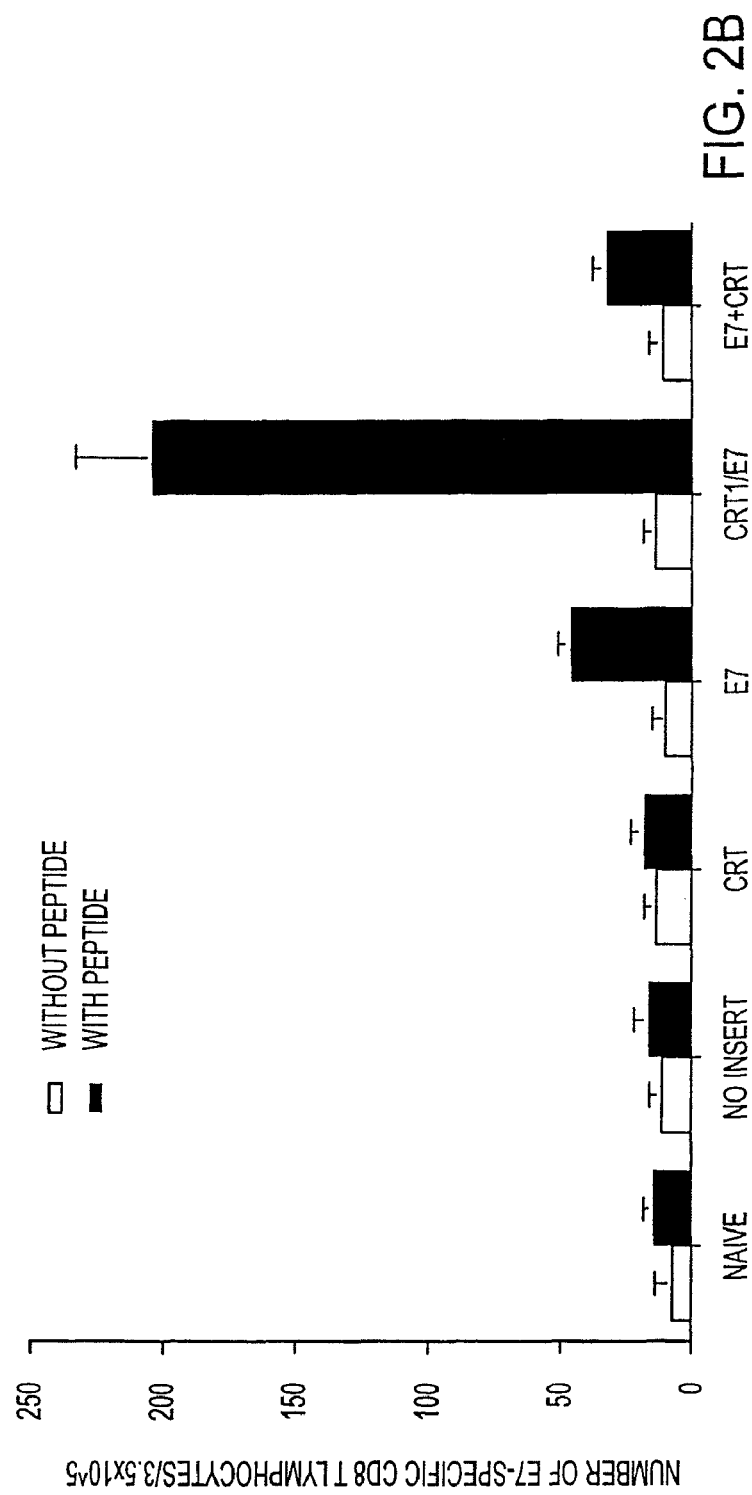
FIG. 2
FIG. 2B

DNA CONSTRUCTS
SINrep5
SINrep5-HSP70
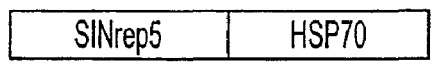
SINrep5-E7
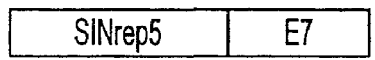
SIN5rep5-E7/HSP70
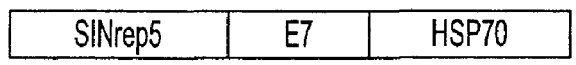
RNA TRANSCRIPTS
SINrep5
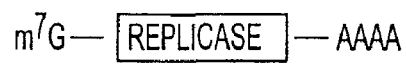
SINrep5-HSP70
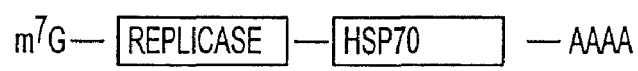
SINrep5-E7
SIN5rep5-E7/HSP70
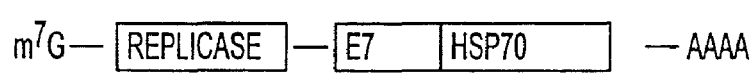
FIG. 9

SEQUENCE LISTING

```
<160> NUMBER OF SEQ ID NOS: 7

<210> SEQ ID NO 1
<211> LENGTH: 1899
<212> TYPE: DNA
<213> ORGANISM: Homo sapiens
<220> FEATURE:
<221> NAME/KEY: CDS
<222> LOCATION: (69)..(1319)
<223> OTHER INFORMATION:

<400> SEQUENCE: 1
gtccgtactg cagagccgct gccggagggt cgttttaaag ggccgcgttg ccgcccctc      60 ggcccgcc atg ctg cta tcc gtg ccg ctg ctc ggc ctc ctc ggc ctg         110
         Met Leu Leu Ser Val Pro Leu Leu Gly Leu Leu Gly Leu
         1               5                   10 gcc gtc gcc gag ccc gcc gtc tac ttc aag gag cag ttt ctg gac gga     158
Ala Val Ala Glu Pro Ala Val Tyr Phe Lys Glu Gln Phe Leu Asp Gly
15              20                  25                  30 gac ggg tgg act tcc cgc tgg atc gaa tcc aaa cac aag tca gat ttt     206
Asp Gly Trp Thr Ser Arg Trp Ile Glu Ser Lys His Lys Ser Asp Phe
                35                  40                  45 ggc aaa ttc gtt ctc agt tcc ggc aag ttc tac ggt gac gag gag aaa     254
Gly Lys Phe Val Leu Ser Ser Gly Lys Phe Tyr Gly Asp Glu Glu Lys
            50                  55                  60 gat aaa ggt ttg cag aca agc cag gat gca cgc ttt tat gct ctg tcg     302
Asp Lys Gly Leu Gln Thr Ser Gln Asp Ala Arg Phe Tyr Ala Leu Ser
65                  70                  75 gcc agt ttc gag cct ttc agc aac aaa ggc cag acg ctg gtg gtg cag     350
Ala Ser Phe Glu Pro Phe Ser Asn Lys Gly Gln Thr Leu Val Val Gln
80                  85                  90 ttc acg gtg aaa cat gag cag aac atc gac tgt ggg ggc ggc tat gtg     398
Phe Thr Val Lys His Glu Gln Asn Ile Asp Cys Gly Gly Gly Tyr Val
95                  100                 105                 110 aag ctg ttt cct aat agt ttg gac cag aca gac atg cac gga gac tca     446
Lys Leu Phe Pro Asn Ser Leu Asp Gln Thr Asp Met His Gly Asp Ser
                115                 120                 125 gaa tac aac atc atg ttt ggt ccc gac atc tgt ggc cct ggc acc aag     494
Glu Tyr Asn Ile Met Phe Gly Pro Asp Ile Cys Gly Pro Gly Thr Lys
            130                 135                 140 aag gtt cat gtc atc ttc aac tac aag ggc aag aac gtg ctg atc aac     542
Lys Val His Val Ile Phe Asn Tyr Lys Gly Lys Asn Val Leu Ile Asn
        145                 150                 155 aag gac atc cgt tgc aag gat gat gag ttt aca cac ctg tac aca ctg     590
Lys Asp Ile Arg Cys Lys Asp Asp Glu Phe Thr His Leu Tyr Thr Leu
    160                 165                 170 att gtg cgg cca gac aac acc tat gag gtg aag att gac aac agc cag     638
Ile Val Arg Pro Asp Asn Thr Tyr Glu Val Lys Ile Asp Asn Ser Gln
175                 180                 185                 190 gtg gag tcc ggc tcc ttg gaa gac gat tgg gac ttc ctg cca ccc aag     686
```

```
                Val Glu Ser Gly Ser Leu Glu Asp Asp Trp Asp Phe Leu Pro Pro Lys
                                195                 200                 205 aag ata aag gat cct gat gct tca aaa ccg gaa gac tgg gat gag cgg      734
Lys Ile Lys Asp Pro Asp Ala Ser Lys Pro Glu Asp Trp Asp Glu Arg
            210                 215                 220 gcc aag atc gat gat ccc aca gac tcc aag cct gag gac tgg gac aag      782
Ala Lys Ile Asp Asp Pro Thr Asp Ser Lys Pro Glu Asp Trp Asp Lys
225                 230                 235 ccc gag cat atc cct gac cct gat gct aag aag ccc gag gac tgg gat      830
Pro Glu His Ile Pro Asp Pro Asp Ala Lys Lys Pro Glu Asp Trp Asp
        240                 245                 250 gaa gag atg gac gga gag tgg gaa ccc cca gtg att cag aac cct gag      878
Glu Glu Met Asp Gly Glu Trp Glu Pro Pro Val Ile Gln Asn Pro Glu
255                 260                 265                 270 tac aag ggt gag tgg aag ccc cgg cag atc gac aac cca gat tac aag      926
Tyr Lys Gly Glu Trp Lys Pro Arg Gln Ile Asp Asn Pro Asp Tyr Lys
                275                 280                 285 ggc act tgg atc cac cca gaa att gac aac ccc gag tat tct ccc gat      974
Gly Thr Trp Ile His Pro Glu Ile Asp Asn Pro Glu Tyr Ser Pro Asp
            290                 295                 300 ccc agt atc tat gcc tat gat aac ttt ggc gtg ctg ggc ctg gac ctc     1022
Pro Ser Ile Tyr Ala Tyr Asp Asn Phe Gly Val Leu Gly Leu Asp Leu
        305                 310                 315 tgg cag gtc aag tct ggc acc atc ttt gac aac ttc ctc atc acc aac     1070
Trp Gln Val Lys Ser Gly Thr Ile Phe Asp Asn Phe Leu Ile Thr Asn
320                 325                 330 gat gag gca tac gct gag gag ttt ggc aac gag acg tgg ggc gta aca     1118
Asp Glu Ala Tyr Ala Glu Glu Phe Gly Asn Glu Thr Trp Gly Val Thr
335                 340                 345                 350 aag gca gca gag aaa caa atg aag gac aaa cag gac gag gag cag agg     1166
Lys Ala Ala Glu Lys Gln Met Lys Asp Lys Gln Asp Glu Glu Gln Arg
                355                 360                 365 ctt aag gag gag gaa gac aag aaa cgc aaa gag gag gag gag gca         1214
Leu Lys Glu Glu Glu Asp Lys Lys Arg Lys Glu Glu Glu Glu Ala
            370                 375                 380 gag gac aag gag gat gat gag gac aaa gat gag gat gag gag gat gag     1262
Glu Asp Lys Glu Asp Asp Glu Asp Lys Asp Glu Asp Glu Glu Asp Glu
        385                 390                 395 gag gac aag gag gaa gat gag gag gaa gat gtc ccc ggc cag gcc aag     1310
Glu Asp Lys Glu Glu Asp Glu Glu Glu Asp Val Pro Gly Gln Ala Lys
400                 405                 410 gac gag ctg tagagaggcc tgcctccagg gctggactga ggcctgagcg             1359
Asp Glu Leu
415 ctcctgccgc agagcttgcc gcgccaaata atgtctctgt gagactcgag aactttcatt   1419 tttttccagg ctggttcgga tttggggtgg attttggttt tgttccctc ctccactctc    1479 ccccacccc tccccgccct tttttttttt ttttttaaac tggtatttta tcctttgatt    1539 ctccttcagc cctcaccct ggttctcatc tttcttgatc aacatctttt cttgcctctg    1599 tgcccttct ctcatctctt agctccctc caacctgggg ggcagtggtg tggagaagcc     1659 acaggcctga gatttcatct gctctccttc ctggagccca gaggagggca gcagaagggg   1719 gtggtgtctc caaccccca gcactgagga agaacggggc tcttctcatt tcacccctcc   1779 ctttctcccc tgccccagg actgggccac ttctgggtgg ggcagtgggt cccagattgg    1839 ctcacactga gaatgtaaga actacaaaca aaatttctat taaattaaat tttgtgtctc   1899
```

<210> SEQ ID NO 2
<211> LENGTH: 417

<212> TYPE: PRT
<213> ORGANISM: Homo sapiens

<400> SEQUENCE: 2

Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
                20                  25                  30

Trp Thr Ser Arg Trp Ile Glu Ser Lys His Lys Ser Asp Phe Gly Lys
            35                  40                  45

Phe Val Leu Ser Ser Gly Lys Phe Tyr Gly Asp Glu Glu Lys Asp Lys
        50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
                100                 105                 110

Phe Pro Asn Ser Leu Asp Gln Thr Asp Met His Gly Asp Ser Glu Tyr
                115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
                180                 185                 190

Ser Gly Ser Leu Glu Asp Asp Trp Asp Phe Leu Pro Pro Lys Lys Ile
            195                 200                 205

Lys Asp Pro Asp Ala Ser Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
                260                 265                 270

Gly Glu Trp Lys Pro Arg Gln Ile Asp Asn Pro Asp Tyr Lys Gly Thr
            275                 280                 285

Trp Ile His Pro Glu Ile Asp Asn Pro Glu Tyr Ser Pro Asp Pro Ser
290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
                340                 345                 350

Ala Glu Lys Gln Met Lys Asp Lys Gln Asp Glu Glu Gln Arg Leu Lys
            355                 360                 365

Glu Glu Glu Glu Asp Lys Lys Arg Lys Glu Glu Glu Glu Ala Glu Asp
                370                 375                 380

Lys Glu Asp Asp Glu Asp Lys Asp Glu Asp Glu Glu Asp Glu Glu Asp
385                 390                 395                 400

```
Lys Glu Glu Asp Glu Glu Asp Val Pro Gly Gln Ala Lys Asp Glu
            405                 410                 415

Leu

<210> SEQ ID NO 3
<211> LENGTH: 24
<212> TYPE: DNA
<213> ORGANISM: Unknown
<220> FEATURE:
<223> OTHER INFORMATION: Primer

<400> SEQUENCE: 3
ggggaattca tgagataca ccta                                            24

<210> SEQ ID NO 4
<211> LENGTH: 23
<212> TYPE: DNA
<213> ORGANISM: Unknown
<220> FEATURE:
<223> OTHER INFORMATION: Primer

<400> SEQUENCE: 4
ggtggatcct tgagaacaga tgg                                            23

<210> SEQ ID NO 5
<211> LENGTH: 98
<212> TYPE: PRT
<213> ORGANISM: Human papillomavirus

<400> SEQUENCE: 5

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 6
<211> LENGTH: 30
<212> TYPE: DNA
<213> ORGANISM: Unknown
<220> FEATURE:
<223> OTHER INFORMATION: Primer

<400> SEQUENCE: 6
ccggtctaga atgctgctcc ctgtgccgct                                     30

<210> SEQ ID NO 7
<211> LENGTH: 30
<212> TYPE: DNA
<213> ORGANISM: Unknown
<220> FEATURE:
<223> OTHER INFORMATION: Primer
```

<400> SEQUENCE: 7
ccggagatct cagctcgtcc ttggcctggc                30

MOLECULAR VACCINE LINKING AN ENDOPLASMIC RETICULUM CHAPERONE POLYPEPTIDE TO AN ANTIGEN

CROSS-REFERENCE TO RELATED APPLICATIONS

This application is a continuation application of U.S. application. Ser. No. 10/343,448, filed Aug. 4, 2003, which is a U.S. National Stage Application filed under 35 U.S.C. §371 based on PCT/US01/24134, filed on Aug 2, 2001, which claims the benefit of U.S. Provisional Application No. 60/222,902, filed Aug. 3, 2000. The entire contents of each of these applications are incorporated herein by reference in their entirety.

STATEMENT AS TO FEDERALLY SPONSORED RESEARCH

This invention was made with Federal Government support under grants from National Institutes of Health; RO1 CA72631; from the NCDDG, RFA CA-95-020. The United States government may have certain rights in the invention.

BACKGROUND OF THE INVENTION

1. Field of the Invention

This invention, in the field of immunology and medicine, provides compositions and methods for inducing enhanced antigen-specific immune responses, particularly those mediated by cytotoxic T lymphocytes (CTL), using chimeric or hybrid nucleic acid molecules that encode an endoplasmic reticulum chaperone polypeptide, e.g., calreticulin, and a polypeptide or peptide antigen. Naked DNA and self-replicating RNA replicon vaccines are provided.

2. Description of the Background Art

DNA vaccines have become an attractive approach for inducing antigen-specific immunotherapy. Forms of DNA vaccines include "naked" DNA, such as plasmid DNA (U.S. Pat. Nos. 5,580,859; 5,589,466; 5,703,055), viral DNA, and the like. Basically, a DNA molecule encoding a desired immunogenic protein or peptide is administered to an individual and the protein is generated in vivo. Use of "naked" DNA vaccines has the advantages of being safe because, e.g., the plasmid itself has low immunogenicity, it can be easily prepared with high purity and, compared to proteins or other biological reagents, it is highly stable. However, DNA vaccines have limited potency. Several strategies have been applied to increase the potency of DNA vaccines, including, e.g., targeting antigens for rapid intracellular degradation; directing antigens to antigen presenting cells (APCs) by fusion to ligands for APC receptors; fusing antigens to chemokines or to antigenic pathogenic sequences, co-injection with cytokines or co-stimulatory molecules or adjuvant compositions.

Cancer vaccines are an attractive approach for cancer treatment because they may have the potency to eradicate systemic tumor in multiple sites in the body and the specificity to discriminate between neoplastic and non-neoplastic cells (Pardoll (1998) Nature Med. 4:525-531). Anti-tumor effects of the immune system are mainly mediated by cellular immunity. The cell-mediated component of the immune system is equipped with multiple effector mechanisms capable of eradicating tumors, and most of these anti-tumor immune responses are regulated by T cells. Therefore, it is hoped that cancer vaccines, particularly as DNA vaccines, aimed at enhancing tumor-specific T cell responses will be developed to control tumors.

HPV oncogenic proteins, E6 and E7, are co-expressed in most cervical cancers associated with HPV and are important in the induction and maintenance of cellular transformation. Therefore, vaccines targeting E6 or E7 proteins may provide an opportunity to prevent and treat HPV-associated cervical malignancies. HPV-16 E7, a well-characterized cytoplasmic/nuclear protein that is more conserved than E6 in HPV-associated cancer cells, has been exploited in a number of HPV vaccines.

Calreticulin (CRT), an abundant 46 kilodalton (kDa) protein located in the lumen of the cell's endoplasmic reticulum (ER), displays lectin activity and participates in the folding and assembly of nascent glycoproteins. See, e.g., Nash (1994) Mol. Cell. Biochem. 135:71-78; Hebert (1997) J. Cell Biol. 139:613-623; Vassilakos (1998) Biochemistry 37:3480-3490; Spiro (1996) J. Biol. Chem. 271:11588-11594. CRT associates with peptides transported into the ER by transporters that are associated with antigen processing, such as TAP-1 and TAP-2 (Spee (1997) Eur. J. Immunol. 27:2441-2449). CRT also forms complexes with peptides in vitro. Upon administration to mice, these complexes, elicited peptide-specific CD8+ T cell responses (Basu (1999) J. Exp. Med. 189:797-802; Nair (1999) J. Immunol. 162:6426-6432). CRT purified from murine tumors elicited immunity specific for the tumor from which the CRT was taken, but not for an antigenically distinct tumor (Basu, supra). By pulsing mouse dendritic cells (DCs) in vitro with a CRT-peptide complex, the peptide was re-presented by MHC class I molecules on the DCs to stimulate a peptide-specific CTL response (Nair, supra).

CRT also has anti-angiogenic effects. CRT and a fragment comprising amino acid residues 1-180, which has been called "vasostatin," are endothelial cell inhibitors that can suppress tumor growth (Pike (1999) Blood. 94:2461-2468). Tumor growth and metastasis depend on the existence of an adequate blood supply. As tumors grow larger, adequate blood supply to the tumor tissue is often ensured by new vessel formation, a process termed angiogenesis. (Folkman (1982) Ann. NY Acad. Sci. 401:212-27; Hanahan (1996) Cell. 86:353-364). Therapeutic agents that target and damage tumor vasculature can prevent or delay tumor growth and even promote regression or dormancy.

Self-replicating RNA vaccines (RNA replicons) have emerged as an important, more potent form of nucleic acid vaccines. RNA replicon vaccines may be derived from alphavirus vectors, such as Sindbis virus (Xiong (1989) Science 243:1188-1191), Semliki Forest virus (Ying (1999) Nature Med. 5:823-827), or Venezuelan equine encephalitis virus (Pushko (1997) Virology 239:389-401) vectors. These vaccines are self-replicating and self-limiting and may be administered as either RNA or DNA, which is then transcribed into RNA replicons in transfected cells or in vivo. (Berglund (1998) Nature Biotechnol. 16:562-565). Self-replicating RNA infects a diverse range of cell types and allows the expression of the antigen of interest at high levels (Huang (1996) Curr. Opin. Biotechnol. 7:531-535). Additionally, self-replicating RNA eventually causes lysis of transfected cells because viral replication is toxic to infected host cells (Frolov (1996) J. Virol. 70:1182-1190). These vectors therefore do not raise the concern associated with naked DNA vaccines of integration into the host genome. This is particularly important for vaccine development targeting proteins that are potentially oncogenic, such as the HPV E6 and E7 proteins.

Chen (2000) Cancer Research 60:1035-1042 demonstrated that linkage of human papillomavirus type 16 (HPV-16) E7 antigen to *Mycobacterium tuberculosis* heat shock protein 70 (HSP70) leads to the enhancement of DNA vaccine potency. Other studies have demonstrated that immunization with heat shock protein (HSP) complexes isolated from tumor or virus-infected cells are able to induce potent anti-tumor (Janetzki (1998) J. Immunother. 21:269-276) or antiviral immunity (Heikema (1997) Immunol. Lett. 57:69-74). Immunogenic HSP-peptide complexes can also be reconstituted in vitro by mixing the peptides with HSPs (Ciupitu (1998) J. Exp. Med. 187:685-691). HSP-based protein vaccines can also be administered by fusing antigens to HSPs (Suzue (1996) J. Immunol. 156:873-879, HSP70 fusion protein elicited humoral and cellular immune responses to HIV-1 p24). These experiments demonstrate that 1) HSP-peptide complexes derived from tumor cells or virus-infected cells can stimulate tumor or virus-specific immunity; 2) the specificity of this immune response is caused by tumor-derived peptides that are bound to HSPs and not caused by the HSPs themselves; and 3) the immune response can be induced in mice with MHC either identical or different to the MHC of donor HSPs (Przepiorka (1998) Mol. Med. Today 4:478-484; Srivastava (1998) Immunity 8:657-665). While these investigations have made HSPs more attractive for use in immunotherapy, the only HSP vaccines that have been tested thus far are in the form of protein-based vaccines or DNA-based vaccines.

SUMMARY OF THE INVENTION

The invention provides a nucleic acid encoding a chimeric protein comprising a first polypeptide domain comprising an endoplasmic reticulum chaperone polypeptide and a second polypeptide domain comprising at least one antigenic peptide. The antigenic peptide can comprise an MHC Class I-binding peptide epitope. The antigenic peptide, e.g., the MHC class I-binding peptide epitope, can be between about 8 amino acid residues and about 11 amino acid residues in length.

The endoplasmic reticulum chaperone polypeptide includes any ER polypeptide having chaperone functions similar to the exemplary chaperones calreticulin, calnexin, tapasin, or ER60 polypeptides; or, analogues or mimetics thereof, or, functional fragments thereof. Such functional fragments can be screened using routine screening tests, e.g., as described in Examples 1 and 2, below. Thus, in alternative embodiments, the endoplasmic reticulum chaperone polypeptide comprises or consists of a calnexin polypeptide or an equivalent thereof, an ER60 polypeptide or an equivalent thereof, a GRP94/GP96 or a GRP94 polypeptide or an equivalent thereof, or, a tapasin polypeptide or an equivalent thereof.

In one embodiment, the calreticulin polypeptide comprises a human calreticulin polypeptide. In alternative embodiments, the human calreticulin polypeptide sequence can comprises SEQ ID NO:1, or, it can consist essentially of a sequence from about residue 1 to about residue 180 of SEQ ID NO:1, or, it can consist essentially of a sequence from about residue 181 to about residue 417 of SEQ ID NO:1.

In one embodiment, the antigen (e.g., the MHC class I-binding peptide epitope) is derived from a pathogen, e.g., it comprises a peptide expressed by a pathogen. The pathogen can be a virus, such as, e.g., a papilloma virus, a herpesvirus, a retrovirus (e.g. an immunodeficiency virus, such as HIV-1), an adenovirus, and the like. The papilloma virus can be a human papilloma virus; for example, the antigen (e.g., the MHC Class I-binding peptide) can be derived from an HPV-16 E7 polypeptide. In one embodiment, the HPV-16 E7 polypeptide is substantially non-oncogenic, i.e., it does not bind retinoblastoma polypeptide (pRB) or binds pRB with such low affinity that the HPV-16 E7 polypeptide is effectively non-oncogenic when expressed or delivered in vivo.

In alternative embodiments, the pathogen is a bacteria, such as *Bordetella pertussis; Ehrlichia chaffeensis; Staphylococcus aureus; Toxoplasma gondii; Legionella pneumophila; Brucella suis; Salmonella enterica; Mycobacterium avium; Mycobacterium tuberculosis; Listeria monocytogenes; Chlamydia trachomatis; Chlamydia pneumoniae; Rickettsia rickettsii*; or, a fungi, such as, e.g., *Paracoccidioides brasiliensis*; or other pathogen, e.g., *Plasmodium falciparum.*

In another embodiment, the MHC class I-binding peptide epitope is derived from a tumor cell. The tumor cell-derived peptide epitope can comprise a tumor associated antigen, e.g., a tumor specific antigen, such as, e.g., a HER-2/neu antigen.

In one embodiment, the isolated or recombinant nucleic acid molecule is operatively linked to a promoter, such as, e.g., a constitutive, an inducible or a tissue-specific promoter. The promoter can be expressed in any cell, including cells of the immune system, including, e.g., antigen presenting cells (APCs), e.g., in a constitutive, an inducible or a tissue-specific manner.

In alternative embodiments, the APCs are dendritic cells, keratinocytes, astrocytes, monocytes, macrophages, B lymphocytes, a microglial cell, or activated endothelial cells, and the like.

The invention also provides an expression cassette comprising a nucleic acid sequence encoding a chimeric protein comprising a first polypeptide domain comprising an endoplasmic reticulum chaperone polypeptide and a second polypeptide domain comprising at least one antigenic peptide. In alternative embodiments, the first domain comprises a calreticulin polypeptide and the second domain comprises an MHC class I-binding peptide epitope. In alternative embodiments, the expression cassette comprises an expression vector, a recombinant virus (e.g., an adenovirus, a retrovirus), a plasmid. The expression cassette can comprise a self-replicating RNA replicon. The self-replicating RNA replicon can comprise a Sindbis virus self-replicating RNA vector, such as, e.g., a Sindbis virus self-replicating RNA vector SINrep5 (U.S. Pat. No. 5,217,879). As with all applicable embodiments of the invention, the ER chaperone polypeptide can include any ER polypeptide having chaperone functions similar to the exemplary chaperones calreticulin, 1, tapasin, or ER60 polypeptides; or, analogues or mimetics thereof, or, functional fragments thereof.

The invention also provides a particle comprising a nucleic acid encoding a chimeric protein comprising a first polypeptide domain comprising an endoplasmic reticulum chaperone polypeptide and a second polypeptide domain comprising at least one antigenic peptide. In one embodiment, the isolated particle comprising an expression cassette comprising a nucleic acid sequence encoding a fusion protein comprising at least two domains, wherein the first domain comprises a calreticulin polypeptide and the second domain comprises an MHC class I-binding peptide epitope. The isolated particle can comprise any material suitable for particle bombardment, such as, e.g., gold. The ER chaperone polypeptide can include any ER polypeptide having chaperone functions similar to the exemplary chaperones calreticulin, calnexin, tapasin, or ER60 polypeptides, as discussed herein.

The invention also provides a cell comprising a nucleic acid sequence encoding a chimeric protein comprising a first polypeptide domain comprising an endoplasmic reticulum chaperone polypeptide and a second polypeptide domain comprising at least one antigenic peptide. In one embodiment, the cell comprises an expression cassette comprising a nucleic acid sequence encoding a fusion protein comprising at least two domains, wherein the first domain comprises a calreticulin polypeptide and the second domain comprises an MHC class I-binding peptide epitope. The cell can be transfected, infected, transduced, etc., with a nucleic acid of the invention or infected with a recombinant virus of the invention. The cell can be isolated from a non-human transgenic animal comprising cells comprising expression cassettes of the invention. Any cell can comprise an expression cassette of the invention, such as, e.g., cells of the immune system or antigen presenting cells (APCs). The APCs can be a dendritic cell, a keratinocyte, a macrophage, a monocyte, a B lymphocyte, an astrocyte, a microglial cell, or an activated endothelial cell.

The invention also provides a chimeric polypeptide comprising a first polypeptide domain comprising an endoplasmic reticulum chaperone polypeptide and a second polypeptide domain comprising at least one antigenic peptide. The antigenic peptide can comprise an MHC Class I-binding peptide epitope. The ER chaperone polypeptide can be chemically linked to the antigenic peptide, e.g., as a fusion protein (e.g., a peptide bond), that can be, e.g., synthetic or recombinantly produced, in vivo or in vitro. The polypeptide domains can be linked by a flexible chemical linker.

In alternative embodiments, the first polypeptide domain of the chimeric polypeptide can be closer to the amino terminus than the second polypeptide domain, or, the second polypeptide domain can be closer to the amino terminus than the first polypeptide domain. The ER chaperone polypeptide can include any ER polypeptide having chaperone functions similar to the exemplary chaperones calreticulin, calnexin, tapasin, or ER60 polypeptides, as discussed herein.

The invention provides a pharmaceutical composition comprising a composition of the invention capable of inducing or enhancing an antigen specific immune response and a pharmaceutically acceptable excipient. In alternative embodiments, the composition comprises: a chimeric polypeptide comprising a first domain comprising an endoplasmic reticulum chaperone polypeptide and a second domain comprising an antigenic peptide; a nucleic acid molecule encoding a fusion protein comprising a first polypeptide domain comprising an endoplasmic reticulum chaperone polypeptide and a second polypeptide domain an antigenic peptide; an expression cassette comprising a nucleic acid sequence encoding a fusion protein comprising a first domain comprising an endoplasmic reticulum chaperone polypeptide and a second domain comprising an antigenic peptide; a particle comprising a nucleic acid sequence encoding a fusion protein comprising a first domain comprising an endoplasmic reticulum chaperone polypeptide and a second domain comprising an antigenic peptide; or, a cell comprising a nucleic acid sequence encoding a fusion protein comprising a first domain comprising an endoplasmic reticulum chaperone polypeptide coding sequence and a second domain comprising an antigenic peptide. The ER chaperone polypeptide can include any ER polypeptide having chaperone functions similar to the exemplary chaperones calreticulin, calnexin, tapasin, or ER60 polypeptides, as discussed herein.

The invention provides a method of inducing or enhancing an antigen specific immune response comprising: (a) providing a composition comprising a composition of the invention capable of inducing or enhancing an antigen specific immune response, which, in alternative embodiments, can be: a chimeric polypeptide comprising a first domain comprising an endoplasmic reticulum chaperone polypeptide and a second domain comprising an antigenic peptide; a nucleic acid molecule encoding a fusion protein comprising a first polypeptide domain comprising an endoplasmic reticulum chaperone polypeptide and a second polypeptide domain an antigenic peptide; an expression cassette comprising a nucleic acid sequence encoding a fusion protein comprising a first domain comprising an endoplasmic reticulum chaperone polypeptide and a second domain comprising an antigenic peptide; a particle comprising a nucleic acid sequence encoding a fusion protein comprising a first domain comprising an endoplasmic reticulum chaperone polypeptide and a second domain comprising an antigenic peptide; or, a cell comprising a nucleic acid sequence encoding a fusion protein comprising a first domain comprising an endoplasmic reticulum chaperone polypeptide coding sequence and a second domain comprising an antigenic peptide; and, (b) administering an amount of the composition sufficient to induce or enhance an antigen specific immune response. The antigen specific immune response can comprise cellular response, such as a $CD8^+$ CTL response. The antigen specific immune response can also comprise an antibody-mediated response, or, a humoral and a cellular response.

In practicing the method the composition can administered ex vivo, or, the composition can be administered ex vivo to an antigen presenting cell (APC). In alternative embodiments, the APC is a dendritic cell, a keratinocyte, a macrophage, a monocyte, a B lymphocyte, an astrocyte, a microglial cell, or an activated endothelial cell. The APC can be a human cell. The APC can be isolated from an in vivo or in vitro source. The method can further comprise administering the ex vivo-treated APC to a mammal, a human, a histocompatible individual, or to the same individual from which it was isolated. Alternatively, the composition is administered directly in vivo to a mammal, e.g., a human.

The composition can be administered intramuscularly, intradermally, or subcutaneously. The composition, e.g., the nucleic acid, expression cassette or particle, can be administered by ballistic injection. The composition can be administered intratumorally or peritumorally.

In alternative embodiment of the method, the antigenic peptide can be derived from a virus, such as a human papilloma virus. The antigenic peptide can be an HPV-16 E7 peptide. The antigenic peptide can be a tumor-specific or a tumor-associated peptide, such as a HER-2/neu peptide.

The invention provides a method of increasing the numbers of $CD8^+$ CTLs specific for a desired antigen in an individual comprising: (a) providing a composition comprising: a chimeric polypeptide comprising a first domain comprising an endoplasmic reticulum chaperone polypeptide and a second domain comprising an antigenic peptide; a nucleic acid molecule encoding a fusion protein, comprising a first polypeptide domain comprising an endoplasmic reticulum chaperone polypeptide and a second polypeptide domain an antigenic peptide; an expression cassette comprising a nucleic acid sequence encoding a fusion protein comprising a first domain comprising an endoplasmic reticulum chaperone polypeptide and a second domain comprising an antigenic peptide; a particle comprising a nucleic acid sequence encoding a fusion protein comprising a first domain comprising an endoplasmic reticulum chaperone polypeptide and a second domain comprising an antigenic peptide; or, a cell comprising a nucleic acid sequence encoding a fusion protein comprising a first domain comprising an endoplasmic reticulum chaperone polypeptide coding sequence and a second domain comprising an antigenic peptide; wherein the MHC class I-binding peptide epitope is derived from the antigen, and, (b) administering an amount of the composition sufficient to increase the numbers of antigen-specific CD8+ CTL.

The invention provides a method of inhibiting the growth of a tumor in an individual comprising: (a) providing a composition comprising: a chimeric polypeptide comprising a first domain comprising an endoplasmic reticulum chaperone polypeptide and a second domain comprising an antigenic peptide; a nucleic acid molecule encoding a fusion protein comprising a first polypeptide domain comprising an endoplasmic reticulum chaperone polypeptide and a second polypeptide domain an antigenic peptide; an expression cassette comprising a nucleic acid sequence encoding a fusion protein comprising a first domain comprising an endoplasmic reticulum chaperone polypeptide and a second domain comprising an antigenic peptide; a particle comprising a nucleic acid sequence encoding a fusion protein comprising a first domain comprising an endoplasmic reticulum chaperone polypeptide and a second domain comprising an antigenic peptide; or, a cell comprising a nucleic acid sequence encoding a fusion protein comprising a first domain comprising an endoplasmic reticulum chaperone polypeptide coding sequence and a second domain comprising an antigenic peptide; and, (b) administering an amount of the composition sufficient to inhibit the growth of the tumor. In one embodiment of the invention, the composition is administered intratumorally or peritumorally. The composition can be co-administered with a second composition comprising anti-angiogenesis activity, such as angiostatin, endostatin or TIMP-2, or an equivalent thereof, or a mixture thereof. The composition can be co-administered with a radiotherapy or a chemotherapy composition.

The invention also provides self-replicating RNA virus constructs comprising nucleic acids encoding the immune response enhancing fusion proteins of the invention, including, e.g., chimeric proteins comprising ER chaperones and antigenic peptides, heat shock proteins and antigenic peptides, and equivalents thereof and mixtures thereof. In one embodiment, the self-replicating RNA virus comprises a Sindbis virus self-replicating RNA vector, such as SINrep5, as discussed in Example 2, below.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

FIG. 2 shows two-dimensional histograms summarizing FACS (flow cytometry) analysis of splenocytes from mice vaccinated with negative control and DNA expressing CRT alone, E7 alone and the CRT/E7 fusion protein of the invention, and stained with antibodies for CD8 and INF-gamma; as discussed in Example 1, below. FIG. 2B shows a schematic summary of the histogram data.

FIG. 9 shows a schematic diagram of SINrep5, SINrep5-HSP70, SINrep5-E7, SINrep5-E7/HSP70 DNA constructs. FIG. 9 shows a schematic diagram of RNA transcript derived from these DNA constructs using SP6 RNA polymerase as described in detail in Example 2, below.

DESCRIPTION OF THE PREFERRED EMBODIMENTS

Figure 1:
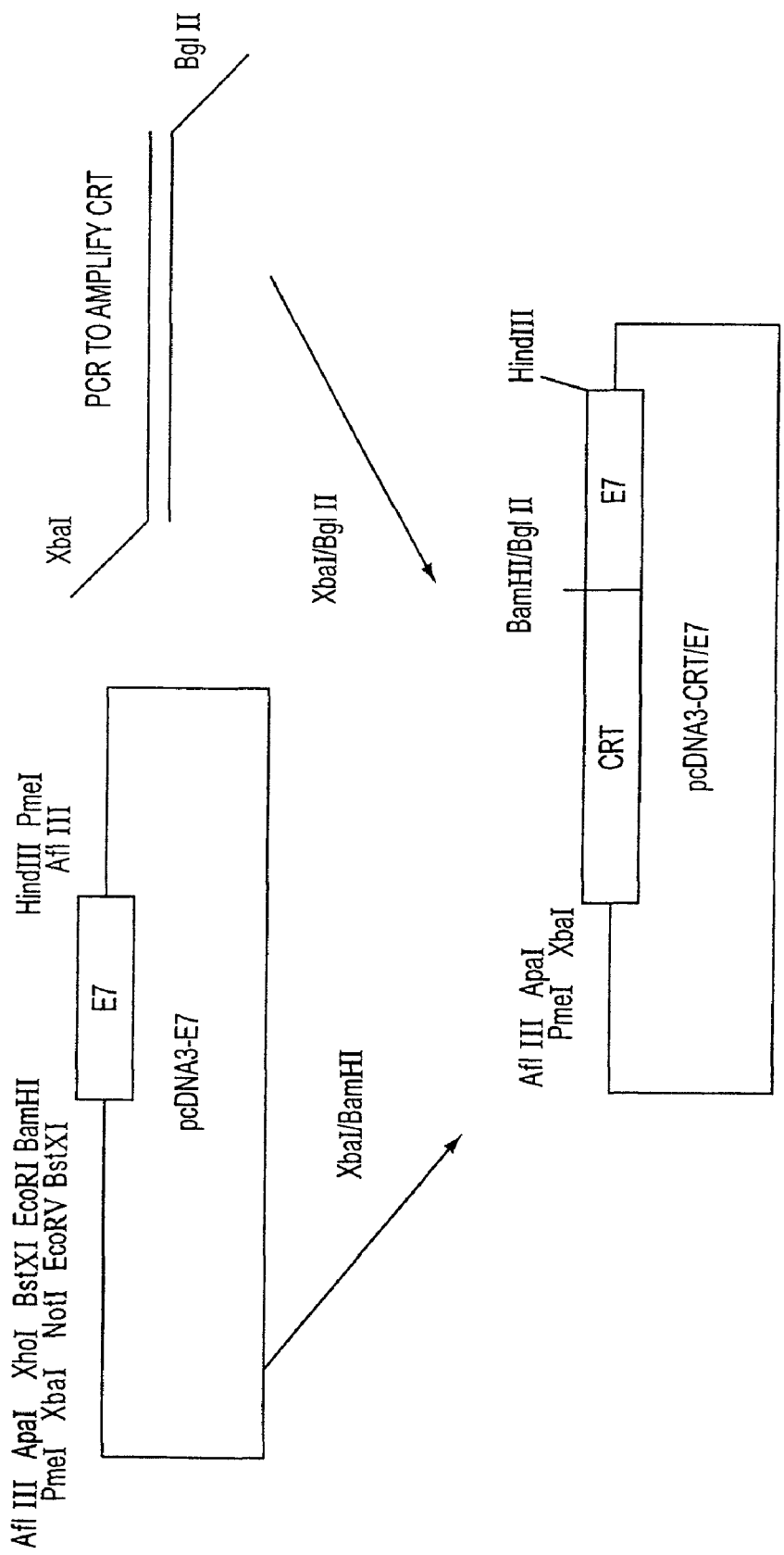
FIG. 1 shows a schematic diagram of the recombinant DNA constructs encoding calreticulin (CRT), HPV polypeptide E7, and the fusion protein of the invention calreticulin/E7 (CRT/E7), as discussed in Example 1, below.

The invention provides compositions and methods for enhancing the immune responses, particularly cytotoxic T cell immune responses, induced by ex vivo or in vivo administration of chimeric polypeptides comprising an endoplasmic reticulum chaperone polypeptide and at least one antigenic peptide. The chimeric polypeptides can be "indirectly" administered by administration of a nucleic acid that encodes the chimeric molecule; the nucleic acid construct, and thus the fusion protein, is expressed in vivo. In one embodiment, the chimeric nucleic acids or polypeptides are administered in the form of DNA vaccines.

The fusion protein comprises at least two domains: the first domain comprises a endoplasmic reticulum chaperone polypeptide and the second domain comprises an peptide derived from an antigen against which it is desired to induce an immune response. Any endoplasmic reticulum chaperone polypeptide, or functional fragment or variation thereof, can be used in the invention, such as calreticulin, tapasin, ER60 or calnexin polypeptides.

The second domain of the chimeric molecule comprises an antigenic peptide, which can be derived from a pathogen, a cancer, or any source to which induction, enhancement or suppression of an immune response is desired. In one embodiment, the peptide comprises an MHC class I-binding peptide epitope.

In the methods of the invention, the chimeric polypeptide or nucleic acid that encodes it are applied to induce or enhance immune responses. In one embodiment, the compositions of the invention synergistically enhance immune responses and antitumor effects through both immunological and anti-angiogenic mechanisms.

The experiments described herein demonstrate that the methods of the invention can enhance a cellular immune response, particularly, a CTL reactivity, induced by a DNA vaccine encoding an epitope of a human pathogen. Human HPV-16 E7 was used. It is a model antigen for vaccine development because human papillomaviruses (HPVs), particularly HPV-16, are associated with most human cervical cancers. The oncogenic HPV protein E7 is important in the induction and maintenance of cellular transformation and co-expressed in most HPV-containing cervical cancers and their precursor lesions. Therefore, cancer vaccines, such as the compositions of the invention, that target E7 can be used to control of HPV-associated neoplasms (Wu (1994) Curr. Opin. Immunol. 6:746-754).

As described in Example 1, below, the results of these experiments demonstrate that DNA vaccines comprising nucleic acid encoding a fusion protein comprising CRT linked to full-length E7 polypeptide can enhance the potency of DNA vaccines. DNA vaccines of the invention containing chimeric CRT/E7 fusion genes were administered to mice by ballistic subcutaneous methods. They induced increased E7-specific CD8+ CTL precursors, thereby improving immune protection against the tumors. This increase in E7-specific CD8+ T cell precursors was significant as compared to DNA vaccines containing wild-type E7 or CRT genes alone.

Furthermore, treatment of C57BL/6 mice (an inbred strain with a normal immune system) or nude mice (a strain lacking T cells and a functional immune system) with either CRT DNA or chimeric CRT/E7 DNA led to reduction of lung metastatic nodules and inhibition of angiogenesis within the lung nodules. Thus, the DNA vaccines of the invention encoding chimeric CRT/E7 represents a unique approach that combines immunological and anti-angiogenic approaches for the generation of potent anti-tumor effects.

As discussed above, while investigations have made heat shock proteins (HSPs) more attractive for use in immunotherapy, the only HSP vaccines that have been tested thus far are in the form of protein-based vaccines or DNA-based vaccines. This invention for the first time incorporates and describes the administration of antigens, such as HSPs and the chimeric polypeptides of the invention, in the form of self-replicating RNA vaccines.

As described in Example 2, below, expression of an HSP70-human papillomavirus type 16 (HPV-16) E7 fusion protein in a self-replicating RNA vaccine greatly enhanced the potency of this antigenic polypeptide when it was expressed in vivo. Results described below demonstrated that an RNA replicon vaccine containing E7/HSP70 fusion genes induced significantly higher E7-specific T cell-mediated immune responses than vaccines containing the wild type E7 gene in vaccinated mice. In vitro studies demonstrated that E7 antigen from E7/HSP70 RNA replicon-transfected apoptotic cells can be taken up by bone marrow-derived dendritic cells and presented more efficiently through the MHC class I pathway than wild-type E7 RNA replicon-transfected apoptotic cells. The fusion of HSP70 to E7 converted a less effective vaccine into one with significant potency against E7-expression tumors. These results demonstrated that the use of self-replicating RNA vaccines can enhance the immunogenicity of the fusion proteins of the invention.

A potential mechanism for the enhanced antigen-specific $CD8^+$ T cell immune responses in vivo is the presentation of antigen through the MHC class I pathway by uptake of apoptotic bodies from cells expressing the antigen, also called "cross-priming". As discussed in Example 2, below, CTL assays demonstrated enhanced MHC class I presentation of HPV E7 polypeptide in bone marrow derived dendritic cells pulsed with apoptotic cells transfected by SINrep5-E7/HSP70 RNA.

DEFINITIONS

Unless defined otherwise, all technical and scientific terms used herein have the meaning commonly understood by a person skilled in the art to which this invention belongs. As used herein, the following terms have the meanings ascribed to them unless specified otherwise.

The term "anti-angiogenic activity" as used herein means any form of inhibition of blood vessel growth (e.g., capillary, arteriole, etc.); thus, such activity would include a slowing in the growth of blood vessels, or a substituent thereof, including, e.g., slowing or inhibiting the growth of endothelial cells.

The term "antigen" or "immunogen" as used herein refers to a compound or composition comprising a peptide, polypeptide or protein which is "antigenic" or "immunogenic" when administered (or expressed in vivo by an administered nucleic acid, e.g., a DNA vaccine) in an appropriate amount (an "immunogenically effective amount"), i.e., is capable of eliciting, augmenting or boosting a cellular and/or humoral immune response either alone or in combination or linked or fused to another substance (which can be administered at once or over several intervals).

"Calnexin" describes the well-characterized membrane protein of the endoplasmic reticulum (ER) that functions as a molecular chaperone and as a component of the ER quality control machinery. Calreticulin is a soluble analogue of calnexin. In vivo, calreticulin and calnexin play important roles in quality control during protein synthesis, folding, and post-translational modification. Calnexin polypeptides, and equivalents and analogues thereof, are species in the genus of ER chaperone polypeptides, as described herein (Wilson (2000) J. Biol. Chem. 275:21224-2132; Danilczyk (2000) J. Biol. Chem. 275:13089-13097; U.S. Pat. Nos. 6,071,743 and 5,691,306).

"Calreticulin" or "CRT" describes the well-characterized ~46 kDa resident protein of the ER lumen that has lectin activity and participates in the folding and assembly of nascent glycoproteins. CRT acts as a "chaperone" polypeptide and a member of the MHC class I transporter TAP complex; CRT associates with TAP1 and TAP2 transporters, tapasin, MHC Class I heavy chain polypeptide and $\beta 2$ microglobulin to function in the loading of peptide epitopes onto nascent MHC class I molecules (Jorgensen (2000) Eur. J. Biochem. 267:2945-2954). The term "calreticulin" or "CRT" refers to polypeptides and nucleic acids molecules having substantial identity (defined herein) to the exemplary CRT sequences as described herein. A CRT polypeptide is a polypeptides comprising a sequence identical to or substantially identical (defined herein) to the amino acid sequence of CRT. An exemplary nucleotide and amino acid sequence for a CRT used in the present compositions and methods are SEQ ID NO:1 and SEQ ID NO:2, respectively. The terms "calreticulin" or "CRT" encompass native proteins as well as recombinantly produced modified proteins that induce an immune response, including a CTL response. The terms "calreticulin" or "CRT" encompass homologues and allelic variants of CRT, including variants of native proteins constructed by in vitro techniques, and proteins isolated from natural sources. The CRT polypeptides of the invention, and sequences encoding them, also include fusion proteins comprising non-CRT sequences, particularly MHC class I-binding peptides; and also further comprising other domains, e.g. epitope tags, enzyme cleavage recognition sequences, signal sequences, secretion signals and the like.

The term "endoplasmic reticulum chaperone polypeptide" as used herein means any polypeptide having substantially the same ER chaperone function as the exemplary chaperone proteins CRT, tapasin, ER60 or calnexin. Thus, the term includes all functional fragments or variants or mimics thereof. A polypeptide or peptide can be routinely screened for its activity as an ER chaperone using assays known in the art, such as that set forth in Example 1. While the invention is not limited by any particular mechanism of action, in vivo chaperones promote the correct folding and oligomerization of many glycoproteins in the ER, including the assembly of the MHC class I heterotrimeric molecule (heavy (H) chain, $\beta 2$ m, and peptide). They also retain incompletely assembled MHC class I heterotrimeric complexes in the ER (Hauri (2000) FEBS Lett. 476:32-37).

The term "epitope" as used herein refers to an antigenic determinant or antigenic site that interacts with an antibody or a T cell receptor (TCR), e.g., the MHC class I-binding peptide compositions used in the methods of the invention. An "antigen" is a molecule or chemical structure that either induces an immune response or is specifically recognized or bound by the product of an immune response, such as an antibody or a CTL. The specific conformational or stereochemical "domain" to which an antibody or a TCR bind is an "antigenic determinant" or "epitope." TCRs bind to peptide epitopes which are physically associated with a third molecule, a major histocompatibility complex (MHC) class I or class II protein.

The terms "ER60" or "GRP94" or "gp96" or "glucose regulated protein 94" as used herein describes the well-characterized ER chaperone polypeptide that is the ER representative of the heat shock protein-90 (HSP90) family of stress-induced proteins. These bind to a limited number of proteins in the secretory pathway, possibly by recognizing advanced folding intermediates or incompletely assembled proteins. ER60 polypeptides, and equivalents and analogues thereof, are species in the genus of ER chaperone polypeptides, as described herein (Argon (1999) Semin. Cell Dev. Biol. 10:495-505; Sastry (1999) J. Biol. Chem. 274:12023-12035; Nicchitta (1998) Curr. Opin. Immunol. 10:103-109; U.S. Pat. No. 5,981,706).

The term "expression cassette" or "expression vector" as used herein refers to a nucleotide sequence which is capable of affecting expression of a protein coding sequence in a host compatible with such sequences. Expression cassettes include at least a promoter operably linked with the polypeptide coding sequence; and, optionally, with other sequences, e.g., transcription termination signals. Additional factors necessary or helpful in effecting expression may also be included, e.g., enhancers. "Operably linked" refers to linkage of a promoter upstream from a DNA sequence such that the promoter mediates transcription of the DNA sequence. Thus, expression cassettes include plasmids, recombinant viruses, any form of a recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons (see Example 2, below), bacteriophages) to which fragments of DNA may be attached and become replicated. Vectors thus include, but are not limited to RNA, autonomous self-replicating circular or linear DNA or RNA, e.g., plasmids, viruses, and the like (U.S. Pat. No. 5,217,879), and includes both the expression and nonexpression plasmids. Where a recombinant microorganism or cell culture is described as hosting an "expression vector" this includes both extrachromosomal circular and linear DNA and DNA t has been incorporated into the host chromosome(s). Where a vector is being maintained by a host cell, the vector may either be stably replicated by the cells during mitosis as an autonomous structure, or is incorporated within the host's genome.

The term "chemically linked" refers to any chemical bonding of two moieties, e.g., as in one embodiment of the invention, where an ER chaperone polypeptide is chemically linked to an antigenic peptide. Such chemical linking includes the peptide bonds of a recombinantly or in vivo generated fusion protein.

The term "chimeric" or "fusion" polypeptide or protein refers to a composition comprising at least one polypeptide or peptide sequence or domain which is associated with a second polypeptide or peptide domain. One embodiment of this invention is an isolated or recombinant nucleic acid molecule encoding a fusion protein comprising at least two domains, wherein the first domain comprises an endoplasmic reticulum chaperone, e.g., CRT, and the second domain comprising an antigenic epitope, e.g., an MHC class I-binding peptide epitope. Additional domains can comprise a polypeptide, peptide, polysaccharide, or the like. The "fusion" can be an association generated by a peptide bond, a chemical linking, a charge interaction (e.g., electrostatic attractions, such as salt bridges, H-bonding, etc.) or the like. If the polypeptides are recombinant, the "fusion protein" can be translated from a common message. Alternatively, the compositions of the domains can be linked by any chemical or electrostatic means. The chimeric molecules of the invention (e.g., CRT-class I-binding peptide fusion proteins) can also include additional sequences, e.g., linkers, epitope tags, enzyme cleavage recognition sequences, signal sequences, secretion signals, and the like. Alternatively, a peptide can be linked to a carrier simply to facilitate manipulation or identification/location of the peptide.

The term "immunogen" or "immunogenic composition" refers to a compound or composition comprising a peptide, polypeptide or protein which is "immunogenic," i.e., capable of eliciting, augmenting or boosting a cellular and/or humoral immune response, either alone or in combination or linked or fused to another substance. An immunogenic composition can be a peptide of at least about 5 amino acids, a peptide of 10 amino acids in length, a fragment 15 amino acids in length, a fragment 20 amino acids in length or greater; smaller immunogens may require presence of a "carrier" polypeptide e.g., as a fusion protein, aggregate, conjugate or mixture, preferably linked (chemically or otherwise) to the immunogen. The immunogen can be recombinantly expressed from a vaccine vector, which can be naked DNA comprising the immunogen's coding sequence operably linked to a promoter, e.g., an expression cassette. The immunogen includes one or more antigenic determinants or epitopes which may vary in size from about 3 to about 15 amino acids.

The term "isolated" as used herein, when referring to a molecule or composition, such as, e.g., a CRT nucleic acid or polypeptide, means that the molecule or composition is separated from at least one other compound, such as a protein, other nucleic acids (e.g., RNAs), or other contaminants with which it is associated in vivo or in its natural state. Thus, a CRT composition is considered isolated when it has been isolated from any other component with which it is natively associated, e.g., cell membrane, as in a cell extract. An isolated composition can, however, also be substantially pure. An isolated composition can be in a homogeneous state and can be dry or in an aqueous solution. Purity and homogeneity can be determined, for example, using analytical chemistry techniques such as polyacrylamide gel electrophoresis (SDS-PAGE) or high performance liquid chromatography (HPLC). Thus, the isolated compositions of this invention do not contain materials normally associated with their in situ environment. Even where a protein has been isolated to a homogenous or dominant band, there are trace contaminants which co-purify with the desired protein.

The phrase "the HPV-16 E7 polypeptide is non-oncogenic" as used herein means a variant (e.g., deletion, substitution, and the like) of the HPV-16 E7 polypeptide that does not bind retinoblastoma polypeptide (pRB) or binds pRB with such low affinity that the HPV-16 E7 polypeptide variant is substantially non-oncogenic. HPV polypeptides, including HPV-16 E7 polypeptide, are well described in the art; for HPV-16 E7 GenBank Accession No. AF125673 (Jun. 01, 1999) shows the complete HPV-16 genome and the HPV-16 E7 protein, having the sequence SEQ ID NO:5 (see below).

The terms "polypeptide," "protein," and "peptide" include compositions of the invention that also include "analogues," or "conservative variants" and "mimetics" or "peptidomimetics": with structures and activity that substantially correspond to the polypeptide from which the variant was derived, including, e.g., human CRT or the Class I-binding peptide epitope, as the HPV-16 E7 polypeptide, as discussed in detail, below.

The term "pharmaceutical composition" refers to a composition suitable for pharmaceutical use, e.g., as a vaccine, in a subject. The pharmaceutical compositions of this invention are formulations that comprise a pharmacologically effective amount of a composition comprising, e.g., a nucleic acid, or vector, or cell of the invention, and a pharmaceutically acceptable carrier.

The term "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant" refers to (1) a polynucleotide synthesized or otherwise manipulated in vitro (e.g., "recombinant polynucleotide"), (2) methods of using recombinant polynucleotides to produce gene products in cells or other biological systems, or (3) a polypeptide ("recombinant protein") encoded by a recombinant polynucleotide. For example, recombinant CRT or an MHC class I-binding peptide epitope can be recombinant as used to practice this invention. "Recombinant means" also encompass the ligation of nucleic acids having various coding regions or domains or promoter sequences from different sources into an expression cassette or vector for expression of, e.g., inducible or constitutive expression of polypeptide coding sequences in the vectors used to practice this invention.

The term "self-replicating RNA replicon" refers to constructs based on RNA viruses, e.g., alphavirus genome RNAs (e.g., Sindbis virus, Semliki Forest virus, etc.), that have been engineered to allow expression of heterologous RNAs and proteins. These recombinant vectors are self-replicating (i.e., they are "replicons") and can be introduced into cells as naked RNA or DNA, as described in detail, below. In one embodiment, the self-replicating RNA replicon comprises a Sindbis virus self-replicating RNA vector SINrep5, which is described in detail in U.S. Pat. No. 5,217,879.

The term "systemic administration" refers to administration of a composition or agent such as the molecular vaccine or the CRT-Class I-binding peptide epitope fusion protein described herein, in a manner that results in the introduction of the composition into the subject's circulatory system. The term "regional" administration refers to administration of a composition into a specific anatomical space, such as intraperitoneal, intrathecal, subdural, or to a specific organ, and the like. For example, regional administration includes administration of the composition or drug into the hepatic artery. The term "local administration" refers to administration of a composition or drug into a limited, or circumscribed, anatomic space, such as intratumoral injection into a tumor mass, subcutaneous injections, intramuscular injections, and the like. Any one of skill in the art would understand that local administration or regional administration may also result in entry of the composition or drug into the circulatory system.

"Tapasin" is the known ER chaperone polypeptide, as discussed above. While not limited by any particular mechanism of action, in vivo, tapasin is a subunit of the TAP (transporter associated with antigen processing) complex and binds both to TAP 1 and MHC class I polypeptides. Tapasin polypeptides, and equivalents and analogues thereof, are species in the genus of ER chaperone polypeptides, as described herein (Barnden (2000) J. Immunol. 165:322-330; Li (2000) *J. Biol. Chem.* 275:1581-1586).

Generating and Manipulating of Nucleic Acids

The methods of the invention provide for the administration of nucleic acids encoding a CRT-Class I epitope binding peptide fusion protein, as described above. Recombinant CRT-containing fusion proteins can be synthesized in vitro or in vivo. Nucleic acids encoding these compositions can be in the form of "naked DNA" or they can be incorporated in plasmids, vectors, recombinant viruses (e.g., "replicons") and the like for in vivo or ex vivo administration. Nucleic acids and vectors of the invention can be made and expressed in vitro or in vivo, a variety of means of making and expressing these genes and vectors can be used. One of skill will recognize that desired gene activity can be obtained by modulating the expression or activity of the genes and nucleic acids (e.g., promoters) within vectors used to practice the invention. Any of the known methods described for increasing or decreasing expression or activity, or tissue specificity, of genes can be used for this invention. The invention can be practiced in conjunction with any method or protocol known in the art, which are well described in the scientific and patent literature.

General Techniques

The nucleic acid sequences used to practice this invention, whether RNA, cDNA, genomic DNA, vectors, recombinant viruses or hybrids thereof, may be isolated from a variety of sources, genetically engineered, amplified, and/or expressed recombinantly. Any recombinant expression system can be used, including, in addition to bacterial cells, e.g., mammalian, yeast, insect or plant cell expression systems. Alternatively, these nucleic acids can be synthesized in vitro by well-known chemical synthesis techniques, as described in, e.g., Carruthers (1982) Cold Spring Harbor Symp. Quant. Biol. 47:411-418; Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with an appropriate primer sequence.

The sequences of CRT, including human CRT, are well known in the art (McCauliffe (1990) J. Clin. Invest. 86:332-335; Burns (1994) Nature 367:476-480; Coppolino (1998) Int. J. Biochem. Cell Biol. 30:553-558). The nucleic acid sequence appears as GenBank Accession No. NM 004343 and is SEQ ID NO:1.

```
   1 gtccgtactg cagagccgct gccggagggt cgttttaaag ggccgcgttg ccgccccctc
  61 ggcccgccat gctgctatcc gtgccgctgc tgctcggcct cctcggcctg gccgtcgccg
 121 agcccgccgt ctacttcaag gagcagtttc tggacggaga cgggtggact tcccgctgga
 181 tcgaatccaa acacaagtca gattttggca aattcgttct cagttccggc aagttctacg
 241 gtgacgagga gaaagataaa ggtttgcaga caagccagga tgcacgcttt tatgctctgt
 301 cggccagttt cgagcctttc agcaacaaag gccagacgct ggtggtgcag ttcacggtga
 361 aacatgagca gaacatcgac tgtgggggcg gctatgtgaa gctgtttcct aatagtttgg
 421 accagacaga catgcacgga gactcagaat acaacatcat gtttggtccc gacatctgtg
 481 gccctgcac caagaaggtt catgtcatct tcaactacaa gggcaagaac gtgctgatca
 541 acaaggacat ccgttgcaag gatgatgagt ttacacacct gtacacactg attgtgcggc
 601 cagacaacac ctatgaggtg aagattgaca cagccaggt ggagtccggc tccttggaag
 661 acgattggga cttcctgcca cccaagaaga taaaggatcc tgatgcttca aaaccggaag
 721 actgggatga gcgggccaag atcgatgatc ccacagactc caagcctgag gactgggaca
 781 agcccgagca tatccctgac cctgatgcta agaagcccga ggactgggat gaagagatgg
 841 acggagagtg ggaacccca gtgattcaga accctgagta caagggtgag tggaagcccc
 901 ggcagatcga caacccagat tacaagggca cttggatcca cccagaaatt gacaaccccg
 961 agtattctcc cgatcccagt atctatgcct atgataactt tggcgtgctg ggcctggacc
1021 tctggcaggt caagtctggc accatctttg acaacttcct catcaccaac gatgaggcat
1081 acgctgagga gtttggcaac gagacgtggg gcgtaacaaa ggcagcagag aaacaaatga
1141 aggacaaaca ggacgaggag cagaggctta aggaggagga agaagacaag aaacgcaaag
1201 aggaggagga ggcagaggac aaggaggatg atgaggacaa agatgaggat gaggaggatg
1261 aggaggacaa ggaggaagat gaggaggaag atgtccccgg ccaggccaag gacgagctgt
1321 agagaggcct gcctccaggg ctggactgag gcctgagcgc tcctgccgca gagcttgccg
1381 cgccaaataa tgtctctgtg agactcgaga actttcattt ttttccaggc tggttcggat
1441 ttggggtgga ttttggtttt gttccctcc tccactctcc cccaccccct cccgcctt
1501 ttttttttt tttaaact ggtattttat cctttgattc tccttcagcc.ctcacccctg
1561 gttctcatct ttcttgatca acatcttttc ttgcctctgt gccccttctc tcatctctta
1621 gctcccctcc aacctgggg gcagtggtgt ggagaagcca caggcctgag atttcatctg
1681 ctctccttcc tggagcccag aggagggcag cagaagggg tggtgtctcc aaccccccag
```

```
-continued
1741 cactgaggaa gaacggggct cttctcattt caccectccc tttctcccct gccccagga 1801 ctgggccact tctgggtggg gcagtgggtc ccagattggc tcacactgag aatgtaagaa 1861 ctacaaacaa aatttctatt aaattaaatt ttgtgtctc            1899
```

Techniques for the manipulation of nucleic acids, such as, e.g., generating mutations in sequences, subcloning, labeling probes, sequencing, hybridization and the like are well described in the scientific and patent literature. See, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Amplification of Nucleic Acids

Oligonucleotide primers can be used to amplify nucleic acids to generate fusion protein coding sequences used to practice the invention, to monitor levels of vaccine after in vivo administration (e.g., levels of a plasmid or virus), to confirm the presence and phenotype of activated CTLs, and the like. The skilled artisan can select and design suitable oligonucleotide amplification primers using known sequences, e.g., SEQ ID NO:1. Amplification methods are also well known in the art, and include, e.g., polymerase chain reaction, PCR (*PCR Protocols, A Guide to Methods and Applications*, ed. Innis, Academic Press, N.Y. (1990) and *PCR Strategies* (1995), ed. Innis, Academic Press, Inc., N.Y., ligase chain reaction (LCR) (Wu (1989) Genomics 4:560; Landegren (1988) Science 241:1077; Barringer (1990) Gene 89:117); transcription amplification (Kwoh (1989) Proc. Natl. Acad. Sci. USA 86:1173); and, self-sustained sequence replication (Guatelli (1990) Proc. Natl. Acad. Sci. USA 87:1874); Qβ replicase amplification (Smith (1997) J. Clin. Microbiol. 35:1477-1491; Burg (1996) Mol. Cell. Probes 10:257-271) and other RNA polymerase mediated techniques (NASBA, Cangene, Mississauga, Ontario; Berger (1987) Methods Enzymol. 152:307-316; U.S. Pat. Nos. 4,683,195 and 4,683,202; Sooknanan (1995) Biotechnology 13:563-564).

Cloning and Construction of Expression Cassettes

Expression cassettes, including plasmids, recombinant viruses (e.g., RNA viruses like the replicons described below) and other vectors encoding the fusion proteins described herein are used to express these polypeptides in vitro and in vivo. Recombinant nucleic acids are expressed by a variety of conventional techniques (Roberts (1987) Nature 328:731; Schneider (1995) Protein Expr. Purif. 6435:10; Sambrook, supra Tijssen, supra; Ausubel, supra). Plasmids, vectors, etc., can be isolated from natural sources, obtained from such sources as ATCC or GenBank libraries, or prepared by synthetic or recombinant methods.

The nucleic acids used to practice the invention can be stably or transiently expressed in cells such as episomal expression systems. Selection markers can be incorporated to confer a selectable phenotype on transformed cells. For example, selection markers can code for episomal maintenance and replication such that integration into the host genome is not required. For example, the marker may encode antibiotic resistance, e.g., chloramphenicol, kanamycin, G418, bleomycin, hygromycin) to permit selection of those cells transformed with the desired DNA sequences (Blondelet-Rouault (1997) Gene 190:315-317; Aubrecht (1997) J. Pharmacol. Exp. Ther. 281:992-997).

In Vivo Nucleic Acid Administration

In one embodiment, the nucleic acids encoding the CRT-Class I-binding peptide epitopes are cloned into expression cassettes such as plasmids or other vectors, viruses that can transfect or infect cells in vitro, ex vivo and/or in vivo. A number of delivery approaches are known, including lipid or liposome based gene delivery (Mannino (1988) BioTechniques 6:682-691; U.S. Pat. No. 5,279,833), replication-defective retroviral vectors with desired exogenous sequence as part of the retroviral genome (Miller (1990) Mol. Cell. Biol. 10:4239; Kolberg (1992) J. NIH Res. 4:43; Cornetta (1991) Hum. Gene Ther. 2: 215; Zhang (1996) Cancer Metastasis Rev. 15:385-401; Anderson, Science (1992) 256: 808-813; Nabel (1993) TIBTECH 11: 211-217; Mitani (1993) TIBTECH 11: 162-166; Mulligan (1993) Science, 926-932; Dillon (1993) TIBTECH 11: 167-175; Miller (1992) Nature 357: 455-460).

Expression cassettes can also be derived from viral genomes. Vectors which may be employed include recombinantly modified enveloped or non-enveloped DNA and RNA viruses, examples of which are baculoviridae, parvoviridae, picornoviridae, herpesviridae, poxyiridae, adenoviridae, picornnaviridae or alphaviridae. Chimeric vectors may also be employed which exploit advantageous merits of each of the parent vector properties (Feng (1997) Nature Biotechnology 15:866-870). Such viral genomes may be modified by recombinant DNA techniques to include the gene of interest and may be engineered to be replication-deficient, conditionally replicating or replication-competent. Vectors can be derived from adenoviral, adeno-associated viral or retroviral genomes. Retroviral vectors can include those based upon murine leukemia virus (MuLV), gibbon ape leukemia virus (GaLV), simian immunodeficiency virus (SIV), human immunodeficiency virus (HIV), and combinations thereof (Buchscher (1992) J. Virol. 66(5) 2731-2739; Johann (1992) J. Virol. 66 (5):1635-1640 (1992); Sommerfelt (1990) Virol. 176:58-59; Wilson (1989) J. Virol. 63:2374-2378; Miller (1991) J. Virol. 65:2220-2224. Adeno-associated virus (AAV)-based vectors can transduce cells for the in vitro production of nucleic acids and peptides, and be used in in vivo and ex vivo therapy procedures (Okada (1996) Gene Ther. 3:957-964; West (1987) Virology 160:38-47; Carter (1989) U.S. Pat. No. 4,797,368; Carter et al. WO 93/24641 (1993); Kotin (1994) Human Gene Therapy 5:793-801; Muzyczka (1994) J. Clin. Invst. 94:1351).

In vivo Administration Using Self-replicating RNA Replicons

In addition to the above-described expression vectors and recombinant viruses, self-replicating RNA replicons can also be used to infect cells or tissues or whole organisms with a fusion protein-expressing nucleic acids of the invention. Thus, the invention also incorporates RNA viruses, including alphavirus genome RNAs such as from Sindbis virus, Semliki Forest virus, Venezuelan equine encephalitis virus, and the like, that have been engineered to allow expression of heterologous RNAs and proteins. High levels of expression of heterologous sequences such as the fusion polypeptides of the invention, are achieved when the viral structural genes are replaced by the heterologous coding sequences.

These recombinant RNAs are self-replicating ("replicons") and can be introduced into cells as naked RNA or DNA. However, they require trans complementation to be packaged and released from cells as infectious virion particles. The defective helper RNAs contain the cis-acting sequences required for replication as well as an RNA promoter which drives expression of open reading frames. In cells co-transfected with both the replicon and defective helper RNAs, viral nonstructural proteins translated from the replicon RNA allow replication and transcription of the defective helper RNA to produce the virion's structural proteins (Bredenbeek (1993) J. Virol. 67:6439-6446).

RNA replicon vaccines may be derived from alphavirus vectors, such as Sindbis virus (family Togaviridae) (Xiong (1989) Science 243:1188-1191), Semliki Forest virus (Ying (1999) Nat. Med. 5:823-827) or Venezuelan equine encephalitis virus (Pushko (1997) Virology 239:389-401) vectors. These vaccines are self-replicating and self-limiting and may be administered as either RNA or DNA, which is then transcribed into RNA replicons in transfected cells or in vivo (Berglund (1998) Nat. Biotechnol. 16:562-565). Self-replicating RNA infects a diverse range of cell types and allows the expression of the antigen of interest at high levels (Huang (1996) Curr. Opin. Biotechnol. 7:531-535). Additionally, self-replicating RNA eventually causes lysis of transfected cells because viral replication is toxic to infected host cells (Frolov (1996) J. Virol. 70:1182-1190). These vectors therefore do not raise the concern associated with naked DNA vaccines of integration into the host genome. This is particularly important for vaccine development targeting proteins that are potentially oncogenic, such as the adenoviral E7 protein.

In one embodiment, the self-replicating RNA replicon comprises a Sindbis virus self-replicating RNA vector SINrep5, as described in detail by Bredenbeek, supra and Herrmann (1998) Biochem. Biophys Res. Commun. 253:524-531.

Polypeptides

In other embodiments, the invention is directed to an isolated or recombinant polypeptide comprising at least two domains, wherein the first domain comprises a calreticulin (CRT) polypeptide; and, wherein the second domain comprises an MHC class I-binding peptide epitope. As noted above, the terms "polypeptide," "protein," and "peptide," referring to polypeptides including the CRT, fragments of CRT that bind peptides, and MHC class I-binding peptide epitopes, used to practice the invention, include compositions of the invention that also include "analogues," or "conservative variants" and "mimetics" or "peptidomimetics" with structures and activity that substantially correspond to CRT and MHC class I-binding peptide epitopes. Thus, the terms "conservative variant" or "analogue" or "mimetic" also refer to a polypeptide or peptide which has a modified amino acid sequence, such that the change(s) do not substantially alter the polypeptide's (the conservative variant's) structure and/or activity (ability to bind to "antigenic" peptides, to stimulate an immune response). These include conservatively modified variations of an amino acid sequence, i.e., amino acid substitutions, additions or deletions of those residues that are not critical for protein activity, or substitution of amino acids with residues having similar properties (acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue/substitution): Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu.

An alternative exemplary guideline uses the groups shown in the Table below. For a detailed description of protein chemistry and structure, see Schulz, G E et al., Principles of Protein Structure, Springer-Verlag, New York, 1978, and Creighton, T. E., Proteins: Structure and Molecular Properties, W.H. Freeman & Co., San Francisco, 1983, which are hereby incorporated by reference. The types of substitutions that may be made in the polypeptides of this invention may be based on analysis of the frequencies of amino acid changes between a homologous protein of different species, defined herein as exchanges within one of the following five groups:

| 1 | Small aliphatic, nonpolar or slightly polar residues | Ala, Ser, Thr (Pro, Gly); |
|---|---|---|
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or His, for (or by) a residue having an electronegative charge, e.g., Glu or Asp; or (v) substitution of a residue having a bulky side chain, e.g., Phe, for (or by) a residue not having such a side chain, e.g., Gly.

One of skill in the art will appreciate that the above-identified substitutions are not the only possible conservative substitutions. For example, for some purposes, all charged amino acids may be considered conservative substitutions for each other whether they are positive or negative. Individual substitutions, deletions or additions that alter, add or delete a single amino acid or a small percentage of amino acids in an encoded sequence can also be considered to yield "conservatively modified variants."

The terms "mimetic" and "peptidomimetic" refer to a synthetic chemical compound that has the necessary structural and/or functional characteristics of a peptide that permits use in the methods of the invention, such as mimicking CRT in interaction with peptides and MHC class I-proteins). The mimetic can be either entirely composed of synthetic, non-natural analogues of amino acids, or, is a combination of partly natural amino acids and partly non-natural analogues. The mimetic can also incorporate any amount of natural amino acid conservative substitutions as long as such substitutions also do not substantially alter the mimetics' structure and/or activity. As with conservative variants, routine experimentation will determine whether a mimetic is within the scope of the invention, that its sterochemical structure and/or function is not substantially altered. Peptide mimetics can contain any combination of "non-natural" structural components, typically from three groups: (a) residue linkage groups other than the natural amide bond ("peptide bond"); (b) non-natural residues in place of naturally occurring amino acids; or (c) residues which induce or stabilize a secondary structure, e.g, a β turn, γ turn, β sheet, or α helix conformation. A polypeptide can be characterized as a mimetic when all or some of its residues are joined by chemical bonds other than peptide bonds. Individual peptidomimetic residues can be joined by peptide bonds, other chemical bonds or coupling means, such as glutaraldehyde, N-hydroxysuccinimide esters, bifunctional maleimides, N,N'-dicyclohexylcarbodiimide (DCC) or N,N'-diisopropylcarbodiimide (DIC). Linking groups that are alternatives to peptide bonds include, ketomethylene (—C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (Spatola (1983) in *Chemistry and Biochemistry of Amino Acids, Peptides and Proteins*, Vol. 7, pp 267-357, *Peptide Backbone Modifications*, Marcell Dekker, NY).

The structure of the polypeptides, peptides, other functional derivatives, including mimetics of the present invention are preferably based on structure and amino acid sequence of CRT, preferably human CRT (McCauliffe (1990) J. Clin. Invest. 86:332-335; Burns (1994) Nature 367:476-480; Coppolino (1998) Int. J. Biochem. Cell Biol. 30:553-558) Human CRT protein (GenBank Accession No. NM 004343), (SEQ ID NO:2) is shown below:

Individual synthetic residues and polypeptides incorporating mimetics can be synthesized using a variety of procedures and methodologies well known in the art, e.g., *Organic Syntheses Collective Volumes*, Gilman et al. (dds) John Wiley & Sons, Inc., NY. Polypeptides incorporating mimetics can also be made using solid phase synthetic procedures (e.g., U.S. Pat. No. 5,422,426). Peptides and peptide mimetics of the invention can also be synthesized using combinatorial methodologies. Various techniques for generation of peptide and peptidomimetic libraries are well known e.g., multipin, tea bag, and split-couple-mix techniques (al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234). Modified polypeptide and peptides can be further produced by chemical modification (Belousov (1997) Nucleic Acids Res. 25:3440-3444; Frenkel (1995) Free Radic. Biol. Med. 19:373-380; Blommers (1994) Biochemistry 33:7886-7896).

The peptides can also be synthesized, whole or in part, using conventional chemical synthesis (Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (Roberge (1995) Science 269: 202; Merrifield (1997) Methods Enzymol. 289:3-13) and automated synthesis, e.g., using the ABI 431A Peptide Synthesizer (Perkin Elmer) in accordance with the manufacturer' instructions.

In one embodiment of the invention, peptide-binding fragments or "sub-sequences" of CRT are used. In another embodiment, other peptides that bind to MHC proteins, preferably MHC Class I proteins, are used. Such peptides can be derived from any polypeptide, particularly, from a known pathogen, or it can be entirely synthetic). Methods for determining whether, and to what extent, a peptide binds to a CRT or a CRT fragment, or an MHC protein are routine in the art (Jensen (1999) Immunol. Rev. 172:229-238; Zhang (1998) J. Mol. Biol. 281:929-947; Morgan (1997) Protein Sci 6:1771-1773; Fugger (1996) Mol. Med. 2:181-188; Sette (1994) Mol. Immunol. 31:813-822; Elvin (1993) J. Immunol. Methods 158:161-171; U.S. Pat. Nos. 6,048,530; 6,037,135; 6,033, 669; 6,007,820).

Formulation and Administration of Pharmaceutical Compositions

In various embodiments of the invention, polypeptides, nucleic acids, expression cassettes, cells, and particles, are administered to an individual as pharmacological compositions in amounts sufficient to induce an antigen-specific immune response (e.g., a CTL response, see Example, below) in the individual.

```
  1 MLLSVPLLLG LLGLAVAEPA VYFKEQFLDG DGWTSRWIES KHKSDFGKFV LSSGKFYGDE

61 EKDKGLQTSQ DARFYALSAS FEPFSNKGQT LVVQFTVKHE QNIDCGGGYV KLFPNSLDQT

121 DMHGDSEYNI MFGPDICGPG TKKVHVIFNY KGKNVLINKD IRCKDDEFTH LYTLIVRPDN

181 TYEVKIDNSQ VESGSLEDDW DFLPPKKIKD PDASKPEDWD ERAKIDDPTD SKPEDWDKPE

241 HIPDPDAKKP EDWDEEMDGE WEPPVIQNPE YKGEWKPRQI DNPDYKGTWI HPEIDNPEYS

301 PDPSIYAYDN FGVLGLDLWQ VKSGTIFDNF LITNDEAYAE EFGNETWGVT KAAEKQMKDK

361 QDEEQRLKEE EEDKKRKEEE EAEDKEDDED KDEDEEDEED KEEDEEEDVP GQAKDEL    417
```

Pharmaceutically acceptable carriers and formulations for nucleic acids, peptides and polypeptides are known to the skilled artisan and are described in detail in the scientific and patent literature, see e.g., the latest edition of Remington's Pharmaceutical Science, Maack Publishing Company, Easton, Pa. ("Remington's"); Banga; Putney (1998) Nat. Biotechnol. 16:153-157; Patton (1998) Biotechniques 16:141-143; Edwards (1997) Science 276: 1868-1871; U.S. Pat. Nos. 5,780,431; 5,770,700; 5,770,201.

The nucleic acids and polypeptides used in the methods of the invention can be delivered alone or as pharmaceutical compositions by any means known in the art, e.g., systemically, regionally, or locally; by intraarterial, intrathecal (IT), intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa). Actual methods for delivering compositions will be known or apparent to those skilled in the art and are described in detail in the scientific and patent literature, see e.g., Remington's.

The pharmaceutical compositions can be administered by any protocol and in a variety of unit dosage forms depending upon the method and route and frequency of administration, whether other drugs are being administered, the individual's response, and the like. Dosages for typical nucleic acid, peptide and polypeptide pharmaceutical compositions are well known to those of skill in the art. Such dosages may be adjusted depending on a variety of factors, e.g., the initial responses (e.g., number and activity of CTLs induced, tumor shrinkage, and the like), the particular therapeutic context, patient health and tolerance. The amount of pharmaceutical composition adequate to induce the desired response is defined as a "therapeutically effective dose." The dosage schedule and amounts effective for this use, i.e., the "dosing regimen," will depend upon a variety of factors, including, e.g., the diseases or conditions to be treated or prevented by the immunization, the general state of the patient's health, the patient's physical status, age, pharmaceutical formulation and concentration of pharmaceutical composition, and the like. The dosage regimen also takes into consideration pharmacokinetics, i.e., the pharmaceutical composition's rate of absorption, bioavailability, metabolism, clearance, and the like (Remington). Dosages can be determined empirically, e.g., by assessing the abatement or amelioration of symptoms, or, by objective criteria, e.g., measuring levels of antigen-specific CTLs. As noted above, a single or multiple administrations can be administered depending on the dosage and frequency as required and tolerated by the patient. The pharmaceutical compositions can be administered alone or in conjunction with other therapeutic treatments, or, as prophylactic immunization.

Ex vivo Treatment and Re-administration of APCs

In various embodiments of the invention, the nucleic acids and polypeptides of the invention are introduced into the individual by ex vivo treatment of antigen presenting cells (APCs), followed by administration of the manipulated APCs. In one embodiment, APCs are transduced (transfected) or infected with fusion protein-encoding nucleic acids of the invention; afterwards, the APCs are administered to the individual. In another embodiment, the APCs are stimulated with fusion proteins of the invention (purified or as a cell lysate from cells transfected and expressing a recombinant fusion protein in vivo). Afterward this "pulsing, the APCs are administered to the individual.

The fusion proteins can be in any form, e.g., as purified or synthetic polypeptides, as crude cell lysates (from transfected cells making recombinant fusion protein), and the like. The APC can be an MHC-matched cell (a tissue-typed cell). The APC can be a tissue-cultured cell or it can be an APC isolated from the individual to be treated and re-administered after ex vivo stimulation. Any APC can be used, as described above. Methods of isolating APCs, ex vivo treatment in culture, and re-administration are well known in the art (U.S. Pat. Nos. 5,192,537; 5,665,350; 5,728,388; 5,888,705; 5,962,320; 6,017,527; 6,027,488).

Kits

The invention provides kits that contain the pharmaceutical compositions of the invention, as described above, to practice the methods of the invention. In alternative embodiments, the kits can contain recombinant or synthetic chimeric polypeptides comprising a first domain comprising an ER chaperone polypeptide and a second domain comprising an antigenic peptide, e.g., a CRT-Class I-binding peptide epitope fusion protein; or, the nucleic acids encoding them, e.g., in the form of naked DNA (e.g., plasmids), viruses (e.g. alphavirus-derived "replicons" including Sindbis virus replicans) and the like. The kit can contain instructional material teaching methodologies, e.g., means to administer the compositions used to practice the invention, means to inject or infect cells or patients or animals with the nucleic acids or polypeptides of the invention, means to monitor the resultant immune response and assess the reaction of the individual to which the compositions have been administered, and the like.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Administration of CRT-Class I-Binding Peptide Epitopes Enhance Generation of an Antigen-specific Cytotoxic T Lymphocyte (CTL) Response The following example describes studies which demonstrate that the compositions and methods of the invention are effective for enhancing antigen-specific cytotoxic T lymphocyte (CTL) responses.

These studies used a DNA vaccine comprising encoding sequence for the fusion protein including both calreticulin (CRT) and a Class I polypeptide-binding peptide epitope, wherein the epitope was a model antigen, the human papilloma virus-16 E7 polypeptide (HPV-16 E7). The anti-tumor effects mediated by E7-specific immune responses and the vaccine-stimulated anti-angiogenesis effects in vaccinated mice were evaluated. C57BL/6 mice that were vaccinated intradermally with DNA vaccines comprising chimeric calreticulin/E7 (CRT/E7) fusion genes exhibited dramatically increased E7-specific CD8+ T cell (CTL) precursors, tumor protection, and tumor treatment compared to DNA vaccines containing wild-type E7 or CRT genes alone. Furthermore, treatment of C57BL/6 mice or nude mice with either CRT DNA or chimeric CRT/E7 DNA led to reduction of lung metastatic nodules and inhibition of angiogenesis within the lung nodules. These results indicate that the linkage of the CRT gene to an antigen gene may greatly enhance the potency of DNA vaccines to elicit anti-tumor effects through both a significant enhancement of antigen-specific CD8+ T cell (CTL) immune responses and anti-angiogenesis effects.

Plasmid DNA Constructs and Preparation: The generation of HPV-16 E7-expressing pcDNA3 plasmid was done as described by Chen (2000) Cancer Res. 60:1035-1042; see also Chen (2000) Vaccine 18:2015-2022; Ji (1999) Hum. Gene Ther. 10:2727-2740; Chen (1999) Gene Ther. 6:1972-1981; Ji (1998) Int. J. Cancer 78:41-45. See also, e.g., Seedorf (1987) EMBO J. 6:139-144; U.S. Pat. Nos. 5,629,161; 5,501,947; 5,547,846; 5,180,806; 4,777,239. See GenBank Accession No. AF125673 (Jun. 1, 1999) describing the complete HPV-16 genome and the HPV-16 E7 protein, having the sequence

MHGDTPTLHEYMLDLQPETTDLYCYEQLNDSSEEED    (SEQ ID NO:5)

EIDGPAGQAEPDPRAHYNIVTFCCKCDSTLRLCVQS

THVDIRTLEDLLMGTLGIVCPICSQKP

For the generation of plasmid encoding the full length of rabbit calreticulin (there is more than 90% homology between rabbit, human, mouse, and rat calreticulin), pcDNA3-CRT, the DNA fragment encoding this protein was first amplified with PCR using conditions as described in Chen (2000) Cancer Res., supra, using rabbit calreticulin cDNA template (Michalak (1999) Biochem J. 344 Pt 2:281-292), provided by Dr. Marek Michalak, University of Alberta, Edmonton, Canada, and a set of primers: 5'-ccggtctagaatgct-gctccctgtgccgct-3' (SEQ ID NO:6) and (SEQ ID NO:7) 5'-ccggagatctcagctcgtccttggcctggc-3'. The amplified product was then digested with the restriction digest enzymes XbaI and BamHI and further cloned into the XbaI and BamHI cloning sites of pcDNA3 vector (Invitrogen, Carlsbad, Calif.). For the generation of pcDNA3-CRT/E7, the E7 DNA was amplified by PCR using pcDNA3-E7 as a DNA template and a set of primers: 5'-ggggaattcatggagataccta-3' (SEQ ID NO:7) and 5'-ggtggatccttgagaacagatgg-3' (SEQ ID NO:8). The amplified E7 DNA fragment was then digested with BamHI and further cloned into the BamHI cloning sites of pcDNA3-CRT vector. The orientation and accuracy of these constructs was confirmed by DNA sequencing.

Plasmid DNA with CRT, E7 or CRT/E7 gene insert and the "empty" plasmid vector were transfected into subcloning-efficient DH5™ cells (Life Technologies, USA). The DNA was then amplified and purified using double CsCl purification (BioServe Biotechnologies, Laurel, Md.). The integrity of plasmid DNA and the absence of *Escherichia coli* DNA or RNA were checked in each preparation using 1% agarose gel electrophoresis. DNA concentration was determined by the optical density, measured at 260 nm. The presence of inserted E7 fragment was confirmed by restriction enzyme digestion and gel electrophoresis.

Cell Lines: The production and maintenance of TC-1 cells was done as described in Lin (1996) Cancer Res. 56:21-26. On the day of tumor challenge, TC-1 cells were harvested by trypsinization, washed twice with 1× Hanks buffered salt solution (HBSS) and finally resuspended in 1×HBSS to the designated concentration for injection. A human embryonic kidney 293 cell line expressing the $D^b$ and $K^b$ (293 $D^b$, $K^b$) (Bloom (1997) J. Exp. Med. 185:453-459) was provided by Dr. J C Yang (NCI, NIH, Bethesda, Md.). It was grown in DMEM medium containing 10% heat-inactivated fetal calf serum, 0.3% glutamine, 0.01 M HEPES, 100 U/ml penicillin, 100 µg G418.

Mice: 6-to 8-week-old female C57BL/6 mice from the National Cancer Institute (Frederick, Md.) were purchased and kept in the oncology animal facility of the Johns Hopkins Hospital (Baltimore, Md.). To characterize the effect of anti-angiogenesis, in vivo tumor treatment experiments in the absence of immune effectors were conducted using BALB/c nu/nu 6-week old female mice from the National Cancer Institute (Frederick, Md.). All animal procedures were performed according to approved protocols and in accordance with recommendations for the proper use and care of laboratory animals.

DNA Vaccination: Preparation of DNA-coated gold particles and gene gun particle-mediated DNA vaccination was performed using a helium-driven gene gun (Bio-Rad, Hercules, Calif.) according as described by Chen (2000) Cancer Res., supra. Briefly, DNA coated gold particles (1 or 4 µg DNA/bullet) were delivered to the shaved abdominal region of the mice using the helium-driven gene gun with a discharge pressure of about 400 p.s.i.

Intracytoplasmic Cytokine Staining and Flow Cytometry Analysis: Splenocytes from naive or vaccinated groups of mice were incubated either with the E7 peptide (amino acid (aa) residues 49 to 57) that contains MHC class I epitope (Feltkamp (1993) Eur. J. Immunol. 23:2242-2249) for detecting E7-specific CD8+ T cell precursors, or, the E7 peptide (aa 30 to 67) that contains MHC class II peptide (Tindle (1991) Proc. Natl. Acad. Sci. USA 88:5887-5891) for detecting E7-specific CD4+ T helper cell precursors. The E7 peptide was added at a concentration of 1 µg/ml for aa 49-57 and 10 µg/ml for aa 30-67 for 20 hours. Golgistop™ (Pharmigen, San Diego, Calif.) was added 6 hours before harvesting the cells from the culture. Cells were then washed once in FACScan™ buffer and stained with phycoerythrin (PE)-conjugated monoclonal rat anti-mouse CD8 or CD4 antibody (PharMingen, San Diego, Calif.). Cells were subjected to intracellular cytokine staining using the Cytofix/Cytoperm™ kit according to the manufacturer's instructions (PharMingen). FITC-conjugated anti-IFN-gamma and anti-IL4 antibodies and the immunoglobulin isotype control antibody (rat IgG1) were all purchased from PharMingen. Flow cytometry analysis was performed on a Becton Dickinson FACScan™ with CELLQuest™ software (Becton Dickinson Immunocytometry System, Mountain View, Calif.).

ELISA for anti-E7 Antibody: Anti-HPV 16 E7 antibodies in the sera were determined by a direct ELISA as described by Wu (1995) Proc. Natl. Acad. Sci. USA 92:11671-11675. Briefly, a 96-microwell plate was coated with 10.5 µg/ml bacteria-derived HPV-16 E7 proteins and incubated at 40° C. overnight. The wells were then blocked with PBS containing 20% fetal bovine serum. Sera were prepared from the mice on day 14 post-immunization, serially diluted in 1×PBS, added to the ELISA wells, and incubated at 37° C. for 2 hr. After washing with 1×PBS containing 0.05% Tween-20, the plate was incubated with 1/2000 dilution of a peroxidase-conjugated rabbit anti-mouse IgG antibody (Zymed, San Francisco, Calif.) at room temperature (RT) for one hour. The plate was washed 6 times, developed with TMB (Pierce, Rockford, Ill.), and stopped with 1M $H_2SO4$. The ELISA plate was read with a standard ELISA reader at 450 nm.

In Vivo Tumor Protection Experiments: For the tumor protection experiment, mice (5 per group) were vaccinated via gene gun with 2 µg of CRT DNA, E7 DNA, CRT/E7 DNA or unvaccinated. One week later, the mice were boosted with the same regimen as the first vaccination. One week after the last vaccination, mice were subcutaneously challenged with $5 \times 10^4$ TC-1 cells/mouse in the right leg. Mice were monitored for evidence of tumor growth by palpation and inspection twice a week until they were sacrificed at day 60.

In Vivo Tumor Treatment Experiments: C57BL/6 Mice (5 each group) were intravenously challenged with $1 \times 10^4$ cells/mouse TC-1 tumor cells via tail vein on day 0. Three days after challenge with TC-1 tumor cells, mice were given 2 μg of CRT DNA, E7 DNA, CRT/E7 DNA via gene gun or unvaccinated. One week later, these mice were boosted with the same regimen as the first vaccination. Mice were monitored twice a week and sacrificed on day 21. The number of pulmonary metastatic nodules of each mouse was evaluated and counted by experimenters blinded to the sample identity.

Nude (BALB/c nu/nu) mice (5 each group) were intravenously challenged with $1 \times 10^4$ cells/mouse TC-1 tumor cells via tail vein on day 0. Two days (D2) after challenge with TC-1 tumor cells, mice were given 16 μg of CRT DNA, E7 DNA, CRT/E7 DNA, or the empty plasmid without insert via gene gun. On day 9 and day 16, these mice were boosted with the same regimens as the first vaccination. The mice were sacrificed on day 21. The pulmonary nodules of each mouse were evaluated and counted by experimenters blinded to sample identity.

In Vivo Antibody Depletion Experiments: In vivo antibody depletions were done as described by Lin (1996) Cancer Res. 56:21-26. Briefly, mice were vaccinated with 2 μg CRT/E7 DNA via gene gun, boosted one week later, and challenged with $5 \times 10^4$ cells/mouse TC-1 tumor cells. Depletions were started one week prior to tumor challenge. MAb GK1.5 (Dialynas (1983) Immunol. Rev. 74: 29-56) was used for CD4 depletion, MAb 2.43 (Sarmiento (1980) J. Immunol. 125: 2665) was used for CD8 depletion, and MAb PK136 (Koo (1986) J. Immunol. 137:3742-3747) was used for NK1.1 depletion. Flow cytometry analysis revealed that >99% of the appropriate lymphocytes subset were depleted while maintaining normal levels of other subsets. Depletion was terminated on day 40 after tumor challenge.

Generation of Dendritic Cells: Dendritic cells (DCs) were generated by culture of bone marrow cells in the presence of GM-CSF as described by Fernandez (1999) Nat. Med. 5:405-411). Briefly, bone marrow was collected from the femurs and tibias of mice. Erythrocytes were lysed, and the remaining cells were passed through a nylon mesh to remove small pieces of bone and debris. The cells were collected and 1×106 cells/ml were placed in 24-well plates in RMPI 1640, supplemented with 5% FCS, 2 mM (-mercaptoethanol, 1% nonessential amino acids, 100 U/ml penicillin and 100 (g/ml streptomycin (Life Technologies, Rockville, Md.), and 100 U/ml GM-CSF (PharMingen, San Diego, Calif.). Two-thirds of the medium was replaced every 2 days, and non-adherent cells were harvested on day 7. The collected cells were characterized using flow cytometry analysis for DC markers as previously described (25).

Generation of E7-Specific CD8+ T Cell Lines: E7-specific CD8+ cell lines were generated by immunizing female C57BL/6 (H-2b) mice by intraperitoneal injection of vaccinia E7 expressing expression vector (a lysosome-associated membrane protein 1 (LAMP-1) coding sequence was fused to HPV-E7 coding sequence to construct a chimeric DNA, designated Sig/E7/LAMP-1, as discussed by Ji (1999) Hum. Gene Ther. 10:2727-2740). Splenocytes were harvested on day 8. For initial in vitro stimulation, splenocytes were pulsed with IL-2 at a concentration of 20 U/ml and 1 TM E7 peptide (amino acids 49-57 of SEQ ID NO:4) for 6 days. Propagation of the E7-specific CTL cell line was performed in 24-well plates by mixing (2 ml/well) $1 \times 10^6$ splenocytes containing E7-specific CTLs with $3 \times 10^6$ irradiated splenocytes and pulsing them with IL-2 at a concentration of 20 U/ml and 1 ™ E7 peptide (amino acids 49-57). This procedure was repeated every 6 days. The specificity of the E7 CTL line was characterized by the CTL assay. Flow cytometry was performed to demonstrate the expression of the CD8 marker.

CTL Assay using Transfected 293 $D^b$ $K^b$ Cells as Target Cells: CTL assays were performed in 96-well round-bottom plates as described by Corr (1999) J. Immunol. 163:4721-4727. Cytolysis was determined by quantitative measurements of lactate dehydrogenase (LDH). Transfected 293 $D^b$ $K^b$ cells were used as target cells while E7-specific CD8+ T cells served as effector cells. $5 \times 10^6$ 293 $D^b$ $K^b$ cells were transfected with 20 Tg of pcDNA3 (empty plasmid), E7, CRT, or CRT/E7 DNA vaccines via lipofectamine 2000™ (Life Technologies, Rockville, Md.) according to manufacturer's protocol. The 293 $D^b$ $K^b$ cells were collected 40-44 hr after transfection. The levels of E7 protein expression as determined by ELISA were similar in E7 and CRT/E7 transfected 293 $D^b$ $K^b$. CTL assays were performed with effector cells and targets cells ($1 \times 10^4$ per well) mixed together at various ratios (1:1, 3:1, 9:1, and 27:1) in a final volume of 200 T1. After a 5 hr incubation at 37° C., 50 T1 of the cultured media were collected to assess the amount of LDH in the cultured media using CytoTox™ assay kits (Promega, Madison, Wis.) according to the manufacturer's protocol. The percentage of lysis was calculated from the following equation: $100 \times (A-B)/(C-D)$ where A is the reading of experimental-effector signal value, B is the effector spontaneous background signal value, C is maximum signal value from target cells, D is the target spontaneous background signal value.

CTL Assay Using DCs Pulsed with Lysates of Transfected 293 Cells as Target Cells: CTL assays using dendritic cells (DCs) pulsed with cell lysates as target cells were performed using a protocol similar to that described by Uger (1998) J. Immunol. 160:1598-1605. Briefly, $5 \times 10^6$ 293 $D^b$ $K^b$ cells were first transfected with 20 Tg of pcDNA3 (empty plasmid), E7, CRT, or CRT/E7 DNA vaccines via lipofectamine 2000™ (Life Technologies, Rockville, Md.) according to manufacturer's protocol. The transfected 293 $D^bK^b$ cells were collected 40-44 hr after transfection and then treated with three cycles of freeze-thaw. The protein concentration was determined using the BioRad protein assay (Bio-Rad, Hercules, Calif.) according to vendor's protocol. The quantity of E7 protein was determined using ELISA and the cell lysates from E7 or CRT/E7 DNA transfected 293 $D^bK^b$ cells were standardized for E7 protein concentration. The DCs were used as target cells and prepared by pulsing 1 million DCs with different concentrations of cell lysates (50 Tg/ml, 10 Tg/ml, 2 Tg/ml and 0.4 Tg/ml) in a final volume of 2 ml for 16-20 hrs. E7-specific CD8+ T cells were used as effector cells. CTL assays was performed at fixed E/T (9/1) ratio with $9 \times 10^4$ of E7-specific T cells mixed with $1 \times 10^4$ of prepared DCs in a final volume of 200 Tl. Cytolysis was determined by quantitative measurements of LDH as described above.

Histologic and immunohistochemical studies: Paraffin blocks of the lung nodules from vaccinated mice were generated and sectioned in 6 Tm slices and deparaffinized. Hematoxylin and eosin staining was performed for routine light microscopic examination and unstained sections were prepared for immunohistochemical study. Mouse anti-CD31 monoclonal antibodies (DAKO, Capinteria, Calif.) were used for the detection of intratumoral microvessels. Immunohistochemical staining was performed on the sections from both specimens using the protocol as described by Huang (1999) Hum. Pathol. 30: 587-591. Microvessel density (MVD) was measured as described by Cheng (1999) Cancer 85:651-657. Briefly, stained slides were examined at low-power magnification (40× and 100× total magnification) to identify the areas of highest neovascularization (so-call hot spots) in each tumor. In each section, the three most vascularized areas were chosen. Microvessel counts were obtained at 200× magnification (20× objective and 10× ocular (Olympus BH-2 microscope), 0.74 mm² per field with the field size measured with an ocular micrometer) and the mean number in the three fields for each tumor was calculated, referred to as the microvessel density (MVD) count. Large vessels with thick muscular walls and lumina greater than appropriately eight blood cells were excluded from the count. All measurements were performed by a single pathologist blinded to the sample identity.

Generation and Characterization of the CRT/E7 Fusion DNA Vaccine: A schematic diagram of the constructs of calreticulin (CRT), E7, and calreticulin/E7 (CRT/E7) is presented in FIG. 1. All of the constructs have been confirmed by DNA sequencing. To demonstrate the expression of E7 protein in E7-containing constructs, a Western blot analysis using lysates of 293 $D^bK^b$ cells transfected with various E7-containing DNA constructs was performed. 293 $D^bK^b$ cells transfected with wild-type E7 showed a 30 kD band corresponding to HPV-16 E7. In addition, 293 $D^bK^b$ cells transfected with CRT/E7 showed a band corresponding to chimeric CRT/E7 protein. No visible bands were observed in the negative controls, 293 $D^bK^b$ transfected with either calreticulin or empty plasmid.

Vaccination with CRT/E7 Fusion DNA Significantly Enhances the Numbers of E7-Specific CD8+ T Cells: CD8+ T lymphocytes (CTLs) are one of the most crucial effectors for inducing anti-tumor immunity. To determine the quantity of E7-specific CD8+ T cell precursors induced after in vivo administration (to mice) of the CRT/E7 DNA vaccine of the invention, intracellular cytokine staining was used as described by Ji (1999) Human Gene Therapy 10:2727-2740. Intracellular cytokine staining is a sensitive functional assay used to measure IFN-gamma (IFN-K) production at the single-cell level, which can thus be applied to quantify antigen-specific CD8+ T cells. The results of the flow cytometry analysis (performed as discussed above) is shown in the two-dimensional histogram in FIG. 2A. As summarized in FIG. 2B, mice vaccinated with CRT/E7 DNA induced the highest number of E7-specific IFN-gamma expressing/CD8+ T cell precursors (204/3.5×10⁵ splenocytes), whereas mice vaccinated with E7 DNA induced fewer precursors (47/3.5×10⁵ splenocytes) (p<0.01). CRT/E7 chimeric construct immunization led to a 5-fold increase in the number of E7-specific CD8+ T cell precursors. These results also indicated that fusion of E7 to CRT (i.e., expression as a fusion protein) was required for enhancement of CD8+ T cell activity, since vaccination with two vectors, one expressing only CRT mixed with one expressly only E7 ("CRT+E7" on FIG. 2B) did not induce enhancement of CD8+ T cell activity.

Vaccination with CRT/E7 Fusion DNA Does Not Enhance E7-Specific CD4+ T Cell-Mediated Immune Responses: To examine the generation of E7-specific CD4+ ("helper") T percolator cells and cytokine profiles induced by each of these vaccines, we performed double staining for CD4 surface marker and intracellular IFN-K+ on splenocytes from immunized mice, followed by flow cytometry analysis. The splenocytes from immunized mice were cultured in vitro with E7 peptide (aa 30-67) overnight and stained for both CD4 and intracellular IFN-K+. The E7 peptide (aa 30-67) contains a major T helper epitope in the E7 open reading frame protein of HPV-16 (Tindle (1991) Proc Natl. Acad. Sci. USA 88:5887-5891. The percentage of IFN-K+ secreting CD4+ T cells was analyzed using flow cytometry. Mice vaccinated with CRT/E7 chimeric constructs induced a similar number of CD4+ IFNK+double positive cells compared to mice vaccinated with wild-type E7 DNA (25/3.5×10⁵ splenocytes versus 20/3.5×10⁵ splenocytes, p>0.05) or other DNA groups. There was no significant difference in the number of E7-specific CD4+ IFNK+ cells observed using flow cytometry staining among naive mice or mice vaccinated with empty plasmid, CRT, E7, CRT+E7, or CRT/E7 constructs.

The numbers of IL-4-secreting E7-specific CD4+ T cells in mice vaccinated with various DNA vaccines was also assessed. IL-4-secreting activated mouse splenocytes (MiCK-2™, PharMingen, San Diego, Calif.) were used as positive controls to ensure the success of intracellular IL-4 staining for this study. The specificity of the IL-4 staining was demonstrated by the absence of CD4+ IL-4+ T cells when the IL-4 antibody was omitted. No significant CD4+ IL-4+ double-positive cells were identified in mice vaccinated with CRT/E7, CRT, wild type E7 DNA, plasmid DNA vaccination or in naive mice without vaccination. In addition, no significant variation was observed in the frequency of IL-4-secreting CD4+ IL-4+ T cells from the different vaccination groups.

Figure 3:
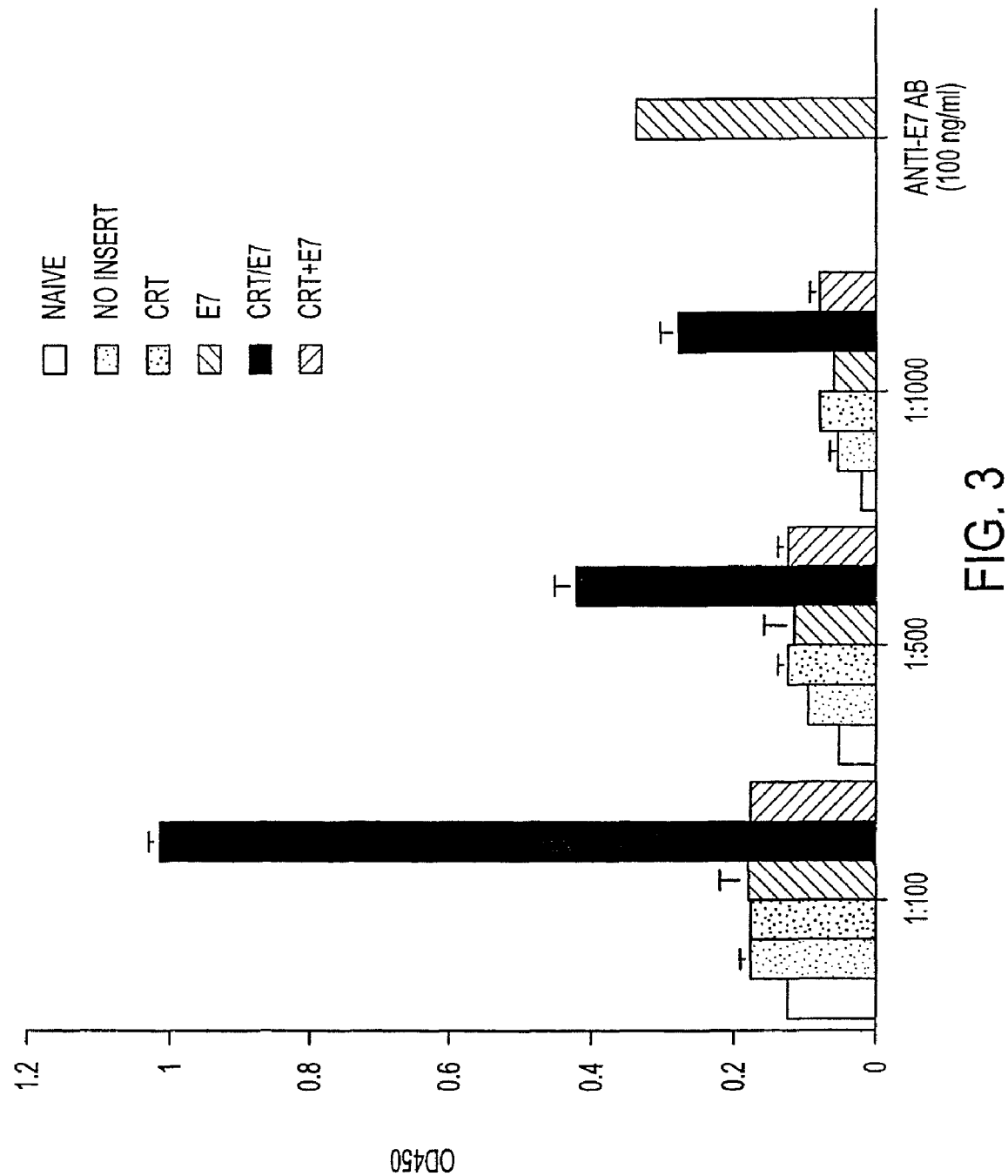
FIG. 3 shows a schematic summary of data showing the quantity of anti-HPV 16 E7 antibodies in the sera of vaccinated mice as determined by a direct ELISA two weeks after the last vaccination with construct only and constructs encoding CRT alone, E7 alone, CRT/E7 fusion protein, and, a mixture of two construct expressing CRT and E7 individually, as discussed in Example 1, below.

Vaccination with CRT/E7 Induced Higher Titers of E7-Specific Antibodies: The quantity of anti-HPV 16 E7 antibodies in the sera of vaccinated mice was determined by a direct ELISA two weeks after the last vaccination. As shown in FIG. 3, the CRT/E7 vaccinated group induced the highest titers of anti-E7 antibodies in the sera of mice compared to the other vaccinated groups (P<0.01). This result showed that mice vaccinated with CRT/E7 chimeric construct of the invention induced significantly higher E7-specific antibody responses.

Figure 4:
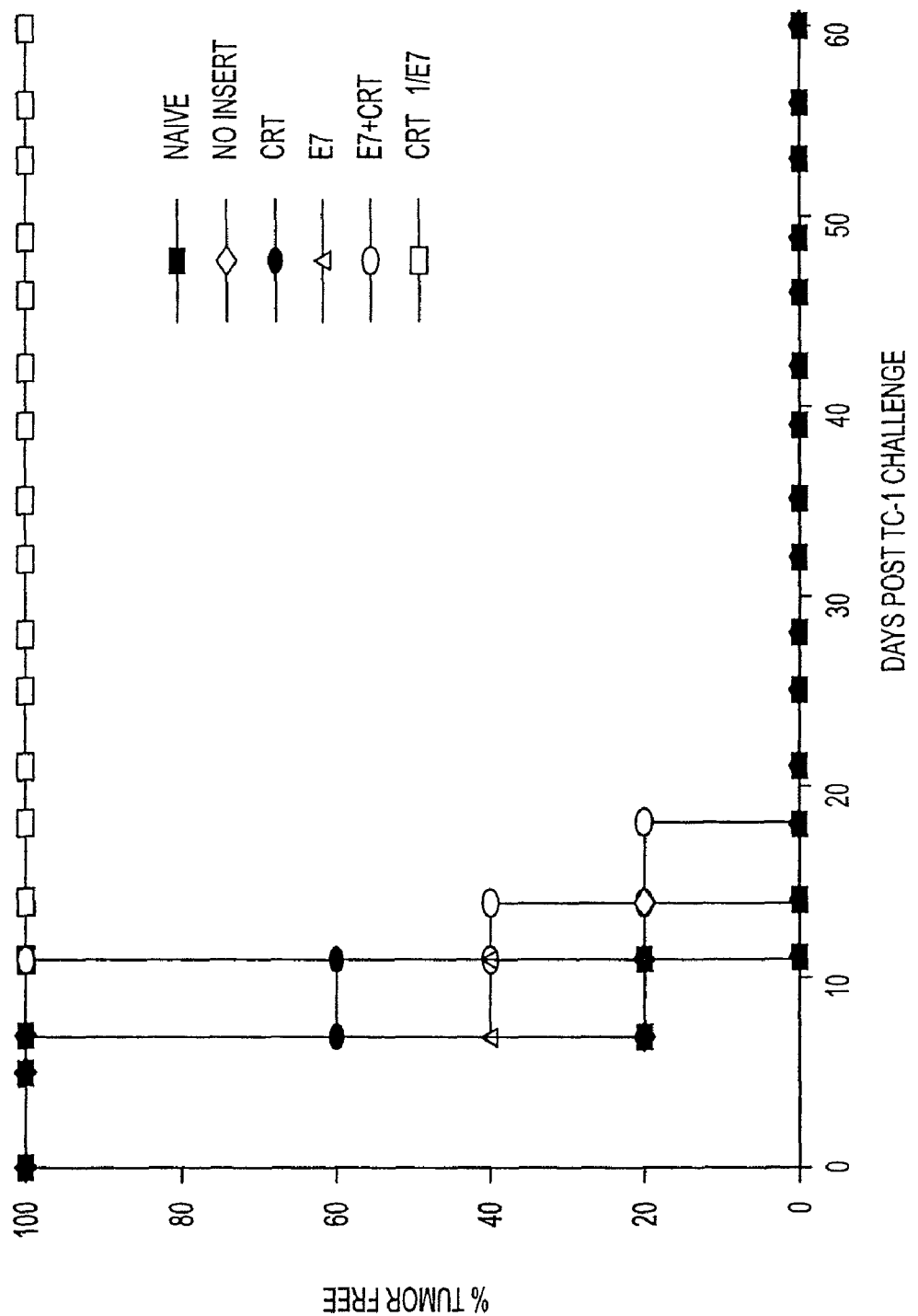
FIG. 4 shows a schematic summary of in vivo tumor protection experimental data in which mice were vaccinated with various DNA vaccine constructs and later challenged with E7-expressing tumor, as discussed in Example 1, below.

Vaccination with CRT/E7 Chimeric Construct Enhances Protection of Mice Against the Growth of TC-1 Tumors: To determine whether vaccination with the various DNA vaccine constructs protects mice against E7-expressing tumors, in vivo tumor protection experiments were performed. Mice were vaccinated with 2 Tg naked DNA/mouse via gene gun and boosted with the same dose one week later. Mice were then challenged with 5×10⁴ TC-1/mouse subcutaneously in the right leg 7 days after the last vaccination. As shown in FIG. 4, 100% of those receiving CRT/E7 chimeric construct vaccination remained tumor-free 60 days after TC-1 challenge. In contrast, all of the unvaccinated mice and mice receiving empty plasmid, CRT, wild-type E7, or wild type E7+CRT DNA developed tumor growth within 15 days after tumor challenge. These results also indicated that fusion of E7 to calreticulin was required for antitumor immunity, since constructs expressing only calreticulin mixed with constructs expressing only E7 ("CRT+E7" in FIG. 4) does not induce enhancement of antitumor immunity. Therefore, the CRT/E7 chimeric constructs of the invention significantly enhanced protection against the growth of TC-1 tumors.

Figure 5:
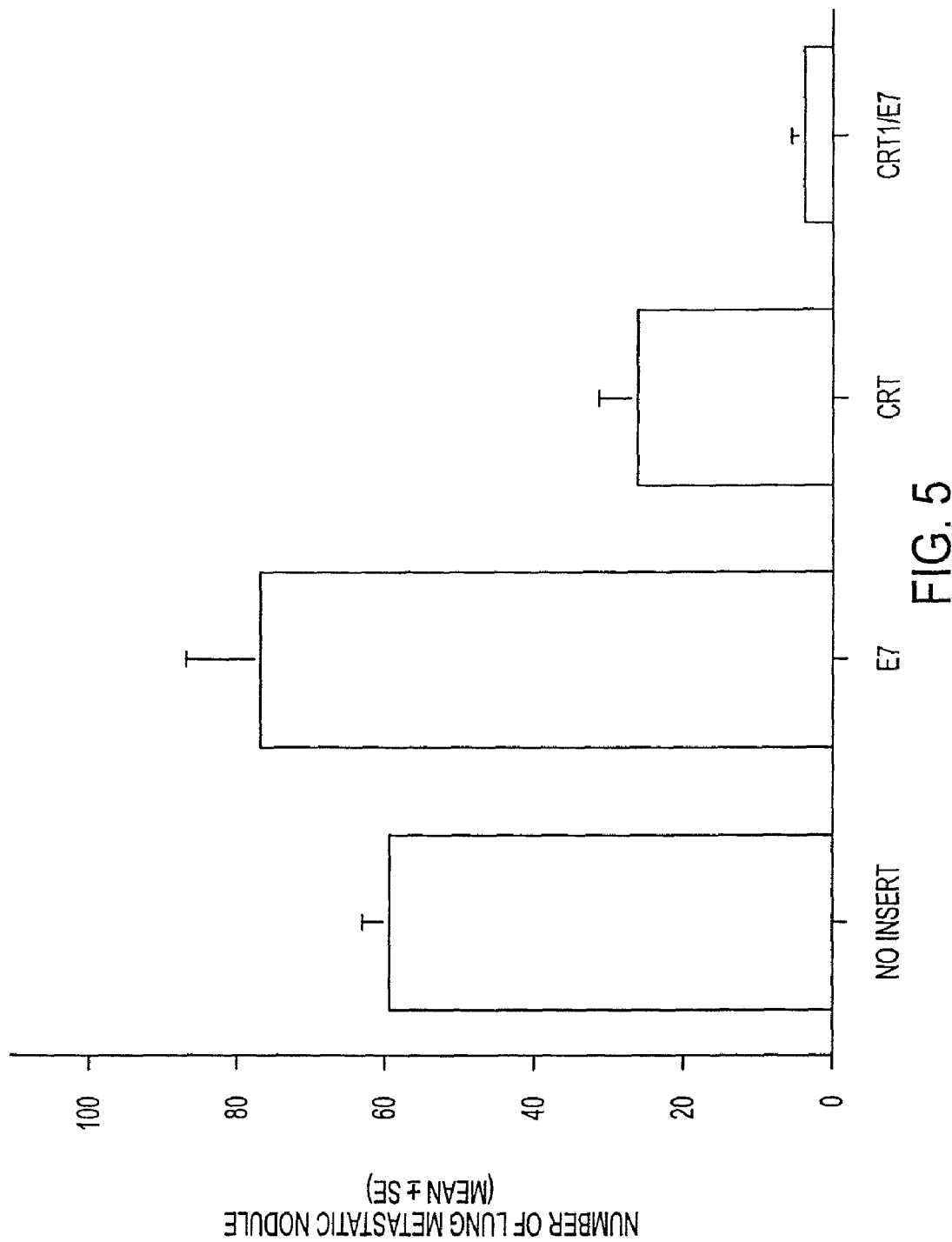
FIG. 5 shows a schematic summary of data from experiments in which mice were first injected with tumor cells, followed by vaccination with various naked DNA constructs (including a one week booster after day 1 of vaccination); thereafter the mean number of pulmonary nodules was assessed; data are expressed as mean number of pulmonary metastatic tumor nodules +SEM as a function of days post tumor cell challenge, as discussed in Example 1, below.

Vaccination with CRT/E7 Chimeric Construct Eradicates Established E7-expressing Tumors in the Lungs: To determine the therapeutic potential of a chimeric CRT/E7 DNA construct in treating TC-1 tumor metastases in the lungs, C57BL/6 mice were first challenged with 1×10⁴ TC-1 tumor cells per mouse via intravenous tail vein injection (lung metastasis model) Ji (1998) Int. J. Cancer 78:41-45. Mice were then treated with 2 Tg naked DNA via gene gun seven days later and boosted with the same dose 1 week later. Mice were then sacrificed 30 days after tumor challenge. As shown in FIG. 5, mice vaccinated with CRT/E7 chimeric construct revealed the lowest mean number of pulmonary nodules (4.0+1.6) compared to mice vaccinated with wild-type E7 DNA only (77.6+9.8), or calreticulin DNA only (26.4+4.9) (one-way ANOVA, P<0.001). Data are expressed as mean number of pulmonary metastatic tumor nodules +SEM. Interestingly, mice vaccinated with wild-type calreticulin DNA displayed a lower mean number of nodules than mice receiving wild-type E7 DNA or no vaccination (one-way ANOVA, P<0.001). Since mice vaccinated with CRT alone did not induce E7-specific T cell immune responses, the therapeutic effects (lower number of lung metastatic nodules) observed with CRT alone may be caused by a CRT-mediated anti-angiogenesis effect.

CD8+ T Cells But Not CD4+ T cells or NK cells are Essential for the Anti-tumor Effect Induced by the CRT/E7 Chimeric DNA Vaccine of the Invention: To determine the subset of lymphocytes that are important for the rejection of E7-positive tumor cells, we performed in vivo antibody depletion experiments. Depletion of lymphocyte subsets was assessed on the day of tumor injection, and weekly thereafter by flow cytometry analysis of spleen cells. More than 99% depletion of the appropriate subset was achieved with normal levels of other lymphocyte subsets. All naive mice and all mice depleted of CD8+ T cells grew tumors within about 14 days after tumor challenge. In contrast, all of the non-depleted mice and all of the mice depleted of CD4+ T cells or NK1.1 cells remained tumor-free 60 days after tumor challenge. These results demonstrate that CD8+ T cells are essential for the anti-tumor immunity induced by the CRT/E7 chimeric vaccine of the invention.

Figure 6:
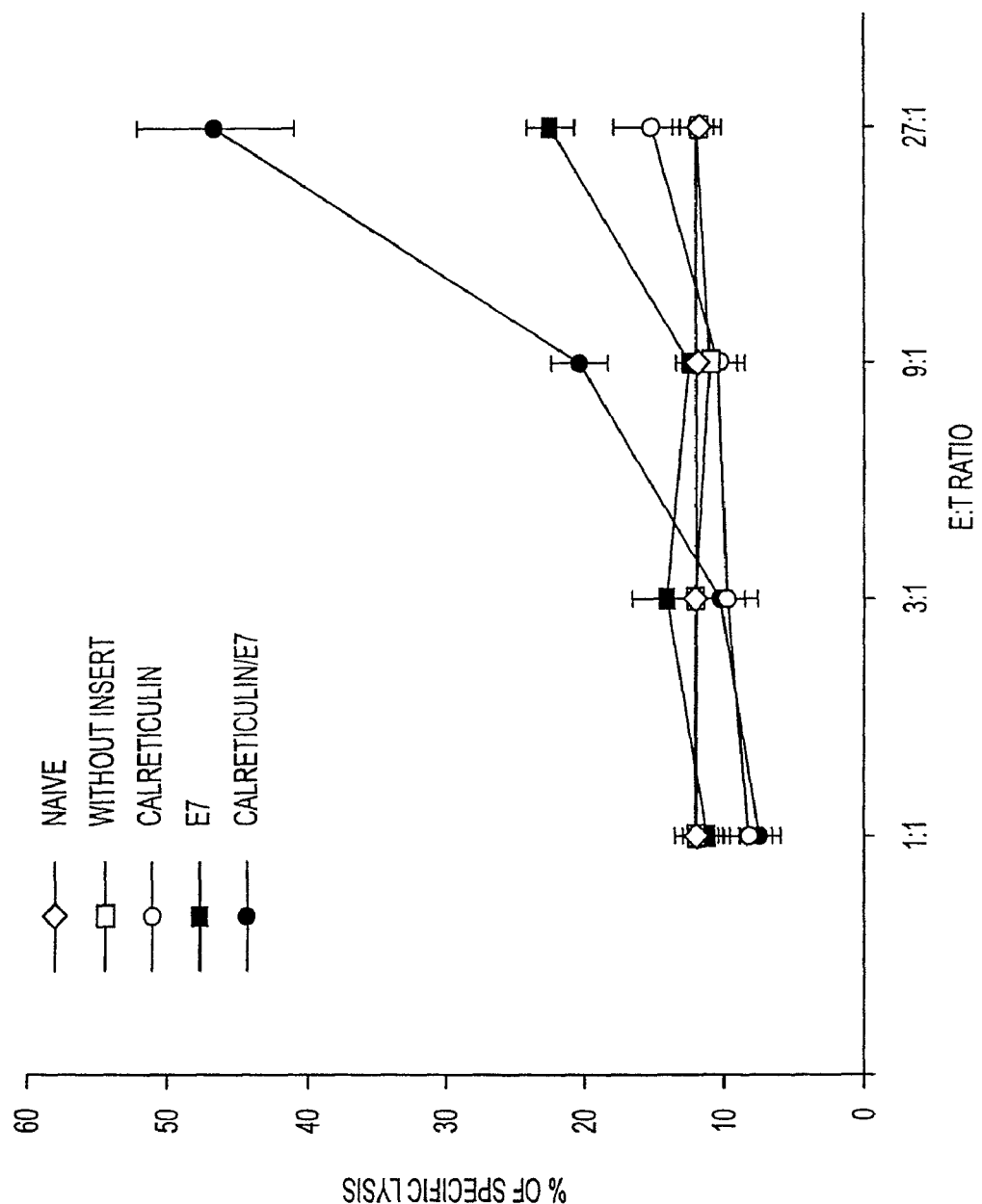
FIG. 6 shows a schematic summary of data of CTL assays using Db-restricted E7-specific CD8+ T cells as effector cells against 293 $D^b K^b$ target cells transfected with various naked DNA constructs, as discussed in Example 1, below.

Enhanced Presentation of E7 Through the MHC Class I Pathway in Cells Transfected with CRT/E7 DNA: As discussed above, mice vaccinated with the CRT/E7 chimeric construct of the invention induced the highest number of E7-specific CD8+ T cell precursors. In order to determine the mechanism that accounted for this effect, it was determined if there was enhanced MHC class I presentation of E7 in target cells, in this case, human embryonic kidney 293 cells expressing Db and Kb transfected with the CRT/E7 fusion protein encoding chimeric DNA. CTL assays with Db-restricted E7-specific CD8+ T cells as effector cells were used to determine if target cells (293 $D^bK^b$ cells) transfected with a CRT/E7 construct can be killed more efficiently than 293 $D^bK^b$ cells transfected with only wild type E7. 293 $D^bK^b$ cells were used as target cells because they have been shown to have stable transfection efficiency, whereas dendritic cells are not transfected as readily in vivo. In addition, the level of E7 expression in 293 $D^bK^b$ cells is similar among cells transfected with different E7-containing DNA constructs. CTL assays were performed using naïve 293 $D^bK^b$ cells and 293 $D^bK^b$ cells transfected with empty plasmid, CRT, E7, or chimeric CRT/E7 DNA with various effector/target (E/T) ratios (1:1, 3:1, 9:1, 27:1) using an E7-specific T cell line. As shown in FIG. 6, 293 $D^bK^b$ cells transfected with CRT/E7 DNA induced significantly higher percentages of specific lysis at the 9:1 (20.5+1.0% versus 10.43+0.9%, P<0.001) and 27:1 (47.1+5.5% versus 15.1+3.0%, P<0.001) E/T ratios compared to mice vaccinated with only wild-type E7 DNA vaccine. These results indicated that cells transfected with the chimeric CRT/E7 constructs of the invention were capable of presenting E7 antigen via "direct priming" through the MHC class I pathway in a more efficient manner than cells transfected with wild-type E7 DNA.

Figure 7:
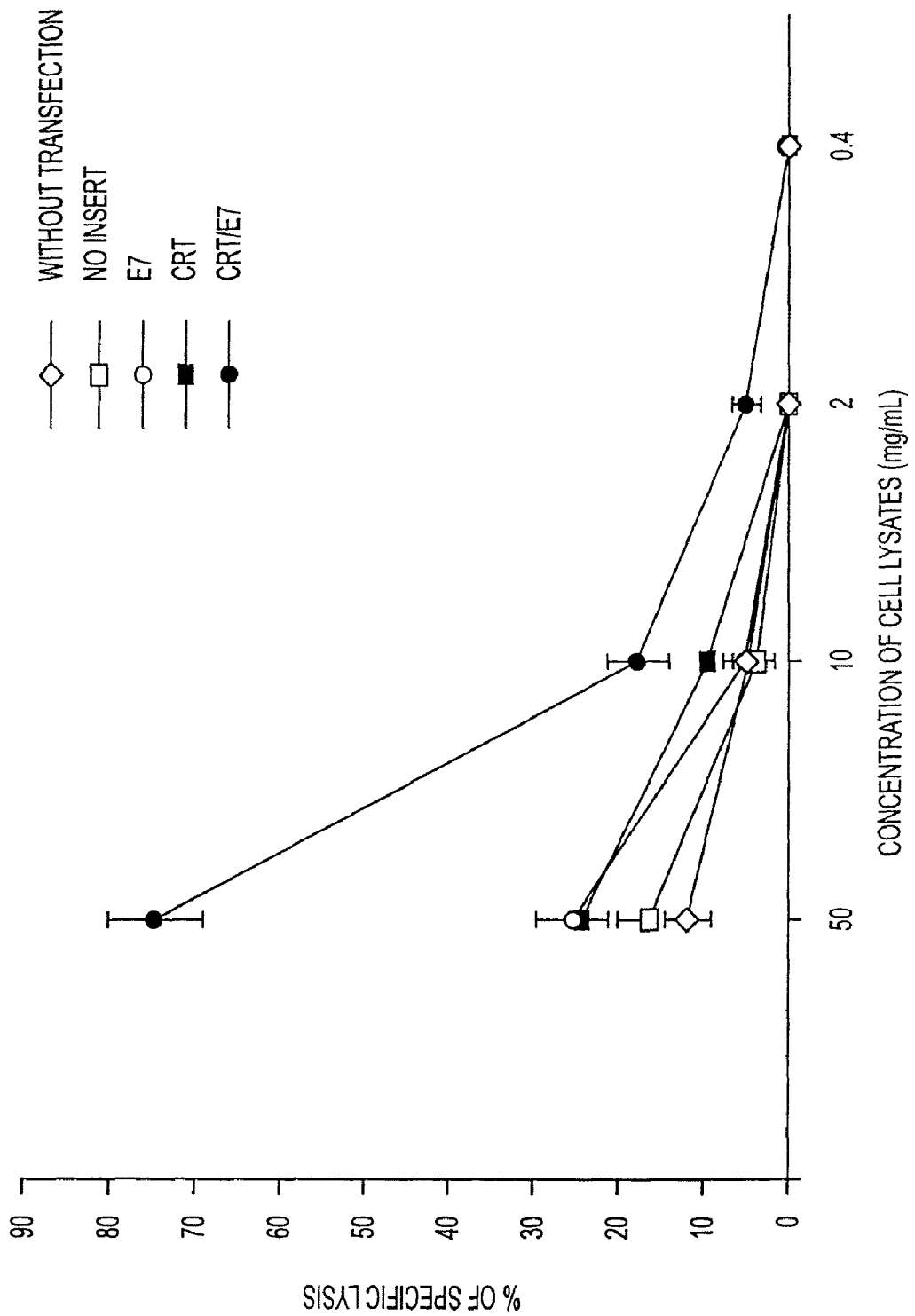
FIG. 7 shows a schematic summary of data from a cross-priming experiment to characterize the MHC class I presentation of E7 dendritic cells pulsed with cell lysates of 293 $D^b K^b$ cells transfected with various naked DNA constructs. E7-specific CD8+ T cells served as effector cells; bone marrow-derived DCs were pulsed with a serial dilution of lysates of transfected 293 $D^b K^b$ cells (50 mg/ml, 10 mg/ml, 2 mg/ml and 0.4 mg/ml); DCs were used as target cells while E7-specific CD8+ T cells served as effector cells as discussed in Example 1, below.

Enhanced Presentation of E7 Through the MHC Class I Pathway in Dendritic Cells Pulsed With Chimeric CRT/E7 Protein: Another potential mechanism for enhanced E7-specific CD8+ T cell immune responses in vivo is the presentation of E7 through the MHC class I pathway by antigen-presenting cells via uptake of lysed cells expressing various DNA constructs, also called "cross-priming". A cross priming experiment was performed to characterize the MHC class I presentation of E7 dendritic cells pulsed with cell lysates of 293 $D^bK^b$ cells transfected with empty plasmid, calreticulin, E7, or CRT/E7 DNA. E7-specific CD8+ T cells served as effector cells. As mentioned previously, 293 $D^bK^b$ cells have been shown to have stable transfection efficiency and similar E7 expression among cells transfected with different E7-containing DNA constructs. Lysates of transfected 293 $D^bK^b$ cells were obtained from cycles of freeze-thaw. Bone marrow-derived DCs were pulsed with a serial dilution of lysates of transfected 293 $D^bK^b$ cells (50 Tg/ml, 10 Tg/ml, 2 Tg/ml and 0.4 Tg/ml). DCs were used as target cells while E7-specific CD8+ T cells served as effector cells. CTL assays were performed with a fixed E/T ratio (9/1). As shown in FIG. 7, DCs pulsed with lysates of 293 $D^bK^b$ cells transfected with CRT/E7 DNA induced significantly higher percentages of specific lysis compared to DCs pulsed with lysates of 293 $D^bK^b$ cells transfected with the other DNA constructs and naive DCs (P<0.001). Theses results revealed that dendritic cells pulsed with CRT/E7 fusion protein (present in the cell lysate of transfected 293 $D^bK^b$ cells) are capable of presenting E7 antigen through the MHC class I pathway in a more efficient manner than dendritic cells pulsed with lysates of 293 $D^bK^b$ cells transfected only with wild-type E7 protein-encoding constructs. This data demonstrates that the fusion of CRT to E7, i.e., expression of the E7 polypeptide as a fusion protein with calreticulin, enhances E7-specific CD8+ T cell immune responses via both direct and cross priming effects.

Figure 8:
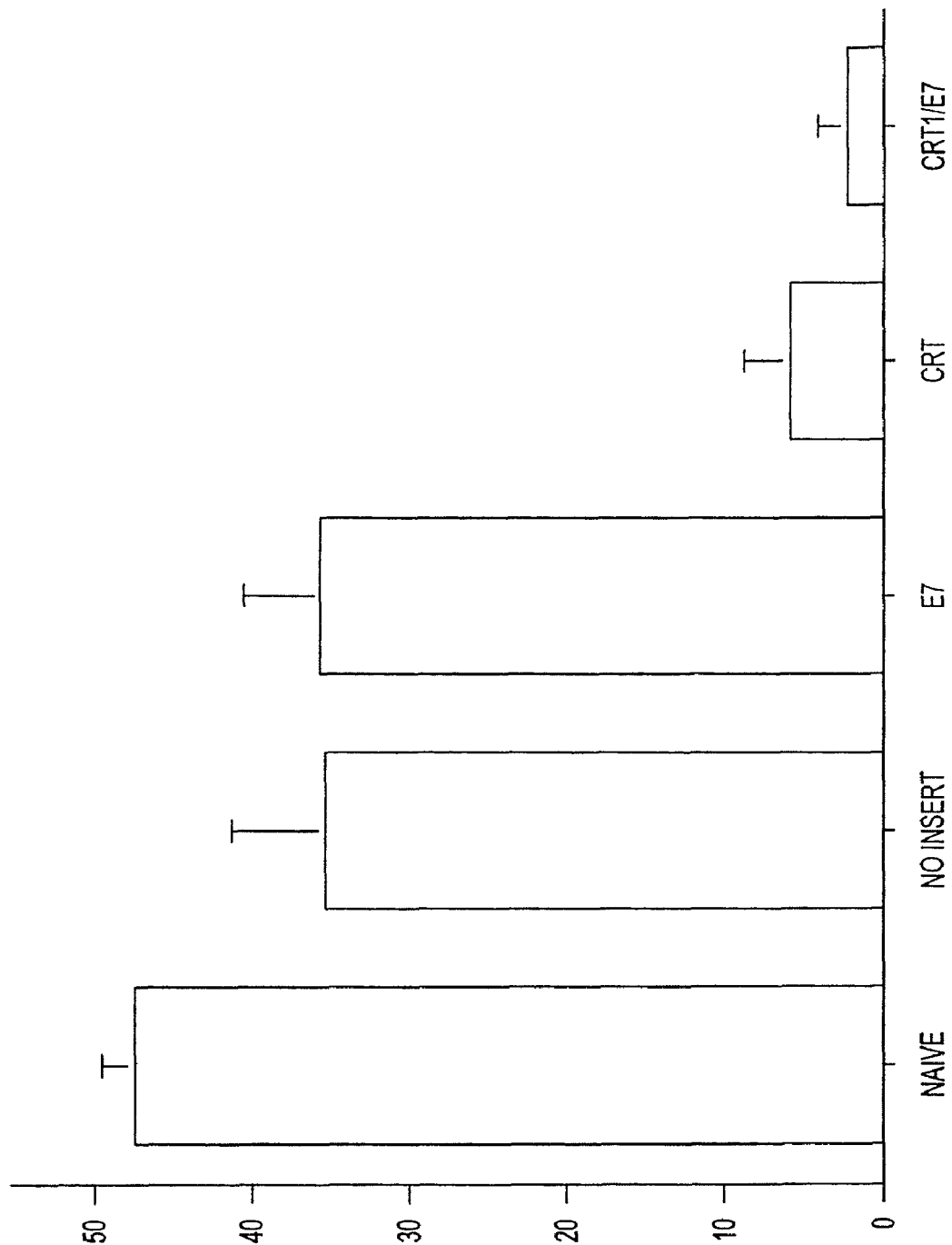
FIG. 8 shows a schematic summary of data from an experiment designed to evaluate the role of CRT/E7 fusion polypeptides as compared to E7 or CRT polypeptide alone in the treatment of TC-1 tumor metastases in the lungs without any immune effector cells (i.e., in nude mice); nude mice were first challenged with tumor cells and two days after challenged with TC-1 tumor cells; thereafter mice were vaccinated with various naked DNA constructs. On day 9 and day 16, these mice were boosted with the same regimen as the first vaccination. The mice were sacrificed on day 21 and the pulmonary nodules of each mouse were evaluated and counted, as discussed in Example 1, below.

Treatment with CRT or Chimeric CRT/E7 DNA Vaccines Eradicates Established Tumors in the Lungs of Nude Mice: As discussed above, mice treated with wild-type CRT DNA displayed a lower mean number of lung nodules than mice receiving only wild-type E7 DNA or no vaccination (one-way ANOVA, P<0.001). Since mice vaccinated with CRT did not induce E7-specific T cell immune responses (see FIG. 2), the therapeutic effects (decrease in numbers of metastatic lung nodules) observed when constructs expressing CRT alone are administered may not be related to the anti-tumor immune responses (i.e., increase in antigen specific CTLs). To evaluate the role of CRT/E7 fusion polypeptides as compared to E7 or CRT polypeptide alone in the treatment of TC-1 tumor metastases in the lungs without any immune effector cells, nude (BALB/c nu/nu) mice (animals lacking both T helper and killer (CTL) lymphocytes and unable to induce either a humoral or a cellular immune response) were first challenged with 1×10⁴ TC-1 tumor cells per mouse via intravenous tail vein injection, as discussed above. Two days after challenge with TC-1 tumor cells, mice were given 16 Tg of CRT-encoding, E7-encoding or CRT/E7-encoding DNA, or empty plasmid without insert, via gene gun. On day 9 and day 16, these mice were boosted with the same regimen as the first vaccination. The mice were sacrificed on day 21. The pulmonary nodules of each mouse were evaluated and counted. As shown in FIG. 8, nude mice treated with constructs expressing CRT alone or the CRT/E7 fusion protein revealed a lower mean number of pulmonary nodules (6.0+2.8 for CRT, 2.5+0.7 for CRT/E7) compared to mice vaccinated with only wild-type E7 DNA (36.0+2.8), vector only (35.5+12.0) or naive group (47.5+2.1) (one-way ANOVA, P<0.001). These data indicated that the antitumor effects induced by CRT or CRT/E7 DNA vaccines were independent of anti-tumor immune responses.

Treatment with CRT or Chimeric CRT/E7 DNA Vaccines Significantly Reduced the Microvessel Density of the Tumors in the Lungs of Nude Mice: To determine whether this anti-tumor effect of CRT or CRT/E7 DNA in the absence of immune effectors is via an anti-angiogenic pathway, microvessel density (MVD) in the pulmonary tumors of nude mice treated with various DNA vaccines was measured. The endothelial cells were stained with anti-CD31 antibody as described above. All measurements were performed by a single pathologist without knowing any treatment data before counting. Nude mice (lacking a functional immune system) vaccinated with either the CRT or CRT/E7 DNA vaccines revealed much less MVD in the pulmonary tumors than nude mice treated with wild-type E7 or the control vector group (one-way ANOVA, P<0.001). These data indicated that mice treated with either CRT-expressing or CRT/E7 fusion protein-expressing vaccines could lead to anti-angiogenesis effects in the tumors.

Example 2

Self-replicating RNA Viruses Induce Enhanced Antigen-Specific CTL Responses

In one embodiment, the invention provides a self-replicating RNA replicon that can express a chimeric protein of the invention: a protein that comprises a first polypeptide domain comprising an endoplasmic reticulum (ER) chaperone polypeptide and a second polypeptide domain comprising at least one antigenic peptide. The following example describes studies which demonstrate that, using the methods of the invention, these constructs are effective for enhancing antigen-specific cytotoxic T lymphocyte (CTL) responses in vivo. As a model system, a fusion protein comprising HPV-16 E7 and *Mycobacterium tuberculosis* HSP70 was expressed in vivo in a Sindbis virus self-replicating RNA vector, SINrep5. The potency of antigen-specific immunity induced by this vector was determined. These results also demonstrate that fusion proteins comprising an ER chaperone polypeptide and an antigenic peptide expressed in vivo in a Sindbis virus self-replicating RNA vector are effective for enhancing antigen-specific CTL responses in vivo.

These experiments demonstrated that an RNA replicon vaccine containing E7/HSP70 fusion genes induced significantly higher E7-specific T cell-mediated immune responses than vaccines containing the wild type E7 gene in vaccinated mice. Furthermore, in vitro studies demonstrated that E7 antigen from E7/HSP70 RNA replicon-transfected apoptotic cells can be taken up by bone marrow-derived dendritic cells and presented more efficiently through the MHC class I pathway than wild-type E7 RNA replicon-transfected apoptotic cells. More importantly, the fusion of HSP70 to E7 converted a less effective vaccine into one with significant potency against E7-expressing tumors. This antitumor effect was dependent on NK cells and CD8$^+$ T cells. These results indicated that fusion of HSP70 to an antigen gene greatly enhanced the potency of self-replicating RNA vaccines. These results demonstrated that a Sindbis RNA vaccine linking E7 with HSP70 dramatically increased expansion and activation of E7-specific CD8+ T cells and NK cells, completely bypassing the CD4 arm and resulting in potent anti-tumor immunity against E7-expressing tumors.

The mechanism of Sindbis RNA vaccine to promote the anti-tumor effect was further investigated. It was found that the Sindbis E7/HSP70 RNA vaccine could induce apoptotic death of host cells and promote dendritic cells to phagocytose these cells, dramatically increasing the expansion and activation of E7-specific CD8+ T cells. This enhanced CD8 response resulted in potent anti-tumor immunity against an E7-expressing tumor cell line.

HPV-16 E7 was chosen as a model antigen for vaccine development because HPVs, particularly HPV-16, are associated with most cervical cancers, as discussed above.

Plasmid DNA Constructs and Preparation: The vectors pcDNA3-HSP70, pcDNA3-E7, and pcDNA3-E7/HSP70 were made as described by Chen (2000) supra. The Sindbis virus RNA replicon vector, SINrep5 has been described by, Bredenbeek, supra. Vectors SINrep5-HSP70, SINrep5-E7, and SINrep5-E7/HSP70 were made by isolating DNA fragments encoding *Mycobacterium tuberculosis* HSP70, HPV-16 E7 and chimeric E7/HSP70 by cutting pcDNA3-HSP70, pcDNA3-E7, and pcDNA3-E7/HSP70, respectively, with Xba I and Pme I restriction enzymes. Digested products were isolated using gels. These isolated DNA fragments were further cloned into the corresponding XabI and Pm1 I sites of the SINrep5 vector to induce SINrep5-HSP70, SINrep5-E7, and SINrep5-E7/HSP70 constructs. The accuracy of these constructs was confirmed by DNA sequencing.

In Vitro RNA Preparation: The generation of RNA transcripts from SINrep5-HSP70, SINrep5-E7, SINrep5-E7/HSP70 and SINrep5 was performed using the protocol described by Mandl (1998) Nature Med 4:1438-1440. SpeI was used to linearize DNA templates for the synthesis of RNA replicons from SINrep5-HSP70, SINrep5-E7, SINrep5-E7/HSP70 and SINrep5. RNA vaccines were transcribed in vitro and capped using SP6 RNA polymerase and capping analogue from a standard in vitro transcription kit (Life Technologies, Rockville, Md.) according to vendor's manual. After synthesis, DNA was removed by digestion with DNase I. Synthesized RNA was quantified and analyzed using denaturing formaldehyde agarose gels (Mandl (1998) supra). The purified RNA was divided into aliquots to be used for vaccination in animals and for transfection of a BHK21 cell line. The protein expression of the transcripts was assessed by transfection of the RNA into BHK21 cells using electroporation.

Cell Lines: Baby hamster kidney (BHK21) cells were obtained from the ATCC (Rockville, Md.) and grown in Glasgow MEM supplemented with 5% FBS, 10% tryptose phosphate broth, 2 mM glutamine, and antibiotics. Cells were kept at 37° C. in a humidified 5% CO2 atmosphere and were passaged every 2 days. The production and maintenance of TC-1 cells was done as described by Lin (1996) Cancer Res. 56:21-26. On the day of tumor challenge, TC-1 cells were harvested by trypsinization, washed twice with 1× Hanks buffered salt solution (HBSS), and finally resuspended in 1×HBSS to the designated concentration for injection.

ELISA for E7 Protein Expression of SINrep5 RNA vaccines: The expression of E7 protein from SINrep5-E7 and SINrep5-E7/HSP70 RNA was determined by an indirect ELISA method. The quantity of E7 protein was determined using cell lysates from SIN5rep-E7 or -E7/HSP70 transfected BHK21 cells. Briefly, ten million BHK21 cells were transfected with the 4 μg SINrep5, SINrep5-E7, SINrep5-HSP70 or SINrep5-E7/HSP70 RNA transcripts respectively via electroporation as described by Liljestrom (1991) J. Virol. 65:4107-4113. The transfected BHK21 cells were collected 16-20 hrs after electroporation. A 96-microwell plate was coated BHK 21 cell lysate, that were transfected with various SINrep5 RNAs in a final volume of 100 μl, and were incubated at 4° C. overnight. The bacteria-derived HPV-16 E7 proteins were used as a positive control. The wells were then blocked with PBS containing 20% fetal bovine serum. Diluted anti-E7 Ab (Zymed, San Francisco, Calif.) were added to the ELISA wells, and incubated on 37° C. for 2 hr. After washing with PBS containing 0.05% Tween-20, the plate was incubated with 1/2000 dilution of a peroxidase-conjugated rabbit anti-mouse IgG antibody (Zymed, San Francisco, Calif.) at room temperature (RT) for one hour. The plate was washed, developed with 1-Step™ Turbo TMB-ELISA (Pierce, Rockford, Ill.), and stopped with 1M $H_2SO_4$. The ELISA plate was read with a standard ELISA reader at 450 nm. The quantity of E7 protein of the cell lysates was then calculated and determined by comparing with the standardized E7 protein.

Mice: 6 to 8-week-old female C57BL/6 mice from the National Cancer Institute (Frederick, Md.) were purchased and kept in the oncology animal facility of the Johns Hopkins Hospital (Baltimore, Md.). All animal procedures were performed according to approved protocols and in accordance with recommendations for the proper use and care of laboratory animals.

RNA Vaccination: All SINrep5 RNA vaccines were generated using in vitro transcription as described above. RNA concentration was determined by optical density measured at 260 nm. The integrity and quantity of RNA transcripts were further checked using denaturing gel electrophoresis. Mice were vaccinated intramuscularly with 10 µg of various SINrep5 RNAs in the right hind leg except for SINrep5-E7/HSP70, which was administered in 0.1, 1, and 10 µg quantities.

ELISA for E7 Antibodies: Anti-HPV 16 E7 antibodies in the sera were determined by a direct ELISA as described by Wu (1995) Proc. Natl. Acad. Sci. USA 92:11671-1165. A 96-microwell plate was coated with 100 µl 5 µg/ml bacteria-derived HPV-16 E7 proteins and incubated at 4° C. overnight. The wells were then blocked with PBS containing 20% fetal bovine serum. Sera were prepared from mice on day 14 post-immunization, serially diluted in PBS, added to the ELISA wells, and incubated on 37° C. for 2 hr. After washing with PBS containing 0.05% Tween-20, the plate was incubated with 1/2000 dilution of a peroxidase-conjugated rabbit anti-mouse IgG antibody (Zymed, San Francisco, Calif.) at RT for one hour. The plate was washed, developed with 1-Step™ Turbo TMB-ELISA (Pierce, Rockford, Ill.), and stopped with 1M $H_2SO_4$. The ELISA plate was read with a standard ELISA reader at 450 nm.

Enzyme-Linked Immunoabsorbent Assay (ELISA) for INF-γ: Splenocytes were harvested 2 weeks after vaccination and cultured with the E7 peptide (aa 49-57) containing MHC class I epitope (Feltkamp (1993) Eur. J. Immunol. 23:2242-2249) or the E7 peptide (aa 30-67) containing MHC class II peptide (Tindle, supra), in a total volume of 2 ml of RPMI 1640, supplemented with 10% (vol/vol) fetal bovine serum, 50 units/ml penicillin and streptomycin, 2 mM L-glutamine, 1 mM sodium pyruvate, 2 mM nonessential amino acids in a 24-well tissue culture plate for 6 days. The supernatants were harvested and assayed for the presence of IFN-γ using ELISA kits (Endogen, Woburn, Mass.) according to the manufacturer's protocol.

Cytotoxic T Lymphocyte (CTL) Assays: CTL assays were performed in 96-well round-bottom plates as described by Corr (1999) J. Immunol. 163:4721-4727. Cytolysis was determined by quantitative measurements of lactate dehydrogenase (LDH) (Corr (1999) supra). Splenocytes were harvested 2 weeks after RNA vaccination and cultured with the E7 peptide (aa 49-57) in a total volume of 2 ml of RPMI 1640, supplemented with 10% (vol/vol) fetal bovine serum, 50 units/ml penicillin/streptomycin, 2 mM L-glutamine, 1 mM sodium pyruvate, 2 mM nonessential amino acids in a 24-well tissue culture plate for 6 days as effector cells. TC-1 tumor cells were used as target cells. The TC-1 cells mixed with splenocytes at various effector/target (E/T) ratios. After 5 hr incubation at 37° C., 50 µl of the cultured media were collected to assess the amount of LDH in the cultured media according to the manufacturer's protocol of the CytoToX™ assay kits (Promega, Madison, Wis.). The percentage of lysis was calculated from the following equation: 100× (A-B)/(C-D), where A is the reading of experimental-effector signal value, B is the effector spontaneous background signal value, C is maximum signal value from target cells, D is the target spontaneous background signal value.

Intracytoplasmic Cytokine Staining and Flow Cytometry Analysis: Splenocytes from naïve or vaccinated groups of mice were incubated with the E7 peptide (aa 30-67) that contains MHC class II peptide (Tindle (1999) supra) for detecting E7-specific $CD4^+$ T helper cell precursors. The E7 peptide was added at a concentration of 10 µg/ml for 20 hours. Golgistop™ (PharMingen, San Diego, Calif.) was added 6 hours before harvesting the cells from the culture. Cells were then washed once in FACScan™ buffer and stained with phycoerythrin (PE)-conjugated monoclonal rat anti-mouse CD4 antibody (PharMingen, San Diego, Calif.). Cells were subjected to intracellular cytokine staining using the Cytofix/Cytoperm™ kit according to the manufacturer's instructions (PharMingen). FITC-conjugated anti-IFN-γ antibody and the immunoglobulin isotype control antibody (rat IgG1) were all purchased from PharMingen. Analysis was done on a Becton Dickinson FACScan™ with CELLQuest™ software (Becton Dickinson Immunocytometry System, Mountain View, Calif.).

In Vivo Tumor Protection Experiments: For the tumor protection experiment, mice (5 per group) were immunized intramuscularly (IM) with different doses of SINrep5-HSP70, SINrep5-E7, SINrep5-E7/HSP70, and empty SINrep5 RNA vaccines. 14 days after immunization, mice were injected intravenously (IV) with $1 \times 10^4$ cells/mouse TC-1 tumor cells in the tail vein. Three weeks later, mice were euthanized. The lung weight and number of pulmonary nodules in each mouse was evaluated and counted by experimenters in a blinded fashion.

In Vivo Antibody Depletion Experiments: The procedure for in vivo antibody depletion has been described previously by, e.g., Lin (1996) supra; Wu (1995) J. Exp. Med. 182:1415-1421. In brief, mice were vaccinated with 1 µg self-replicating SINrep5-E7/HSP70 RNA intramuscularly and challenged with $1 \times 10^4$ cells/mouse TC-1 tumor cells via tail vein injection. Depletions were started one week prior to tumor challenge. MAb GK1.5 (Dialynas (1983) J. Immunol. 131: 2445) was used for CD4 depletion, MAb 2.43 Sarmiento (1980) J. Immunol. 125:2665) was used for CD8 depletion, and MAb PK136 (Koo (1986) J. Immunol. 137:3742) was used for NK1.1 depletion. Flow cytometry analysis revealed that >95% of the appropriate lymphocytes subset were depleted with a normal level of other subsets. Depletion was terminated on day 21 after tumor challenge.

Cell Surface Marker Staining and Flow Cytometry Analysis: Splenocytes removed from naïve or vaccinated groups of mice were immediately treated with cell surface marker staining as described by Ji (1999) Human Gene Therapy 10:2727-2740. Cells were then washed once in FACSCAN™ buffer and stained with PE-conjugated monoclonal rat anti-mouse NK1.1 antibody and FITC-conjugated monoclonal rat anti-mouse CD3 antibody (Pharmingen, San Diego, Calif.). The population of NK cells was stained with anti-NK1.1 antibody and not stained with anti-CD3 antibody. The percentages of NK cells in mice immunized with various self-replicating RNA vaccines was analyzed using flow cytometry.

Generation and Culture of Dendritic Cells (DCs) from Bone Marrow: DCs were generated by culture of bone marrow cells in the presence of GM-CSF as described by Lu (2000) J. Exp. Med. 191:541-550. Briefly, bone marrow was collected from the tibias of mice. Erythrocytes were lysed, and the remaining cells were passed through a nylon mesh to remove small pieces of bone and debris. The cells were collected and $1 \times 10^6$ cells/ml were placed in 24-well plates in RPMI 1640, supplemented with 5% FCS, 2 mM β-mercaptoethanol, 1% non-essential amino acids, 100 U/ml penicillin and 100 µg/ml streptomycin (Life Technologies, Rockville, Md.), and 100 U/ml GM-CSF (PharMingen, San Diego, Calif.). Two-thirds of the medium was replaced every 2 days, and non-adherent cells were harvested on day 7. The collected cells were characterized by flow cytometry analysis (FACS) for DC markers.

Generation of E7-Specific CD8+ T Cell Lines: Generation of E7-specific CD8+ cell lines was done by immunizing female C57BL/6 (H-2b) mice by intraperitoneal (IP) injection of Sig/E7/LAMP-1 vaccinia. Splenocytes were harvested on day 8. For initial in vitro stimulation, splenocytes were pulsed with IL-2 at a concentration of 20 U/ml and 1 µM E7 peptide (amino acids 49-57) for 6 days. Propagation of the E7-specific CTL cell line was performed in 24-well plates by mixing (2 ml/well) $1 \times 10^6$ splenocytes containing E7-specific CTLs with $3 \times 10^6$ irradiated splenocytes and pulsing them with IL-2 at a concentration of 20 U/ml and 1 µM E7 peptide (amino acids 49-57). This procedure was repeated every 6 days. The specificity of the E7 CTL line was characterized by the CTL assay. Flow cytometry was performed to demonstrate the expression of the CD8 marker.

In Vitro Cell Death Analysis: Ten million BHK21 cells were transfected with 4 µg SINrep5, SINrep5-E7, SINrep5-HSP70 or SINrep5-E7/HSP70 RNA transcripts as mentioned earlier. Native BHK21 cells or BHK21 cells that were electroporated without SINrep5 RNA were used as controls. BHK21 cells were collected and assessed every 24 hr, until hour 72. The percentages of apoptotic and necrotic BHK21 cells were analyzed using annexin V apoptosis detection kits (PharMingen, San Diego, Calif.) according to the manufacturer's protocol, followed by flow cytometry analysis.

CTL Assay Using DCs Pulsed with Apoptotis Cells as Target Cells: CTL assays using DCs pulsed with apoptosis cells as target cells were performed using a protocol similar to that described by Albert (1998) Nature 392:86-89; Albert (1998) J. Exp. Med. 188:1359-1368; with modification. Briefly, 10 million BHK21 cells were transfected with 4 µg of various self-replicating SINrep5 RNAs via electroporation. BHK21 cells were collected 16-20 hr after electroporation. The levels of E7 protein expression in BHK21 cells transfected with SINrep5-E7, or SINrep5-E7/HSP70 RNA transcripts were similar, as determined by ELISA. $3 \times 10^5$-transfected BHK21 cells were then co-incubated with $1 \times 10^5$ of bone marrow-derived DCs at 37° C. for 48 hr. These prepared DCs were then used as target cells and the Db-restricted E7-specific CD8+ T cells were used as the effector cells. CTL assays were performed with effector cells and targets cells ($1 \times 10^4$ per well) mixed together at various ratios (1:1, 3:1, 9:1, and 27:1) in a final volume of 200 µl. After 5 h incubation at 37° C., 50 µl of the cultured media were collected to assess the amount of LDH in the cultured media as described above. DCs co-incubated with untransfected BHK21 cells, transfected BHK21 cells alone, untreated DCs alone, and CD8+ T cell line alone were included as negative controls.

Construction and Characterization of Self-replicating RNA Constructs: Generation of plasmid DNA constructs and subsequent preparation of self-replicating SINrep5 RNA constructs was performed as described above. The SINrep5 vector contains the genes encoding Sindbis virus RNA replicase and the SP6 promoter (Bredenbeek (1993) supra). The schematic diagram of SINrep5, SINrep5-HSP70, SINrep5-E7, SINrep5-E7/HSP70 DNA constructs was shown in FIG. 9A. In addition, the schematic diagram of RNA transcript derived from these DNA constructs using SP6 RNA polymerase was shown in FIG. 9B. A methylated $M^7G$ "cap" is located at the 5' end of the mRNA, followed by a sequence responsible for the self-replication (replicase), the gene of interest (i.e., an MHC class I peptide epitope, an E7, an HSP70, an E7/HSP70, or the like), and a polyadenylated tail (AAAA). An ELISA was performed to demonstrate the expression of E7 protein by BHK21 cells transfected with the various self-replicating RNA constructs. SINrep5-E7 and SINrep5-E7/HSP70 expressed similar amounts of E7 protein.

Vaccination with Self-replicating SINrep5-E7/HSP70 RNA Enhances an E7-Specific Cytotoxic Immune Response: CD8+ T lymphocytes are one of the most crucial effectors for inducing anti-tumor immunity. To determine the quantity of E7-specific CD8+ T cell responses induced by the SINrep5-E7/HSP70 RNA vaccine, CTL assays were used. Mice were immunized with various SINrep5 self-replicating RNA vaccines via intramuscular injection. Splenocytes and serum samples were collected after 14 days. To perform the cytotoxicity assay, splenocytes from the various self-replicating SINrep5 RNA vaccines were cultured with E7 peptide (aa 49-57) containing MHC class I epitope for 6 days as effector cells. TC-1 tumor cells were as target cells. The TC-1 cells mixed with splenocytes at various E/T (effector/target ratio). Cytolysis was determined by quantitative measurements of LDH. CTL assays shown here are from one representative experiment of two performed.

The self-replicating RNA E7/HSP70 vaccine induced significantly higher percentage of specific lysis as compared with the other RNA vaccines (*: P<0.001, one-way ANOVA). The self-replicating SINrep5-E7/HSP70 induced a significantly higher percentage of specific lysis compared to mice vaccinated with the other SINrep5 RNA vaccines (P<0.001, one-way ANOVA). The ability of SINrep5-E7/HSP70 RNA to induce specific lysis was found to be approximately 4 times that of self-replicating SINrep5-E7 RNA (32.7% versus 8.8%, E/T ratio 45/1, P<0.001).

Vaccination with Self-replicating SINrep5-E7/HSP70 RNA Enhances E7-specific CD8+ T cells to Secrete High Levels of INF-γ: To determine the extent of the immunological response of E7-specific CD8+ T cells induced by self-replicating SINrep5-E7/HSP70 RNA, an ELISA was used to detect the concentration of INF-γ in the supernatant of cultured splenocytes. Mice were immunized with various self-replicating RNA vaccines via intramuscular injection. Splenocytes and serum samples were collected after 14 days. Splenocytes from the various self-replicating RNA vaccines were cultured in vitro with E7 peptide (aa 49-57) containing the MHC class I epitope (or without any peptide) for 6 days. As a negative control, an ELISA was also performed without peptide. Supernatants in the culture medium were collected to detect the INF-γ concentration using an ELISA.

Splenocytes from the self-replicating E7/HSP70 RNA group stimulated with E7 peptide (aa 49-57) secreted the highest concentration of INF-γ compared to the other RNA vaccines (P<0.001, one-way ANOVA). These results also indicated that fusion of HSP70 to E7 significantly enhances INF-γ-secreting E7-specific CD8+ T cell activity. Thus, the CD8+ T cells could be induced by the MHC class I epitope of E7. Note: the splenocytes from the self-replicating E7/HSP70 RNA group stimulated with E7 peptide (aa 49-57) secreted the highest concentration of INF-γ compared to the other RNA vaccines (*: P<0.001, one-way ANOVA).

Vaccination with Self-replicating SINrep5-E7/HSP70 RNA Does Not Induce Significant E7-Specific CD4+ T Cell-Mediated Immune Responses: To examine the generation of E7-specific CD4+ T precursor cells and cytokine profiles by each of these RNA vaccines, we performed double staining for CD4 surface marker and intracellular IFN-γ on splenocytes obtained from immunized mice, followed by flow cytometry analysis. The splenocytes were cultured in vitro with E7 peptide (aa 30-67) overnight and stained for both CD4 and intracellular IFN-γ. The E7 peptide (aa 30-67) contains a major T helper epitope in the E7 open reading frame protein of HPV-16 (Tindle (1991) supra). The percentage of IFN-γ-secreting CD4⁺ T cells was analyzed using flow cytometry.

Mice vaccinated with SINrep5-E7/HSP70 RNA induced a similar number of CD4⁺ IFN-γ⁺ double positive cells compared to mice vaccinated with SINrep5-E7 RNA ($15/3 \times 10^5$ splenocytes versus $12/3 \times 10^5$ splenocytes, p>0.05) or other RNA groups. There was no significant difference in the number of E7-specific CD4⁺ IFN-γ⁺ cells observed using flow cytometry staining among naïve mice or mice vaccinated with empty plasmid, E7, HSP70, or E7/HSP70 RNA. Splenocytes from Sig/E7/LAMP-1 DNA vaccinated mice (Ji (1999) supra) were used as positive controls for intracellular IFN-γ staining for this study.

The quantity of anti-HPV 16 E7 antibodies in the sera of the vaccinated mice was determined using a direct enzyme-linked immunoabsorbent assay (ELISA) 2 weeks after vaccination at various dilutions (1:100, 1:500, 1:1000). SINrep5-E7/HSP70 did not induce higher titers of E7-specific antibodies in the sera of vaccinated mice compared to that induced by other RNA vaccine constructs.

Vaccination with Self-Replicating SINrep5-E7/HSP70 RNA Protects Mice Against the Growth of TC-1 Tumors: To determine whether vaccination with the self-replicating SINrep5-E7/HSP70 RNA protected mice against E7-expressing tumors, an in vivo tumor protection experiment was performed using different doses of SINrep5-E7/HSP70 RNA administered intramuscularly in the right hind leg. Mice were similarly vaccinated with 10 µg self-replicating SINrep5, SINrep5-HSP70, and SINrep5-E7 RNA. Different doses of self-replicating SINrep5-E7/HSP70 RNA including 0.1 µg, 1 µg and 10 µg were also injected into mice. One week after vaccination, mice were challenged with TC-1 tumor cells via intravenous tail vein injection at a dose of $2 \times 10^4$ cells/mouse. Mice were monitored twice a week and sacrificed at day 21 after tumor challenge. The pulmonary nodules were assessed 21 days after tumor challenge. Lungs were dissected from the mice 35 days after vaccination with empty SINrep5 (10 µg), SINrep5-HSP70 (10 µg), SINrep5-E7 (10 µg), and SINrep5-E7/HSP70 RNA (0.1 µg, 1 µg, or 10 µg). The mean number of lung foci was used as a measurement of the effectiveness of the various self-replicating RNA vaccines at controlling HPV-16 E7-expressing tumor growth.

The mean pulmonary nodules of mice vaccinated with the self-replicating E7/HSP70 RNA vaccines (0.1 µg, 1 µg, and 10 µg) were much less compared to mice vaccinated with the other RNA vaccines (P<0.001, one-way ANOVA). These results demonstrated that self-replicating RNA SINrep5-E7/HSP70 vaccines protect mice from intravenous tumor challenge even at the low dosage of 0.1 µg while mice vaccinated with RNA from 10 µg SINrep5 without insert, 10 µg SINrep5-E7, or 10 µg SINrep5-HSP70 developed numerous lung nodules from TC-1 tumor challenge.

CD8⁺ T Cells and NK cells Are Important for the Anti-tumor Effect Induced by Vaccination with SINrep5-E7/HSP70 RNA Vaccines: To determine the types of lymphocytes that are important for protection against E7-expressing tumor cells, in vivo antibody depletion (of CD8⁺ T cells and NK cells) experiments were performed (the percentage of NK cells from the splenocytes of mice immunized with self-replicating RNA vaccines were higher than that without immunization and there was no significant difference between the percentage of NK cells among the various self-replicating RNA vaccines). The antibody depletion was started one week before tumor challenge and terminated on day 21 after tumor challenge.

The mean pulmonary nodules from mice depleted of CD8⁺ T cells and NK1.1 cells were significantly higher than those of non-depleted group. Furthermore, depletion of NK1.1 cells resulted in a higher mean number of tumor lung nodules than CD8+ depleted mice.

In comparison, the mean pulmonary nodules from mice depleted of CD4⁺ T cells resembled results obtained from non-depleted mice, indicating that CD4⁺ T cells were not critical in generating this effect. These results suggest that CD8⁺ T cells are essential for the antigen-specific anti-tumor immunity induced by SINrep5-E7/HSP70 RNA vaccine and that NK cells, while not limited to the E7/HSP70 RNA vaccine, play an important role as well.

It was also investigated whether the NK cell effect was limited to the E7/HSP70 vaccines or if it was the result of the vector used. Flow cytometry analysis of CD3(−), NK1.1(+) cells revealed that their presence was markedly increased in all constructs (E7/HSP70, E7, HSP70, and control plasmid) relative to naïve mice, indicating that NK cells were important effectors of the anti-tumor effect that are not limited to the E7/HSP70 vaccines.

Self-Replicating RNA Vaccines Induce Apoptosis: RNA transcribed in vitro from various plasmid SINrep5 RNA vaccines were transfected into BHK21 cells via electroporation. Electroporated BHK 21 cells without RNA and untreated BHK21 cells were used as controls. The percentages of apoptotic and necrotic BHK21 cells were stained by annexin V-FITC and propidium iodide (PI) followed by flow cytometry analysis.

The percentages of apoptotic BHK21 cells revealed statistical declines when transfected with SINrep5 RNA vaccines, 24 hr to 72 hr after (representative with SIN5-E7/HSP70 $70.3 \pm 3.6\%$ for 24 hr, $49.3 \pm 4.2\%$ for 48 hr, $18.0 \pm 3.1\%$ for 72 hr, P<0.001, one-way ANOVA). BHK21 cells transfected with SINrep5 RNA vaccines induced higher percentages after 24, 48 or 72 hours later compared to the other two control groups. No statistical differences could be found in the apoptotic percentages of various SINrep5 RNA vaccines.

Enhanced Presentation of E7 through the MHC Class I Pathway in Dendritic Cells Pulsed With Cells Transfected with SINrep5-E7/HSP70 RNA: A potential mechanism for the enhanced E7-specific CD8⁺ T cell immune responses in vivo is the presentation of E7 through the MHC class I pathway by uptake of apoptotic bodies from cells expressing various E7 constructs, also called "cross-priming". A cross priming experiment was performed to characterize the MHC class I presentation of E7 in dendritic cells pulsed with apoptotic bodies from BHK21 cells transfected with various self-replicating RNA. As mentioned previously, BHK21 cells have been shown to have stable high transfection efficiency and similar E7 expression among cells transfected with different E7-containing self-replicating RNA. Transfected BHK21 cells were co-incubated with bone marrow-derived DCs. DCs were used as target cells while E7-specific CD8⁺ T cells served as effector cells. CTL assays with various E/T ratios were performed.

DC target cells co-incubated with BHK21 cells transfected with SINrep5-E7/HSP70 RNA induced significantly higher percentages of specific lysis compared to DCs co-incubated with BHK21 cells transfected with SINrep5-E7 RNA (P<0.001). These results suggested that dendritic cells pulsed with apoptotic bodies containing E7/HSP70 fusion protein presented E7 antigen through the MHC class I pathway more efficiently than dendritic cells pulsed with apoptotic bodies containing wild-type E7 protein. Thus, the fusion of HSP70 to E7 enhanced E7-specific CD8+ T cell immune responses; and, while the invention is not limited by any particular mechanism, the enhancement was likely via "cross priming."

A number of embodiments of the invention have been described. Nevertheless, it will be understood that various modifications may be made without departing from the spirit and scope of the invention. Accordingly, other embodiments are within the scope of the following claims.

What is claimed is:

1. An isolated cell which has been modified to comprise a nucleic acid molecule encoding a fusion polypeptide useful as a vaccine composition, which molecule comprises:
   (a) a first nucleic acid sequence encoding a first polypeptide that comprises a calreticulin (CRT) polypeptide or a biologically active fragment thereof;
   (b) optionally, fused in frame with the first nucleic acid sequence, a linker nucleic acid sequence encoding a linker peptide; and
   (c) a second nucleic acid sequence that is linked in frame to said first nucleic acid sequence or to said linker nucleic acid sequence and that encodes an antigenic polypeptide or peptide.

2. The cell of claim 1, wherein the calreticulin polypeptide or biologically active fragment thereof comprises an amino acid sequence selected from the group consisting of:
   (a) a human calreticulin polypeptide;
   (b) the amino acid sequence of SEQ ID NO: 2;
   (c) the amino acid sequence of residues 1-180 of SEQ ID NO: 2; and
   (d) the amino acid sequence of residues 181-417 of SEQ ID NO: 2.

3. The cell of claim 1 or 2, wherein the nucleic acid molecule is operatively linked to
   (a) a promoter; and
   (b) optionally, additional regulatory sequences that regulate expression of said nucleic acid in a eukaryotic cell.

4. A pharmaceutical composition capable of inducing or enhancing an antigen-specific immune response, comprising a pharmaceutically and immunologically acceptable excipient in combination with the cell of claim 1 or 2.

5. A method of inducing or enhancing an antigen specific immune response in a subject comprising administering to said subject an effective amount of the pharmaceutical composition of claim 4, thereby inducing or enhancing said response.

6. A method of increasing the numbers or lytic activity of $CD8^+$ CTLs specific for the antigenic polypeptide or peptide comprised by the cell of claim 4 in a subject, comprising administering to said subject an effective number of cells of claim 4, wherein
   said antigenic polypeptide or peptide comprises an epitope that binds to, and is presented on the cell surface by, MHC class I proteins,
thereby increasing the numbers or activity of said CTLs.

7. A method of inhibiting growth or preventing re-growth of a tumor in a subject, comprising administering to said subject an effective number of cells of claim 4, wherein the antigenic polypeptide or peptide of said cells comprises one or more tumor-associated or tumor-specific epitopes present on said tumor in said subject, thereby inhibiting said growth or preventing said re-growth.

* * * * *